US009700356B2

(12) United States Patent
Donner et al.

(10) Patent No.: US 9,700,356 B2
(45) Date of Patent: Jul. 11, 2017

(54) SYSTEMS FOR AND METHODS OF FUSING A SACROILIAC JOINT

(71) Applicant: JCBD, LLC, Fort Collins, CO (US)

(72) Inventors: Edward Jeffrey Donner, Fort Collins, CO (US); Christopher Thomas Donner, Fort Collins, CO (US); Cathlene Donaldson, Waxhaw, NC (US); Ryan Lewis, Waxhaw, NC (US); Stuart Lindquist, Waxhaw, NC (US)

(73) Assignee: JCBD, LLC, Fort Collins, CO (US)

( * ) Notice: Subject to any disclaimer, the term of this patent is extended or adjusted under 35 U.S.C. 154(b) by 258 days.

(21) Appl. No.: 14/447,612

(22) Filed: Jul. 31, 2014

(65) Prior Publication Data

US 2015/0173805 A1 Jun. 25, 2015

Related U.S. Application Data

(60) Provisional application No. 61/914,409, filed on Dec. 11, 2013, provisional application No. 61/860,185, (Continued)

(51) Int. Cl.
*A61F 2/46* (2006.01)
*A61B 17/70* (2006.01)
(Continued)

(52) U.S. Cl.
CPC .......... *A61B 17/7055* (2013.01); *A61B 17/17* (2013.01); *A61B 17/1742* (2013.01);
(Continued)

(58) Field of Classification Search
CPC ...................................... A61B 17/17–17/1796
(Continued)

(56) References Cited

U.S. PATENT DOCUMENTS

| 4,488,542 A | 12/1984 | Helland |
| 4,569,338 A | 2/1986 | Edwards |

(Continued)

FOREIGN PATENT DOCUMENTS

| AU | 1753200 | 8/2000 |
| CN | 2265765 | 10/1997 |

(Continued)

OTHER PUBLICATIONS

Medtronic Sofamor Danek. Colorado 2™ Sacro-Iliac Fixation, Surgical Technique. © 2003 Medtronic Sofamor Danek USA, Inc.
(Continued)

*Primary Examiner* — Nicholas Plionis
(74) *Attorney, Agent, or Firm* — Polsinelli PC; Joshua J. Pranckun; Samuel Wade Johnson

(57) ABSTRACT

A sacroiliac joint fusion system including a joint implant, anchor element and delivery tool. The joint implant includes a bore extending non-parallel to the implant longitudinal axis. The anchor element is for receiving in the bore. The delivery tool includes an implant arm and anchor arm. The implant arm distal end is releasably coupled to the joint implant proximal end so the implant arm longitudinal axis is coaxial or parallel with the implant body longitudinal axis. An anchor arm distal end is engaged to the anchor element proximal end. The anchor arm is coupled to the implant arm such that the anchor element longitudinal axis is coaxially aligned with the bore longitudinal axis when the implant arm distal end is releasably coupled with the implant proximal end and the anchor arm distal end is engaged with the anchor element proximal end.

40 Claims, 50 Drawing Sheets

Related U.S. Application Data filed on Jul. 30, 2013, provisional application No. 61/955,126, filed on Mar. 18, 2014, provisional application No. 61/979,857, filed on Apr. 15, 2014.

(51) Int. Cl.
  *A61B 17/17* (2006.01)
  *A61B 17/68* (2006.01)
  *A61B 17/86* (2006.01)
  *A61B 17/88* (2006.01)
  *A61F 2/30* (2006.01)

(52) U.S. Cl.
  CPC .............. *A61B 17/68* (2013.01); *A61B 17/86* (2013.01); *A61B 17/8872* (2013.01); *A61F 2/46* (2013.01); *A61F 2002/30995* (2013.01)

(58) Field of Classification Search
  USPC ..................................................... 606/96–98
  See application file for complete search history.

(56) References Cited

U.S. PATENT DOCUMENTS

| | | | |
|---|---|---|---|
| 4,590,928 A | 5/1986 | Hunt et al. |
| 4,622,959 A | 11/1986 | Marcus |
| 4,714,469 A | 12/1987 | Kenna |
| 4,773,402 A | 9/1988 | Asher et al. |
| 4,794,918 A | 1/1989 | Wolter |
| 4,863,476 A | 9/1989 | Shepperd |
| 4,881,535 A | 11/1989 | Sohngen |
| 4,911,153 A | 3/1990 | Border |
| 4,920,958 A | 5/1990 | Walt et al. |
| 4,950,270 A | 8/1990 | Bowman et al. |
| 5,026,373 A | 6/1991 | Ray et al. |
| 5,052,375 A | 10/1991 | Stark et al. |
| 5,108,397 A | 4/1992 | White |
| 5,112,337 A | 5/1992 | Paulos et al. |
| 5,176,681 A | 1/1993 | Lawes et al. |
| 5,192,327 A | 3/1993 | Brantigan |
| 5,242,444 A | 9/1993 | MacMillan |
| 5,282,861 A | 2/1994 | Kaplan |
| 5,334,192 A | 8/1994 | Behrens |
| 5,334,205 A | 8/1994 | Cain |
| 5,336,225 A | 8/1994 | Zang |
| 5,368,546 A | 11/1994 | Stark et al. |
| 5,368,593 A | 11/1994 | Stark |
| 5,437,674 A | 8/1995 | Worcel et al. |
| 5,443,509 A | 8/1995 | Boucher et al. |
| 5,456,267 A | 10/1995 | Stark |
| 5,480,402 A | 1/1996 | Kim |
| 5,484,389 A | 1/1996 | Stark et al. |
| 5,591,235 A | 1/1997 | Kuslich |
| 5,593,407 A | 1/1997 | Reis |
| 5,607,424 A | 3/1997 | Tropiano |
| 5,609,635 A | 3/1997 | Michelson |
| 5,609,636 A | 3/1997 | Kohrs et al. |
| 5,626,434 A | 5/1997 | Cook |
| 5,658,337 A | 8/1997 | Kohrs et al. |
| 5,669,909 A | 9/1997 | Zdeblick et al. |
| 5,688,284 A | 11/1997 | Chervitz et al. |
| 5,743,914 A | 4/1998 | Skiba |
| 5,772,594 A | 6/1998 | Barrick |
| 5,823,975 A | 10/1998 | Stark et al. |
| 5,888,224 A | 3/1999 | Beckers et al. |
| 5,891,150 A | 4/1999 | Chan |
| 5,919,193 A | 7/1999 | Slavitt |
| 5,928,239 A | 7/1999 | Mirza |
| 5,929,782 A | 7/1999 | Stark et al. |
| 5,993,463 A | 11/1999 | Truwit |
| 6,053,916 A | 4/2000 | Moore |
| 6,056,749 A | 5/2000 | Kuslich |
| 6,063,442 A | 5/2000 | Cohen et al. |
| 6,175,758 B1 | 1/2001 | Kambin |
| 6,184,797 B1 | 2/2001 | Stark et al. |
| 6,236,891 B1 | 5/2001 | Ingle et al. |
| 6,241,771 B1 | 6/2001 | Gresser et al. |
| 6,290,724 B1 | 9/2001 | Marino |
| 6,296,595 B1 | 10/2001 | Stark et al. |
| 6,302,885 B1 | 10/2001 | Essiger |
| 6,322,562 B1 | 11/2001 | Wolter |
| 6,371,123 B1 | 4/2002 | Stark et al. |
| 6,413,278 B1 | 7/2002 | Marchosky |
| 6,432,107 B1 | 8/2002 | Ferree |
| 6,432,140 B1 | 8/2002 | Lin |
| 6,515,593 B1 | 2/2003 | Stark et al. |
| 6,520,990 B1 | 2/2003 | Ray |
| 6,540,707 B1 | 4/2003 | Stark et al. |
| 6,547,795 B2 | 4/2003 | Schneiderman |
| 6,547,823 B2 | 4/2003 | Scarborough et al. |
| 6,558,423 B1 | 5/2003 | Michelson |
| 6,565,605 B2 | 5/2003 | Goble et al. |
| 6,572,622 B1 | 6/2003 | Schäfer et al. |
| 6,579,318 B2 | 6/2003 | Varga et al. |
| 6,607,487 B2 | 8/2003 | Chang et al. |
| 6,635,059 B2 | 10/2003 | Randall et al. |
| 6,641,614 B1 | 11/2003 | Wagner |
| 6,660,224 B2 | 12/2003 | Lefebvre et al. |
| 6,663,669 B1 | 12/2003 | Reiley |
| 6,669,698 B1 | 12/2003 | Tromanhauser et al. |
| 6,682,563 B2 | 1/2004 | Scharf |
| 6,682,567 B1 | 1/2004 | Schroeder |
| 6,716,245 B2 | 4/2004 | Pasquet et al. |
| 6,723,099 B1 | 4/2004 | Goshert |
| 6,743,256 B2 | 6/2004 | Mason |
| 6,746,451 B2 | 6/2004 | Middleton et al. |
| 6,824,564 B2 | 11/2004 | Crozet |
| 6,827,670 B1 | 12/2004 | Stark et al. |
| 6,835,208 B2 | 12/2004 | Marchosky |
| 6,855,166 B2 | 2/2005 | Kohrs |
| 6,855,167 B2 | 2/2005 | Shimp et al. |
| 6,860,902 B2 | 3/2005 | Reiley |
| 6,872,187 B1 | 3/2005 | Stark et al. |
| 6,875,236 B2 | 4/2005 | Reiley |
| 6,902,567 B2 | 6/2005 | Del Medico |
| 6,908,465 B2 | 6/2005 | von Hoffmann et al. |
| 6,945,448 B2 | 9/2005 | Medlin et al. |
| 6,972,019 B2 | 12/2005 | Michelson |
| 6,974,461 B1 | 12/2005 | Wolter |
| 7,011,660 B2 | 3/2006 | Sherman et al. |
| 7,087,056 B2 | 8/2006 | Vaughan |
| 7,087,058 B2 | 8/2006 | Cragg |
| 7,108,828 B2 | 9/2006 | Lefebvre et al. |
| 7,144,399 B2 | 12/2006 | Hayes et al. |
| 7,163,560 B2 | 1/2007 | Mason |
| 7,192,447 B2 | 3/2007 | Rhoda |
| 7,201,775 B2 | 4/2007 | Gorensek et al. |
| 7,208,222 B2 | 4/2007 | Rolfe et al. |
| 7,217,291 B2 | 5/2007 | Zucherman et al. |
| 7,229,448 B2 | 6/2007 | Goble et al. |
| 7,235,101 B2 | 6/2007 | Berry et al. |
| 7,235,105 B2 | 6/2007 | Jackson |
| 7,247,157 B2 | 7/2007 | Prager et al. |
| 7,255,712 B1 | 8/2007 | Steinberg |
| 7,303,563 B2 | 12/2007 | Poyner et al. |
| 7,331,995 B2 | 2/2008 | Eisermann et al. |
| 7,396,360 B2 | 7/2008 | Lieberman |
| 7,410,501 B2 | 8/2008 | Michelson |
| 7,416,537 B1 | 8/2008 | Stark et al. |
| 7,458,991 B2 | 12/2008 | Wang et al. |
| 7,465,317 B2 | 12/2008 | Malberg et al. |
| 7,520,898 B2 | 4/2009 | Re et al. |
| 7,537,616 B1 | 5/2009 | Branch et al. |
| 7,575,600 B2 | 8/2009 | Zucherman et al. |
| 7,621,939 B2 | 11/2009 | Zucherman et al. |
| 7,635,447 B2 | 12/2009 | Hamman et al. |
| 7,637,954 B2 | 12/2009 | Michelson |
| 7,641,697 B2 | 1/2010 | Reiley |
| 7,648,509 B2 | 1/2010 | Stark |
| 7,666,209 B2 | 2/2010 | Zucherman et al. |
| 7,670,383 B1 | 3/2010 | Brown et al. |
| 7,704,279 B2 | 4/2010 | Moskowitz et al. |
| 7,713,290 B2 | 5/2010 | Vaughan |
| 7,740,795 B2 | 6/2010 | Wang et al. |

(56) References Cited

U.S. PATENT DOCUMENTS

| | | |
|---|---|---|
| 7,771,441 B2 | 8/2010 | Cerundolo |
| 7,789,895 B2 | 9/2010 | Heinz |
| 7,794,465 B2 | 9/2010 | Marik et al. |
| 7,799,081 B2 | 9/2010 | McKinley |
| 7,819,869 B2 | 10/2010 | Godara et al. |
| 7,824,404 B2 | 11/2010 | Godara et al. |
| 7,837,732 B2 | 11/2010 | Zucherman et al. |
| 7,837,734 B2 | 11/2010 | Zucherman et al. |
| 7,846,162 B2 | 12/2010 | Nelson et al. |
| 7,850,690 B2 | 12/2010 | Frigg et al. |
| 7,850,719 B2 | 12/2010 | Gournay et al. |
| 7,850,732 B2 | 12/2010 | Heinz |
| 7,909,871 B2 | 3/2011 | Abdou |
| 7,918,891 B1 | 4/2011 | Curran et al. |
| 7,922,765 B2 | 4/2011 | Reiley |
| 7,963,970 B2 | 6/2011 | Marino et al. |
| 7,972,363 B2 | 7/2011 | Moskowitz et al. |
| 7,972,382 B2 | 7/2011 | Foley et al. |
| 7,985,255 B2 | 7/2011 | Bray et al. |
| 8,034,114 B2 | 10/2011 | Reiley |
| 8,034,115 B2 | 10/2011 | Reiley |
| 8,048,164 B2 | 11/2011 | Reiley |
| 8,070,782 B2 | 12/2011 | McKay |
| 8,075,561 B2 | 12/2011 | Wolter |
| 8,083,796 B1 | 12/2011 | Raiszadeh et al. |
| 8,088,163 B1 | 1/2012 | Kleiner |
| 8,128,666 B2 | 3/2012 | Falahee |
| 8,162,981 B2 | 4/2012 | Vestgaarden |
| 8,187,332 B2 | 5/2012 | McLuen |
| 8,202,305 B2 | 6/2012 | Reiley |
| 8,221,428 B2 | 7/2012 | Trieu |
| 8,231,661 B2 | 7/2012 | Carls et al. |
| 8,308,779 B2 | 11/2012 | Reiley |
| 8,308,794 B2 | 11/2012 | Martinson et al. |
| 8,317,862 B2 | 11/2012 | Troger et al. |
| 8,343,189 B2 | 1/2013 | Assell et al. |
| 8,343,219 B2 | 1/2013 | Allain et al. |
| 8,348,950 B2 | 1/2013 | Assell et al. |
| 8,388,667 B2 | 3/2013 | Reiley |
| 8,414,648 B2 | 4/2013 | Reiley |
| 8,425,570 B2 | 4/2013 | Reiley |
| 8,425,603 B2 | 4/2013 | Reichen et al. |
| 8,439,925 B2 | 5/2013 | Marino et al. |
| 8,444,693 B2 | 5/2013 | Reiley |
| 8,454,618 B2 | 6/2013 | Stark |
| 8,470,004 B2 | 6/2013 | Reiley |
| 8,470,037 B2 | 6/2013 | Re et al. |
| 8,480,755 B2 | 7/2013 | Reiley |
| 8,491,572 B2 | 7/2013 | Martinson et al. |
| 8,491,653 B2 | 7/2013 | Zucherman et al. |
| 8,496,712 B2 | 7/2013 | Reiley |
| 8,501,690 B2 | 8/2013 | Stark |
| 8,518,120 B2 | 8/2013 | Glerum |
| 8,551,171 B2 | 10/2013 | Johnson et al. |
| 8,579,912 B2 | 11/2013 | Isaza et al. |
| 8,585,744 B2 | 11/2013 | Duggal et al. |
| D697,209 S | 1/2014 | Walthall, Jr. et al. |
| 8,623,062 B2 | 1/2014 | Kondrashov |
| 8,778,026 B2 | 7/2014 | Mauldin |
| 8,808,305 B2 | 8/2014 | Kleiner |
| 8,808,336 B2 | 8/2014 | Duggal et al. |
| 8,808,377 B2 | 8/2014 | Donner |
| 8,808,380 B2 | 8/2014 | Fox et al. |
| 8,808,389 B2 | 8/2014 | Reiley |
| 8,821,546 B2 | 9/2014 | Vaughan |
| 8,840,651 B2 | 9/2014 | Reiley |
| 8,894,708 B2 | 11/2014 | Thalgott et al. |
| 8,979,928 B2 | 3/2015 | Donner |
| 8,992,579 B1 | 3/2015 | Gustine et al. |
| 9,017,407 B2 | 4/2015 | Donner |
| 9,039,768 B2 | 5/2015 | Voellmicke |
| 9,044,321 B2 | 6/2015 | Mauldin |
| 9,060,815 B1 | 6/2015 | Gustine et al. |
| 9,333,090 B2 | 5/2016 | Donner et al. |
| 2001/0005796 A1 | 6/2001 | Zdeblick et al. |
| 2001/0018616 A1 | 8/2001 | Schwab |
| 2001/0020143 A1 | 9/2001 | Stark et al. |
| 2002/0029784 A1 | 3/2002 | Stark et al. |
| 2002/0032484 A1 | 3/2002 | Hyde, Jr. |
| 2002/0068977 A1 | 6/2002 | Jackson |
| 2002/0082701 A1 | 6/2002 | Zdeblick et al. |
| 2002/0087161 A1 | 7/2002 | Randall et al. |
| 2002/0147461 A1 | 10/2002 | Aldrich et al. |
| 2002/0147496 A1 | 10/2002 | Belef et al. |
| 2002/0183846 A1 | 12/2002 | Kuslich et al. |
| 2003/0114931 A1 | 6/2003 | Lee et al. |
| 2003/0124486 A1 | 7/2003 | McDevitt |
| 2003/0181981 A1 | 9/2003 | Lemaire |
| 2003/0208202 A1 | 11/2003 | Falahee |
| 2004/0073216 A1 | 4/2004 | Lieberman |
| 2004/0127988 A1 | 7/2004 | Goble et al. |
| 2004/0162558 A1 | 8/2004 | Hegde et al. |
| 2004/0162616 A1 | 8/2004 | Simonton |
| 2004/0186482 A1 | 9/2004 | Kolb et al. |
| 2004/0199256 A1 | 10/2004 | Wang |
| 2004/0220668 A1 | 11/2004 | Eisermann et al. |
| 2004/0228901 A1 | 11/2004 | Trieu |
| 2004/0249675 A1 | 12/2004 | Stark et al. |
| 2004/0260286 A1 | 12/2004 | Ferree |
| 2005/0043660 A1 | 2/2005 | Stark et al. |
| 2005/0101887 A1 | 5/2005 | Stark et al. |
| 2005/0113652 A1 | 5/2005 | Stark et al. |
| 2005/0131539 A1 | 6/2005 | Kohrs |
| 2005/0149192 A1 | 7/2005 | Zucherman et al. |
| 2005/0154391 A1 | 7/2005 | Doherty et al. |
| 2005/0203515 A1 | 9/2005 | Doherty et al. |
| 2005/0216088 A1 | 9/2005 | McKinley et al. |
| 2005/0240264 A1 | 10/2005 | Tokish, Jr. et al. |
| 2005/0245925 A1 | 11/2005 | Iki et al. |
| 2005/0267482 A1 | 12/2005 | Hyde, Jr. |
| 2005/0273099 A1 | 12/2005 | Baccelli et al. |
| 2006/0054171 A1 | 3/2006 | Dall |
| 2006/0058876 A1 | 3/2006 | McKinley |
| 2006/0069438 A1 | 3/2006 | Zucherman et al. |
| 2006/0085068 A1 | 4/2006 | Barry |
| 2006/0089716 A1 | 4/2006 | Felix |
| 2006/0095134 A1 | 5/2006 | Trieu et al. |
| 2006/0129244 A1 | 6/2006 | Ensign |
| 2006/0147332 A1 | 7/2006 | Jones et al. |
| 2006/0161154 A1 | 7/2006 | McAfee |
| 2006/0167547 A1 | 7/2006 | Suddaby |
| 2006/0229729 A1 | 10/2006 | Gordon |
| 2007/0027543 A1 | 2/2007 | Gimble et al. |
| 2007/0055374 A1 | 3/2007 | Copf, Jr. et al. |
| 2007/0155588 A1 | 7/2007 | Stark et al. |
| 2007/0156241 A1 | 7/2007 | Reiley et al. |
| 2007/0162134 A1 | 7/2007 | Marnay et al. |
| 2007/0179610 A1 | 8/2007 | Biedermann |
| 2007/0179621 A1 | 8/2007 | McClellan, III et al. |
| 2007/0198093 A1 | 8/2007 | Brodke et al. |
| 2007/0225714 A1 | 9/2007 | Gradl |
| 2007/0239164 A1 | 10/2007 | Prager et al. |
| 2007/0265621 A1 | 11/2007 | Matthis et al. |
| 2007/0270879 A1 | 11/2007 | Isaza et al. |
| 2007/0270968 A1 | 11/2007 | Baynham |
| 2007/0276501 A1 | 11/2007 | Betz et al. |
| 2007/0293949 A1 | 12/2007 | Salerni et al. |
| 2007/0299525 A1 | 12/2007 | Binotto |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0039843 A1 | 2/2008 | Abdou |
| 2008/0045968 A1 | 2/2008 | Yu et al. |
| 2008/0065215 A1 | 3/2008 | Reiley |
| 2008/0133016 A1 | 6/2008 | Heinz |
| 2008/0140082 A1 | 6/2008 | Erdem et al. |
| 2008/0140207 A1 | 6/2008 | Olmos |
| 2008/0154314 A1 | 6/2008 | McDevitt |
| 2008/0183293 A1 | 7/2008 | Parry et al. |
| 2008/0228276 A1 | 9/2008 | Mathews et al. |
| 2008/0262621 A1 | 10/2008 | Gorek |
| 2008/0281425 A1 | 11/2008 | Thalgott et al. |
| 2008/0288081 A1 | 11/2008 | Scrafton et al. |
| 2008/0300685 A1 | 12/2008 | Carls et al. |

(56) References Cited

U.S. PATENT DOCUMENTS

| | | |
|---|---|---|
| 2009/0018660 A1 | 1/2009 | Roush |
| 2009/0024174 A1 | 1/2009 | Stark |
| 2009/0024217 A1 | 1/2009 | Levy |
| 2009/0043394 A1 | 2/2009 | Zdeblick et al. |
| 2009/0076553 A1 | 3/2009 | Wolter |
| 2009/0088849 A1 | 4/2009 | Armstrong et al. |
| 2009/0105833 A1 | 4/2009 | Hovda et al. |
| 2009/0105834 A1 | 4/2009 | Hovda et al. |
| 2009/0131986 A1 | 5/2009 | Lee et al. |
| 2009/0132035 A1 | 5/2009 | Roth et al. |
| 2009/0149957 A1 | 6/2009 | Burd et al. |
| 2009/0192621 A1 | 7/2009 | Winslow et al. |
| 2009/0216238 A1 | 8/2009 | Stark |
| 2009/0216276 A1 | 8/2009 | Pasquet |
| 2009/0248163 A1 | 10/2009 | King et al. |
| 2009/0259261 A1 | 10/2009 | Reiley |
| 2009/0259316 A1 | 10/2009 | Ginn et al. |
| 2009/0287254 A1 | 11/2009 | Nayet et al. |
| 2009/0306671 A1 | 12/2009 | McCormack et al. |
| 2010/0057204 A1 | 3/2010 | Kadaba |
| 2010/0094290 A1 | 4/2010 | Vaidya |
| 2010/0100135 A1 | 4/2010 | Phan |
| 2010/0106200 A1 | 4/2010 | Stark |
| 2010/0121160 A1 | 5/2010 | Stark et al. |
| 2010/0137910 A1 | 6/2010 | Cawley et al. |
| 2010/0137919 A1 | 6/2010 | Wolter |
| 2010/0152785 A1 | 6/2010 | Forton et al. |
| 2010/0179552 A1 | 7/2010 | Wolter |
| 2010/0185292 A1 | 7/2010 | Hochschuler |
| 2010/0204795 A1 | 8/2010 | Greenhalgh |
| 2010/0211176 A1 | 8/2010 | Greenhalgh |
| 2010/0268228 A1 | 10/2010 | Petersen |
| 2010/0286779 A1 | 11/2010 | Thibodeau |
| 2010/0286785 A1 | 11/2010 | Grayson |
| 2010/0292796 A1 | 11/2010 | Greenhalgh |
| 2010/0292800 A1 | 11/2010 | Zubok |
| 2010/0305702 A1 | 12/2010 | Michelson |
| 2010/0305704 A1 | 12/2010 | Messerli |
| 2010/0324607 A1 | 12/2010 | Davis |
| 2010/0331981 A1 | 12/2010 | Mohammed |
| 2011/0034957 A1 | 2/2011 | Biedermann |
| 2011/0046737 A1 | 2/2011 | Teisen |
| 2011/0071568 A1 | 3/2011 | Ginn et al. |
| 2011/0071635 A1 | 3/2011 | Zhang et al. |
| 2011/0087294 A1 | 4/2011 | Reiley |
| 2011/0093074 A1 | 4/2011 | Glerum |
| 2011/0098816 A1 | 4/2011 | Jacob et al. |
| 2011/0098817 A1 | 4/2011 | Eckhardt et al. |
| 2011/0118796 A1 | 5/2011 | Reiley |
| 2011/0172774 A1 | 7/2011 | Varela |
| 2011/0184518 A1 | 7/2011 | Trieu |
| 2011/0184519 A1 | 7/2011 | Trieu |
| 2011/0184520 A1 | 7/2011 | Trieu |
| 2011/0185306 A1 | 7/2011 | Aravamudan |
| 2011/0230966 A1 | 9/2011 | Trieu |
| 2011/0238181 A1 | 9/2011 | Trieu |
| 2011/0264233 A1 | 10/2011 | Song |
| 2011/0295272 A1 | 12/2011 | Assell et al. |
| 2012/0010714 A1 | 1/2012 | Moskowitz et al. |
| 2012/0022535 A1 | 1/2012 | Mayer et al. |
| 2012/0022595 A1 | 1/2012 | Pham et al. |
| 2012/0029641 A1 | 2/2012 | Curran et al. |
| 2012/0032808 A1 | 2/2012 | Cherubini |
| 2012/0035729 A1 | 2/2012 | Glerum |
| 2012/0083883 A1 | 4/2012 | Ginn |
| 2012/0095560 A1 | 4/2012 | Donner |
| 2012/0116454 A1 | 5/2012 | Edidin et al. |
| 2012/0116806 A1 | 5/2012 | Stark et al. |
| 2012/0150300 A1 | 6/2012 | Nihalani |
| 2012/0185049 A1 | 7/2012 | Varela |
| 2012/0209388 A1 | 8/2012 | Curran et al. |
| 2012/0253398 A1 | 10/2012 | Metcalf et al. |
| 2012/0259370 A1 | 10/2012 | Vaidya |
| 2012/0271200 A1 | 10/2012 | Martinson et al. |
| 2012/0271424 A1 | 10/2012 | Crawford |
| 2012/0296428 A1 | 11/2012 | Donner |
| 2012/0316565 A1 | 12/2012 | Stark |
| 2012/0323285 A1 | 12/2012 | Assell et al. |
| 2013/0006361 A1 | 1/2013 | Glerum |
| 2013/0018427 A1 | 1/2013 | Pham et al. |
| 2013/0023994 A1 | 1/2013 | Glerum |
| 2013/0030456 A1 | 1/2013 | Assell et al. |
| 2013/0035723 A1 | 2/2013 | Donner |
| 2013/0035727 A1 | 2/2013 | Datta |
| 2013/0053854 A1 | 2/2013 | Schoenefeld et al. |
| 2013/0053902 A1 | 2/2013 | Trudeau |
| 2013/0053964 A1 | 2/2013 | Talwar |
| 2013/0060337 A1 | 3/2013 | Petersheim et al. |
| 2013/0066426 A1 | 3/2013 | Martinson et al. |
| 2013/0085535 A1 | 4/2013 | Greenhalgh et al. |
| 2013/0090735 A1 | 4/2013 | Mermuys et al. |
| 2013/0116790 A1 | 5/2013 | Seifert |
| 2013/0123850 A1 | 5/2013 | Schoenefeld et al. |
| 2013/0123923 A1 | 5/2013 | Pavlov et al. |
| 2013/0144343 A1 | 6/2013 | Arnett et al. |
| 2013/0158669 A1 | 6/2013 | Sungarian et al. |
| 2013/0197590 A1 | 8/2013 | Assell et al. |
| 2013/0218215 A1 | 8/2013 | Ginn et al. |
| 2013/0226181 A1 | 8/2013 | Assell et al. |
| 2013/0231746 A1 | 9/2013 | Ginn et al. |
| 2013/0245703 A1 | 9/2013 | Warren et al. |
| 2013/0253650 A1 | 9/2013 | Ashley et al. |
| 2013/0282012 A1 | 10/2013 | Stark |
| 2013/0295202 A1 | 11/2013 | Stark |
| 2013/0297035 A1 | 11/2013 | Reiley |
| 2014/0012330 A1 | 1/2014 | Johnson, II et al. |
| 2014/0012340 A1 | 1/2014 | Beck et al. |
| 2014/0031934 A1 | 1/2014 | Trieu |
| 2014/0039628 A1 | 2/2014 | DeLurio et al. |
| 2014/0046380 A1 | 2/2014 | Asfora |
| 2014/0074175 A1 | 3/2014 | Ehler et al. |
| 2014/0088707 A1 | 3/2014 | Donner et al. |
| 2014/0100662 A1 | 4/2014 | Patterson et al. |
| 2014/0114415 A1 | 4/2014 | Tyber |
| 2014/0135850 A1 | 5/2014 | Parent et al. |
| 2014/0135927 A1 | 5/2014 | Pavlov et al. |
| 2014/0156007 A1 | 6/2014 | Pabst et al. |
| 2014/0200618 A1 | 7/2014 | Donner et al. |
| 2014/0249581 A1 | 9/2014 | Stachniak |
| 2014/0257294 A1 | 9/2014 | Gedet et al. |
| 2014/0257399 A1 | 9/2014 | Rezach |
| 2014/0257408 A1 | 9/2014 | Trieu et al. |
| 2014/0257411 A1 | 9/2014 | Rezach |
| 2014/0257486 A1 | 9/2014 | Alheidt |
| 2014/0277460 A1 | 9/2014 | Schifano |
| 2014/0277478 A1 | 9/2014 | Moore |
| 2014/0277504 A1 | 9/2014 | Forton et al. |
| 2014/0288601 A1 | 9/2014 | Baynham |
| 2014/0336763 A1 | 11/2014 | Donner et al. |
| 2014/0336775 A1 | 11/2014 | Reiley |
| 2014/0343678 A1 | 11/2014 | Suddaby et al. |
| 2015/0039037 A1 | 2/2015 | Donner et al. |
| 2015/0094765 A1 | 4/2015 | Donner et al. |
| 2015/0150683 A1 | 6/2015 | Donner et al. |
| 2015/0182268 A1 | 7/2015 | Donner et al. |
| 2015/0209087 A1 | 7/2015 | Donner et al. |
| 2015/0250612 A1 | 9/2015 | Schifano |
| 2015/0342753 A1 | 12/2015 | Donner et al. |
| 2016/0157897 A1 | 6/2016 | Vaidya |
| 2016/0184105 A1 | 6/2016 | Donner et al. |
| 2016/0324643 A1 | 11/2016 | Donner et al. |

FOREIGN PATENT DOCUMENTS

| | | |
|---|---|---|
| CN | 201073333 Y | 6/2008 |
| CN | 201139628 | 10/2008 |
| CN | 201275132 | 7/2009 |
| CN | 201275133 | 7/2009 |
| CN | 201275134 | 7/2009 |
| CN | 202235633 U | 5/2012 |
| DE | 102013011322 A1 | 5/2014 |
| EP | 1663037 B1 | 6/2006 |
| JP | 2007-275592 | 10/2007 |
| KR | 10-1037206 | 5/2011 |

(56) References Cited

FOREIGN PATENT DOCUMENTS

| | | |
|---|---|---|
| RU | 2364359 C1 | 8/2009 |
| WO | WO 93/08745 A1 | 5/1993 |
| WO | WO 95/23559 | 9/1995 |
| WO | WO 95/31947 | 11/1995 |
| WO | WO 98/48717 | 11/1998 |
| WO | WO 01/30264 A2 | 5/2001 |
| WO | WO 01/95823 A1 | 12/2001 |
| WO | WO 02/067759 A2 | 9/2002 |
| WO | WO 2006/020463 A1 | 2/2006 |
| WO | WO 2006/099270 | 9/2006 |
| WO | WO 2007/022790 A1 | 3/2007 |
| WO | WO 2007/115295 A2 | 10/2007 |
| WO | WO 2008/011410 A2 | 1/2008 |
| WO | WO 2008/088685 A2 | 7/2008 |
| WO | WO 2008/089537 A1 | 7/2008 |
| WO | WO 2009/011774 A2 | 1/2009 |
| WO | WO 2009/029074 A1 | 3/2009 |
| WO | WO 2009/108318 A2 | 9/2009 |
| WO | WO 2010/045749 A1 | 4/2010 |
| WO | WO 2010/065015 A1 | 6/2010 |
| WO | WO 2010/108166 A1 | 9/2010 |
| WO | WO 2011014135 A2 | 2/2011 |
| WO | WO 2011/056690 A2 | 5/2011 |
| WO | WO 2011/066053 A2 | 6/2011 |
| WO | WO 2011/087912 A1 | 7/2011 |
| WO | WO 2011/091349 A2 | 7/2011 |
| WO | WO 2012/015976 A1 | 2/2012 |
| WO | WO 2012/174485 A1 | 12/2012 |
| WO | WO 2013/020123 A2 | 2/2013 |
| WO | WO 2013/166496 A1 | 11/2013 |
| WO | WO 2014/055529 A2 | 4/2014 |
| WO | WO 2014/074853 A1 | 5/2014 |

OTHER PUBLICATIONS

Medtronic Sofamor Danek. Colorado 2™ The New Revolution, Surgical Technique. © 2000 Medtronic Sofamor Danek, Inc.
Synthes GmbH. Sacral Bars. Fixation of the posterior pelvis in cases of fractures or sacroiliac joint dislocations. © Apr. 2009 Synthes, Inc.
Australian Examination Report, AU2014204494, dated May 15, 2015.
Australian Patent Examination Report No. 1, AU2012312658, dated Jul. 18, 2016.
Chinese Office Action, CN201180001537.4, dated Mar. 19, 2015.
EP Examination Report, EP11733183.5, dated Sep. 9, 2015.
European Search Report, EP12834000.7, dated Jul. 13, 2015.
Japanese Office Action, JP2015-042238, dated Dec. 22, 2015.
Taiwan Examination Report, TW100114376, dated Oct. 5, 2015.
Arman et al. The Human Sacrum and Safe Approaches for Screw Placement. *Journal of Clinical Neuroscience* 2008 Elsevier Inc.;16(2009):1046-1049.
Atlihan et al. Anatomy of the Posterior Illiac Crest as a Reference to Sacral Bar Insertion. *Clin Orthop* 2004;418:141-145.
Baria, Dinah, "Sacroiliac Joint Biomechanics and Effects of Fusion" (2010). Open Access Dissertations. Paper 466. http://scholarlyrepository.miami.edu/oa_dissertations, 179 pages.
Belanger, et al. "Sacroiliac Arthrodesis Using a Posterior Midline Fascial Splitting Approach and Pedicle Screw Instrumentation: A New Technique." Journal of Spinal Disorders, vol. 14 No. 2, pp. 118-124, 2001.
Buchowski, et al. "Functional and Radiographic Outcome of Sacroiliac Arthrodesis for the Disorders of the Sacroiliac Joint." The Spine Journal, 5, 2005, pp. 520-528.
Cecil et al. Projection of the S2 Pedicle Onto the Posterolateral Surface of the Ilium: A Technique for Lag Screw Fixation, Sacral Fractures or Sacroiliac Joint Dislocations. *Spine* 1996;21(7):875-878.
Chang et al. Low Profile Pelvic Fixation. *Spine* 2009;34(5):436-440.
Dayer R. et al. Pelvic fixation for neuromuscular scoliosis deformity correction. *Curr Rev Musculoskelet Med* (2012) 5:91-101.
DePuy Spine. ISOLA® Spinopelvic System, Surgical Technique. c. 2003 DePuy Spine, Inc., 28 pages.
Ebraheim, et al. "A Posterior Approach for Inspection of Reduction of Sacroiliac Joint Disruption." Surg. Radiol. Anat., 1999, 21(5), pp. 305-307.
Ebraheim, et al. "Anatomic considerations for Posterior Approach to the Sacroiliac Joint." Spine, 21(23), Dec. 1, 1996, pp. 2709-2712.
Garrido B.J. et al. Navigated placement of iliac bolts: description of a new technique. *The Spine Journal* 11 (2011) 331-335.
Giannikas, et al. "Sacroiliac Joint Fusion for Chronic Pain: A Simple Technique Avoiding the Use of Metalwork." Eur. Spine J, 13, 2004, pp. 253-256.
Globus Medical. REVERE® ADDITION® Sacroiliac Components, Surgical Technique. c. 2012 Globus Medical; 64 pages.
Globus Medical. SI-LOK™ Sacroiliac Joint Fixation System, Surgical Technique. c. 2011 Globus Medical, 44 pages.
Guner, et al. "Anterior Sacroiliac Fusion. A New Video-Assisted Endoscopic Technique." Surgical Laparoscopy & Endoscopy, 8(3), pp. 233-236.
LDR. Avenue® L Lateral Lumbar Cage. Sep. 2011, 3 pages.
LDR. ROI-A™ Anterior Approach Implant. Apr. 2008, 2 pages.
LDR. Surgical Technique ROI-C™ Anterior Cervical Cage. Apr. 2010, 15 pages.
Lee et al. Trajectory of Transsacral Iliac Screw for Lumbopelvic Fixation. *J Spinal Disord Tech* 2011;24(3):151-156.
Lehman, Jr. et al. Advantage of Pedicle Screw Fixation Directed Into the Apex of the Sacral Promontory Over Bicortical Fixation. *Spine* 2002;27(8):806-811.
Liebergall, Meir (Ifi) M.D., *Lumbosacral and Spinopelvic Fixation*, Lippincott-Raven, Philadelphia, PA, 1996, Chap. 48, "Sacroiliac Joint Fusion," pp. 611-618.
Luk et al. A Stronger Bicortical Sacral Pedicle Screw Fixation Through the S1 Endplate. *Spine* 2005;30(5):525-529.
Margulies, J.Y. et al., *Movement, Stability & Low Back Pain, The essential role of the pelvis*, Churchill Livingstone, London, 1997, Chapters 44-47, "Surgical Fusion of the Spine to the Sacrum, etc.," pp. 555-593.
Marotta N. et al. A novel minimally invasive presacral approach and instrumentation technique for anterior L5-S1 intervertebral disectomy and fusion. *Neurosurg Focus*, vol. 20, Jan. 2006, 8 pages.
Martin et al. Sacropelvic Fixation: Two Case Reports of a New Percutaneous Technique. *Spine* 2011;36(9):E618-21.
McLauchlan, et al. "Sacral and Iliac Articular Cartilage Thickness and Cellularity: Relationship to Subchondral Bone End-Plate Thickness and Cancellous Bone Density." Rheumatology 2002; 41:375-380.
Mendel et al. The Lateral Sacral Triangle—A Decision Support for Secure Transverse Sacroiliac Screw Insertion. *Injury J. Care Injured* 2010;42(2011):1164-1170.
Moshirfar et al. Pelvic Fixation in Spine Surgery. *The Journal of Bone & Joint Surgery* 2005;87-A(2 Suppl):89-106.
O'Brien et al. An Anatomic Study of the S2 Iliac Technique for Lumbopelvic Screw Placement. *Spine* 2009;34(12):E439-E442.
O'Brien et al. Feasibility of Minimally Invasive Sacropelvic Fixation. *Spine* 2010;35(4):460-464.
O'Brien et al. Sacropelvic Instrumentation: Anatomic and Biomechanical Zones of Fixation. *Seminars in Spine Surgery* 2004;16(2):76-90.
Ouellet et al. Surgical Anatomy of the Pelvis, Sacrum, and Lumbar Spine Relevant to Spinal Surgery. *Seminars in Spine Surgery* 2004 Elsevier Inc.;16:91-100.
Pan W. et al. The invention of an iliosacral screw fixation guide and its preliminary clinical application. *Orthopaedic Surgery* (2012), vol. 4, No. 1, pp. 55-59.
Puhakka, et al. "MR Imaging of the Normal Sacroiliac Joint with Correlation to Histology." Skeletal Radiol., 33, 2004, pp. 15-28.
SI-BONE iFuse Implant System, Surgical Technique Manual. c. 2011 SI-BONE, Inc., 35 pages.
SI-BONE iFuse Implant System™. SI-BONE, Inc. 2010, 4 pages.
Signus Medizintechnik GmbH. DIANA Operationstechnik. Rev. 2010-05/01, 20 pages.

(56) References Cited

OTHER PUBLICATIONS

Sponseller P.D. et al. Low profile pelvic fixation with the sacral alar iliac technique in the pediatric population improves results at two-year mninimum follow-up. *Spine* vol. 35, No. 20, pp. 1887-1892.
Stark J. G. et al. The history of sacroiliac joint arthrodesis: a critical review and introduction of a new technique. *Current Orthopaedic Practice*, vol. 22, No. 6, Nov./Dec. 2011, pp. 545-557.
Stark. "The Diagnosis and Treatment of Sacroiliac Joint Abnormalities." Current Orthopedic Practice, 21(4), Jul./Aug. 2010, pp. 336-347.
Synthes Spine. ProDisc-C Total Disc Replacement. Product Information. © 2008 Synthes, Inc., 14 pages.
Synthes Spine. SynFix-LR System. Instruments and implants for stand-alone anterior lumbar interbody fusion (ALIF). Technique Guide. © 2008 Synthes, Inc., 45 pages.
Synthes Spine. Universal Spinal System (USS) Polyaxial and Iliosacral Spine Fixation. A versatile system for posterior stabilization of spinal segments. Technique Guide, c. 2009 Synthes, Inc., 61 pages.
Szadek, et al. "Possible Nociceptive Structures in the Sacroiliac Joint Cartilage: An Immunohistochemical Study." Clinical Anatomy, 23, 2010, pp. 192-198.
Tenon Medical, *Catamaran SI Joint Implant*, http://tctig.com/projects (last visited Nov. 19, 2014).
Tifix® Technology Pressure Plate Technology: Multidirectional Locking Technology Titanium Plate and Screw Systems, General & Specific Instructions. litos/GmbH & Co. KG, Rev: Sep. 9, 2008.
Tobler W.D. et al. The presacral retroperitoneal approach for axial lumbar interbody fusion. *J Bone Joint Surg* [*Br*], vol. 93-B, No. 7, Jul. 2011, pp. 955-960.
Ugur, et al. "New Needle Holder Facilitates Percutaneous Fluoroscopy-Guided Sacroiliac Puncture." Acta Radiologica, 2006, 47(5), pp. 481-483.
Vanelderen, et al. "Evidence-Based Medicine. Evidence-Based Interventional Pain Medicine According to Clinical Diagnoses. 13. Sacroiliac Joint Pain." Pain Practice, 10(5), 2010, pp. 470-478.
Waisbrod, et al. "Sacroiliac Joint Arthrodesis for Chronic Lower Back Pain." Arch. Orthop. Trauma Surg., 106, 1987, pp. 238-240.
Wise, et al. "Minimally Invasive Sacroiliac Arthrodesis. Outcomes of a New Technique." Spinal Disord. Tech., 21(8), Dec. 2008, pp. 579-584.
Yin, et al. "Sensory Stimulation-Guided Sacroiliac Joint Radiofrequency Neurotomy: Technique Based on Neuroanatomy of the Dorsal Sacral Plexus." Spine, 28(20), pp. 2419-2425.
Zyga Technology, Inc. Slmmetry Sacroiliac Joint Fusion System, Surgeon Didactic, c. 2012 Zyga Technology, Inc., 45 pages.
Zyga Technology, Inc. Slmmetry Sacroiliac Joint Fusion System, Technique Guide, known at least as early as Mar. 1, 2013, 20 pages.
Advisory Action, U.S. Appl. No. 12/998,712, dated Jan. 28, 2014, 4 pages.
Advisory Action, U.S. Appl. No. 13/135,381, mailed Jul. 23, 2013, 3 pages.
Appeal Brief, U.S. Appl. No. 13/135,381, dated Dec. 23, 2013, 20 pages.
European Search Report, EP Appl. No. 11733183.5, dated Dec. 18, 2013, 4 pages.
European Search Report, EP Appl. No. 12799773.2, dated Oct. 29, 2014.
Examination Report, SG Application No. 201205104-1, dated Jul. 17, 2014, Intellectual Property Office of Singapore.
Final Rejection, U.S. Appl. No. 12/998,712, mailed Nov. 7, 2013, 24 pages.
Final Rejection, U.S. Appl. No. 13/135,381, mailed May 9, 2013, 14 pages.
International Search Report and Written Opinion, PCT application No. PCT/US2012/042823, dated Nov. 5, 2012, 16 pages.
International Search Report and Written Opinion, PCT Application No. PCT/US2012/055892, dated Mar. 25, 2013, 22 pages.
International Search Report and Written Opinion, PCT application No. PCT/US2011/000070, dated Mar. 21, 2011, 13 pages.
International Search Report and Written Opinion, PCT Application No. PCT/US2013/051381, dated Nov. 4, 2013, 16 pages.
International Search Report and Written Opinion, PCT/US2014/030889, dated Jul. 16, 2014.
International Search Report and Written Opinion, PCT/US2014/048990, dated Nov. 18, 2014.
Japanese Office Action, JP2012-548960, dated Oct. 7, 2014.
Non-Final Office Action, U.S. Appl. No. 12/998,712, mailed May 31, 2013, 44 pages.
Non-Final Office Action, U.S. Appl. No. 12/998,712, dated Aug. 1, 2014.
Non-Final Office Action, U.S. Appl. No. 13/135,381, mailed Nov. 5, 2012, 19 pages.
Non-Final Office Action, U.S. Appl. No. 13/236,411, dated Apr. 11, 2014.
Notice of Allowance, U.S. Appl. No. 13/135,381, dated Apr. 17, 2014.
Response to Advisory Action, U.S. Appl. No. 13/135,381, filed Aug. 20, 2013, 12 pages.
Response to Final Office Action, U.S. Appl. No. 12/998,712, dated Jan. 7, 2014, 16 pages.
Response to Final Office Action, U.S. Appl. No. 13/135,381, filed Jul. 9, 2013, 11 pages.
Response to Non-Final Office Action, U.S. Appl. No. 13/135,381, filed Feb. 4, 2013, 7 pages.
Response to Non-Final Office Action, U.S. Appl. No. 12/998,712, filed Aug. 28, 2013, 17 pages.
Response to Non-Final Office Action, U.S. Appl. No. 12/998,712, dated Sep. 4, 2014.
Response to Non-Final Office Action, U.S. Appl. No. 13/236,411, dated Sep. 11, 2014.
Response to Restriction, U.S. Appl. No. 13/236,411, filed Jun. 10, 2013, 13 pages.
Response to Restriction, U.S. Appl. No. 13/236,411, filed Nov. 12, 2013, 14 pages.
Response to Restriction, U.S. Appl. No. 13/945,053, dated Nov. 19, 2014.
Restriction Requirement, U.S. Appl. No. 13/236,411, mailed May 10, 2013, 5 pages.
Restriction Requirement, U.S. Appl. No. 13/236,411, mailed Oct. 16, 2013, 7 pages.
Restriction Requirement, U.S. Appl. No. 13/945,053, dated Sep. 25, 2014.
Singapore Search Report and Written Opinion, SG Appl. No. 201205104-1, dated Oct. 31, 2013, 29 pages.
Supplemental Amendment, U.S. Appl. No. 12/998,712, dated Apr. 14, 2014, 14 pages.
Amendment Under 1.312, U.S. Appl. No. 13/475,695, dated Mar. 25, 2016.
Amendment Under 1.312, U.S. Appl. No. 13/945,053, dated May 19, 2016.
Amendment Under 1.312, U.S. Appl. No. 13/946,790, dated Dec. 14, 2015.
Final Office Action, U.S. Appl. No. 14/216,975, dated Dec. 30, 2016.
Final Rejection, U.S. Appl. No. 13/236,411, dated Jan. 2, 2015.
Final Rejection, U.S. Appl. No. 13/945,053, dated Dec. 22, 2015.
Non-Final Office Action, U.S. Appl. No. 13/945,053, dated Apr. 3, 2015.
Non-Final Office Action, U.S. Appl. No. 13/475,695, dated Jul. 30, 2015.
Non-Final Office Action, U.S. Appl. No. 14/127,119, dated Sep. 8, 2016.
Non-Final Office Action, U.S. Appl. No. 14/216,975, dated Jun. 20, 2016.
Non-Final Office Action, U.S. Appl. No. 14/344,876, dated Dec. 1, 2016.
Non-Final Office Action, U.S. Appl. No. 14/413,318, dated May 3, 2016.
Non-Final Office Action, U.S. Appl. No. 14/567,956, dated Feb. 12, 2016.

(56) References Cited

OTHER PUBLICATIONS

Non-Final Office Action, U.S. Appl. No. 14/681,882, dated Oct. 6, 2016.
Notice of Allowance, U.S. Appl. No. 13/236,411, dated Mar. 16, 2015.
Notice of Allowance, U.S. Appl. No. 12/998,712, dated Dec. 23, 2014.
Notice of Allowance, U.S. Appl. No. 13/475,695, dated Feb. 18, 2016.
Notice of Allowance, U.S. Appl. No. 13/945,053, dated Mar. 28, 2016.
Notice of Allowance, U.S. Appl. No. 13/945,053, dated Jul. 5, 2016.
Notice of Allowance, U.S. Appl. No. 13/946,790, dated Nov. 20, 2015.
Notice of Allowance, U.S. Appl. No. 13/946,790, dated Feb. 16, 2016.
Notice of Allowance, U.S. Appl. No. 14/413,318, dated Aug. 31, 2016.
Notice of Allowance, U.S. Appl. No. 14/567,956, dated Sep. 13, 2016.
Response to Final Office Action, U.S. Appl. No. 13/236,411, dated Mar. 4, 2015.
Response to Non-Final Office Action, U.S. Appl. No. 13/475,695, dated Oct. 30, 2015.
Response to Non-Final Office Action, U.S. Appl. No. 13/945,053, dated Aug. 31, 2015.
Response to Non-Final Office Action, U.S. Appl. No. 14/413,318, dated Aug. 3, 2016.
Response to Non-Final Office Action, U.S. Appl. No. 14/567,956, dated May 10, 2016.
Response to Non-Final Office Action, U.S. Appl. No. 14/681,882, dated Jan. 5, 2017.
Response to Restriction, U.S. Appl. No. 13/946,790, dated Sep. 14, 2015.
Response to Restriction, U.S. Appl. No. 13/475,695, dated Jun. 30, 2015.
Response to Restriction, U.S. Appl. No. 14/127,119, dated Jun. 6, 2016.
Response to Restriction, U.S. Appl. No. 14/216,975, dated Jan. 22, 2016.
Response to Restriction, U.S. Appl. No. 14/344,876, dated Aug. 29, 2016.
Response to Restriction, U.S. Appl. No. 14/413,318, dated Apr. 19, 2016.
Response to Restriction, U.S. Appl. No. 14/514,221, dated Oct. 24, 2016.
Response to Restriction, U.S. Appl. No. 14/567,956, dated Jan. 19, 2016.
Restriction Requirement, U.S. Appl. No. 13/475,695, dated Mar. 30, 2015.
Restriction Requirement, U.S. Appl. No. 13/946,790, dated Jul. 14, 2015.
Restriction Requirement, U.S. Appl. No. 14/127,119, dated Apr. 5, 2016.
Restriction Requirement, U.S. Appl. No. 14/216,975, dated Oct. 23, 2015.
Restriction Requirement, U.S. Appl. No. 14/413,318, dated Feb. 19, 2016.
Restriction Requirement, U.S. Appl. No. 14/514,221, dated Aug. 25, 2016.
Restriction Requirement, U.S. Appl. No. 14/567,956, dated Nov. 20, 2015.
Restriction Requirement, U.S. Appl. No. 14/723,384, dated Dec. 29, 2016.
Non-Final Office Action, U.S. Appl. No. 15/178,244, dated May 16, 2017.
Non-Final Office Action, U.S. Appl. No. 15/178,291, dated May 16, 2017.
Notice of Allowance, U.S. Appl. No. 14/127,199, dated Apr. 21, 2017.
Notice of Allowance, U.S. Appl. No. 14/216,975, dated Apr. 5, 2017.
Notice of Allowance, U.S. Appl. No. 14/567,956, dated Mar. 13, 2017.
Notice of Allowance, U.S. Appl. No. 14/681,882, dated May 10, 2017.
Response to Final Office Action, U.S. Appl. No. 14/216,975, dated Feb. 27, 2017.
Response to Non-Final Office Action, U.S. Appl. No. 14/344,876, dated Mar. 1, 2017.

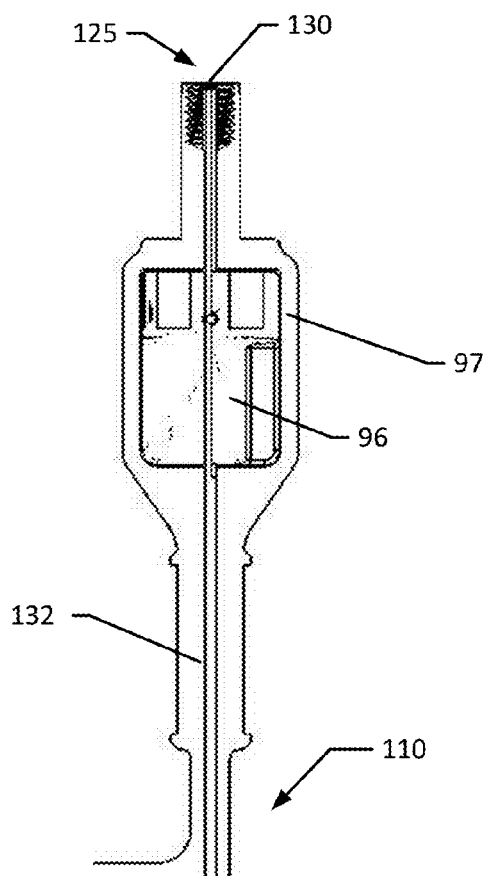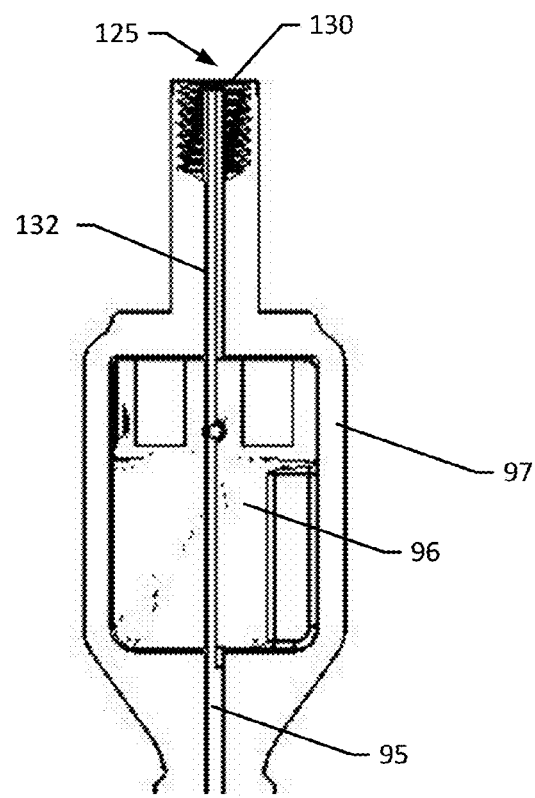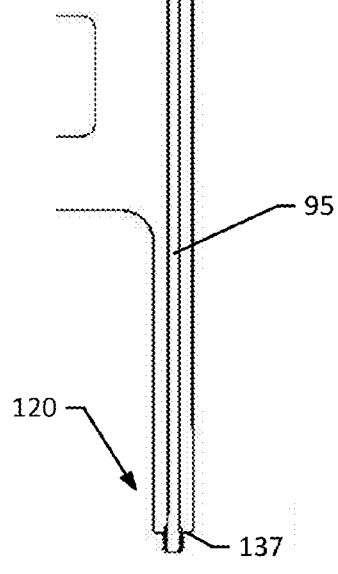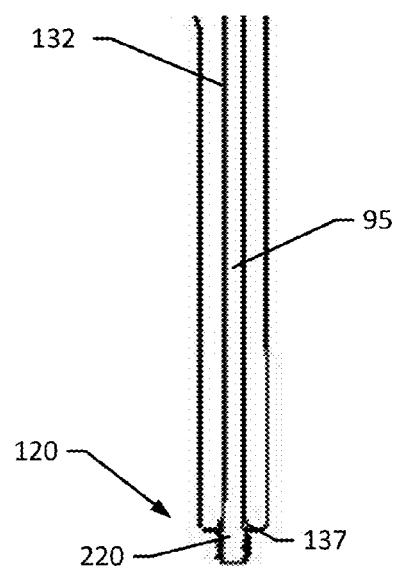
FIG. 19A  FIG. 19B  FIG. 19C

SYSTEMS FOR AND METHODS OF FUSING A SACROILIAC JOINT

CROSS-REFERENCE TO RELATED APPLICATIONS

The present application claims priority to U.S. Provisional Patent Application 61/914,409, filed Dec. 11, 2013, and entitled "SYSTEMS FOR AND METHODS OF FUSING A SACROILIAC JOINT," which is hereby incorporated by reference in its entirety into the present application.

The present application also claims priority to U.S. Provisional Patent Application 61/860,185, filed Jul. 30, 2013, and entitled "SYSTEMS FOR AND METHODS OF FUSING A SACROILIAC JOINT," which is hereby incorporated by reference in its entirety into the present application.

The present application also claims priority to U.S. Provisional Patent Application 61/955,126, filed Mar. 18, 2014, and entitled "SACROILIAC JOINT IMPLANT," which is hereby incorporated by reference in its entirety into the present application.

The present application also claims priority to U.S. Provisional Patent Application 61/979,857, filed Apr. 15, 2014, and entitled "SACROILIAC JOINT IMPLANT," which is hereby incorporated by reference in its entirety into the present application.

TECHNICAL FIELD

Aspects of the present disclosure relate to medical systems, devices, and methods for treating a sacroiliac joint. In particular, aspects of the present disclosure relate to systems, devices, and methods involving a sacroiliac joint implant for non-transverse placement between articular surfaces of a sacroiliac joint to dispose a sacrum and an ilium in a substantially immobilized relation.

BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis, an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods encompassing an anterior approach, a posterior approach, and a lateral approach with or without percutaneous screw or other type implant fixation. However, while each of these methods has been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint including the anterior approach, posterior approach, or lateral approach may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery.

A danger to open surgery using the anterior approach can be damage to the L5 nerve root, which lies approximately two centimeters medial to the sacroiliac joint or damage to the major blood vessels. Additionally, these procedures typically involve fixation of the sacroiliac joint (immobilization of the articular surfaces of the sacroiliac joint in relation to one another) by placement of one or more screws or one or more trans-sacroiliac implants or by placement of implants into the S1 pedicle and iliac bone.

Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult, requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to mal-placement of implants leading to damage of surrounding structures. Additionally, these procedures are often performed without fusion of the sacroiliac joint, which does not remove the degenerative joint surface and thereby does not address the degenerative condition of the sacroiliac joint, which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen, which can be of relatively large dimension and which are subsequently broached with instruments, which can result in bone being impacted into the pelvis and neuroforamen.

The creation of the trans-sacroiliac bores and subsequent broaching of the bores requires a guide pin, which may be inadvertently advanced into the pelvis or sacral foramen, resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint, which may result in continued or recurrent pain requiring additional surgery.

Another substantial problem with conventional procedures can be that placement of posterior extra-articular distracting fusion implants and bone grafts may be inadequate with respect to removal of the articular surface or preparation of cortical bone, the implant structure and fixation of the sacroiliac joint. The conventional procedures may not remove sufficient amounts of the articular surfaces or cortical surfaces of the sacroiliac joint to relieve pain in the sacroiliac joint. The conventional implant structures may have insufficient or avoid engagement with the articular surfaces or cortical bone of the sacroiliac joint for adequate fixation or fusion. The failure to sufficiently stabilize and fuse the sacroiliac joint with the conventional implant structures and methods may result in a failure to relieve the condition of sacroiliac joint being treated. Additionally, conventional methods of driving apart a sacrum and ilium may lead to mal-alignment of the sacroiliac joint and increased pain.

The inventive sacroiliac fusion system described herein addresses the problems associated with conventional methods and apparatuses used in fixation and fusion of the sacroiliac joint.

BRIEF SUMMARY

In one aspect, an implant assembly for the fusion of a sacroiliac joint of a subject is provided. The implant assembly may include an implant that includes: 1) an intra-articular element extending an implant length between an implant proximal end and an implant distal end, and further extending an implant height between an implant upper edge and an opposed implant lower edge; and 2) an anchor that includes a proximal anchor end and a distal anchor end. The proximal anchor end and the distal anchor end are positioned on opposite sides of a plane coincident with the first articular face or coincident with the second articular face. The intra-articular element may include: 1) a first articular face and an opposed second articular face extending the implant height and at least a portion of the implant length; 2) a graft window formed within at least a portion of the intra-articular element and extending through the intra-articular element from the first articular face to the second articular face; and 3) at least one keel attached to the intra-articular element along at least a portion of the implant length. The intra-articular element is configured for implantation within a joint space of the sacroiliac joint with the first and second articular faces contacting articular surfaces of the sacroiliac joint. The anchor is configured for insertion transversely across the joint space of the sacroiliac joint. Each keel of the at least one keels may project essentially perpendicularly outward from the first articular face and from the second articular face, ending in a first edge and a opposite second edge separated by a keel width. The first edge and the second edge may be in parallel alignment along the implant length. The first edge and the second edge may distally converge toward one another. The at least one keel may include a first keel extending from the implant proximal end to the implant distal end. The first keel may be attached along the implant upper edge or the implant lower edge. The at least one keel may further include a second keel extending from the implant proximal end to the implant distal end. The second keel may be attached along the implant upper edge or the implant lower edge opposite to the first keel. The keel width of the first keel may be equal to the keel width of the second keel. The keel width of the first keel may be larger than the keel width of the second keel. The at least one keel may include a first keel extending from the implant proximal end to the implant distal end. The first keel may be attached to the intra-articular element between the implant upper edge and the implant lower edge.

The first keel may further include a keel gap extending over an intersection of the first keel with the graft window. The graft window may extend through the intra-articular element along a window axis forming an angle ranging from about 45 degrees to about 90 degrees relative to a plane parallel to the first articular face or the second articular face. The graft window may further comprises a window length extending along a portion of the implant length, the portion ranging from about 40% to about 70% of the implant length.

The window length may be situated between the implant proximal end and the implant distal end. One end of the window length may be coincident with the implant distal end. The anchor may pass through the graft window. The anchor may pass outside of the implant above the upper edge or below the lower edge. The intra-articular element may further include: 1) a proximal face situated at the implant proximal end; and 2) a threaded bore extending from the proximal face along the implant length toward the implant distal end and opening distally into the graft window. The at least one keel and the intra-articular element may taper distally into a distal edge situated at the implant distal end. The implant length may range from about 20 mm to about 50 mm. The implant height may range from about 10 mm to about 20 mm. An intra-articular thickness between the first articular face and the second articular face may range from about 5 mm to about 7 mm. The keel width may range from about 10 mm to about 20 mm.

In another aspect, a sacroiliac joint fusion system is provided that may include: a) a joint implant that may include a longitudinal axis extending between a proximal end and a distal end of the joint implant; and a first bore extending non-parallel to the longitudinal axis; b) an anchor element configured to be received in the first bore; and c) a delivery tool. The delivery tool may include: i) an implant arm that may include a shaft extending between a proximal end and a distal end of the implant arm and a handle at the proximal end, the distal end of the implant arm configured to releasably couple to the proximal end of the joint implant; and ii) an anchor arm rotatably coupled to the implant arm at a first end. The anchor arm may include an anchoring guide at a second end configured to align the anchor element in a trajectory such that the anchor element will be received within the first bore when the anchor element is guided by the anchoring guide. Relative rotation of the anchor arm about a longitudinal axis of the implant arm may be limited to trajectories of the anchor element that are configured to align the anchor element within the first bore. A final manufactured configuration of the delivery tool and the joint implant may be such that, when the system is assembled such that the implant arm may be releasably coupled to the joint implant, a delivery arrangement automatically exists such that the anchor arm is oriented to align the trajectory of the anchor element and to deliver the anchor element within the first bore. The rotation of the anchor arm relative to the implant arm may be limited to about 60 degrees of rotation. The first bore may extend through a pair of planar faces that are opposite of each other. The pair of planar faces may define a first plane therein that also extends in a direction of the longitudinal axis of the joint implant. The first plane may be substantially perpendicular to a second plane defined by the implant arm and the anchor arm in a neutral position. The neutral position may orient the anchor element substantially perpendicularly to the first plane. The about 60 degrees of rotation may include about 30 degrees of rotation of the second plane relative to the first plane on either side of the neutral position. The rotation of the anchor arm relative to the implant arm may be limited to less than 360 degrees of rotation. The rotation of the anchor arm relative to the implant arm may be limited to less than 180 degrees of rotation. The relative rotation of the anchor arm about a longitudinal axis of the implant arm may be limited by a cam mechanism within a channel. The implant arm may include the cam mechanism and the anchor arm may include the channel. The cam mechanism may include a cam-shape that may be configured to only partially rotate within the channel. The cam mechanism may be slidably coupled within the channel.

In an additional aspect, a sacroiliac joint fusion system is provided that may include: a) a joint implant that may include a longitudinal axis extending between a proximal end and a distal end of the joint implant and a first bore extending non-parallel to the longitudinal axis; b) an anchor element configured to be received in the first bore; and c) a delivery tool. The delivery tool may include: i) an implant arm that may include a shaft extending between a proximal end and a distal end of the implant arm and a handle at the proximal end; and ii) an anchor arm. The distal end of the implant arm may be configured to releasably couple to the proximal end of the joint implant. The anchor arm may include an anchor guide coupled to the implant arm via a distal articulating member and a proximal articulating member. The distal articulating member may be rotatably coupled with the implant arm at a first end and rotatably coupled with the anchor guide at a second end. The proximal articulating member may be slidably coupled with the implant arm at a third end and configured to slidably translate distal-proximal along the shaft of the implant arm. The proximal articulating member may be rotatably coupled with the anchor guide at a fourth end. The anchor guide may be configured to align the anchor element in a trajectory such that the anchor element will be received within the first bore when the anchor element is guided by the anchor guide. When the third end of the proximal articulating member is positioned in a proximal-most position, the anchor guide is configured to align the anchor element in the trajectory. When the third end of the proximal articulating member is positioned in a distal-most position, the anchor guide may be configured to align the anchor element in the trajectory. A final manufactured configuration of the delivery tool and the joint implant are such that, when the system is assembled such that the implant arm is releasably coupled to the joint implant, a delivery arrangement may automatically exist such that the anchor arm is oriented to align the trajectory of the anchor element and to deliver the anchor element within the first bore. The first end may be positioned distally of the third end on the implant arm. The second end may be positioned distally of the fourth end on the anchor guide. The implant arm may further include an actuation assembly configured to releasably couple and decouple with the joint implant. The actuation assembly may be rotationally actuated. An angle of the trajectory relative to the longitudinal axis of the joint implant may be different when the third end is in the proximal-most position and the distal-most position. When the third end is in the proximal-most position, an angle between the trajectory and a longitudinal axis of the shaft of the implant arm may be about 34 degrees. When the third end is in the distal-most position, an angle between the trajectory and a longitudinal axis of the shaft of the implant arm may be about 45 degrees. The first end of the distal articulating member may include a stop feature that inhibits rotation of the first end beyond a certain point. The stop feature may be configured to contact the shaft of the implant arm when the third end of the proximal articulating member is in the proximal-most position.

In another additional aspect, a sacroiliac joint fusion system is provided that may include: a) a joint implant; b) an anchor element configured to be received in a first bore; and c) a delivery tool. The joint implant may include: a longitudinal axis extending between a proximal end and a distal end of the joint implant; and the first bore extending non-parallel to the longitudinal axis. The delivery tool may include: i) an implant arm that may include a shaft extending between a proximal end and a distal end of the implant arm and a handle at the proximal end; and ii) an anchor arm rotatably coupled to the implant arm via a rotatable joint at a first end. The distal end of the implant arm may be configured to releasably couple to the proximal end of the joint implant. The anchor arm may include an anchoring guide at a second end that is configured to align the anchor element in a first trajectory such that the anchor element will be received within the first bore when the anchor element is guided by the anchoring guide. The rotatable joint may be configured to limit rotation of the anchor arm to predefined trajectories of the anchor element that are configured to align the anchor element within the first bore, a final manufactured configuration of the delivery tool and the joint implant may be such that, when the system is assembled such that the implant arm is releasably coupled to the joint implant, a delivery arrangement automatically exists such that the anchor arm is oriented to align the first trajectory of the anchor element and to deliver the anchor element within the first bore. A first angle may be defined between the shaft of the implant arm and the anchor arm, and rotation of the anchor arm relative to the implant arm may be limited to varying of only the first angle. A relative decrease of the first angle may cause the anchor element to angle towards a proximal portion of the first bore; a relative increase in the first angle may cause the anchor element to angle towards a distal portion of the first bore. Rotation of the anchor arm may be limited to rotation about a longitudinal axis of the implant arm. The anchoring guide may include a plurality of laterally offset guides, and each of the plurality of laterally offset guides may be configured to align a unique trajectory of an anchoring element. The plurality of laterally offset guides may include a first, a second, and a third guide. The first guide may align a trajectory of a first anchoring element dorsal to the joint implant. The second guide may align a trajectory of a second anchoring element within the first bore. The third guide may align a trajectory of a third anchoring element ventral to the joint implant. The system may further include an auxiliary guide arm rotatably coupled to the implant arm at a third end. The auxiliary guide arm may include an auxiliary guide at a fourth end that is configured to align an auxiliary element in a second trajectory such that the auxiliary element will be delivered along the second trajectory when guided by the auxiliary guide. The auxiliary guide arm may be configured to adjust in at least one degree of freedom. The auxiliary element may be a needle. The joint implant may define an I-beam shaped cross-section having a top keel, a bottom keel, and an intra-articular element extending between and coupling the top keel and the bottom keel. The first bore may extend through the intra-articular element.

While multiple embodiments are disclosed, still other embodiments of the present disclosure will become apparent to those skilled in the art from the following detailed description, which shows and describes illustrative embodiments of the disclosure. As will be realized, the disclosure is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The following figures illustrate various aspects of the disclosure.

FIG. 19A is a side cross-sectional view of an implant arm.

FIG. 19B is a side cross-sectional view of a proximal end of an implant arm.

FIG. 19C is a side cross-sectional view of a distal end of an implant arm.

Corresponding reference characters and labels indicate corresponding elements among the views of the drawings. The headings used in the figures should not be interpreted to limit the scope of the claims.

DETAILED DESCRIPTION

Figure 1:
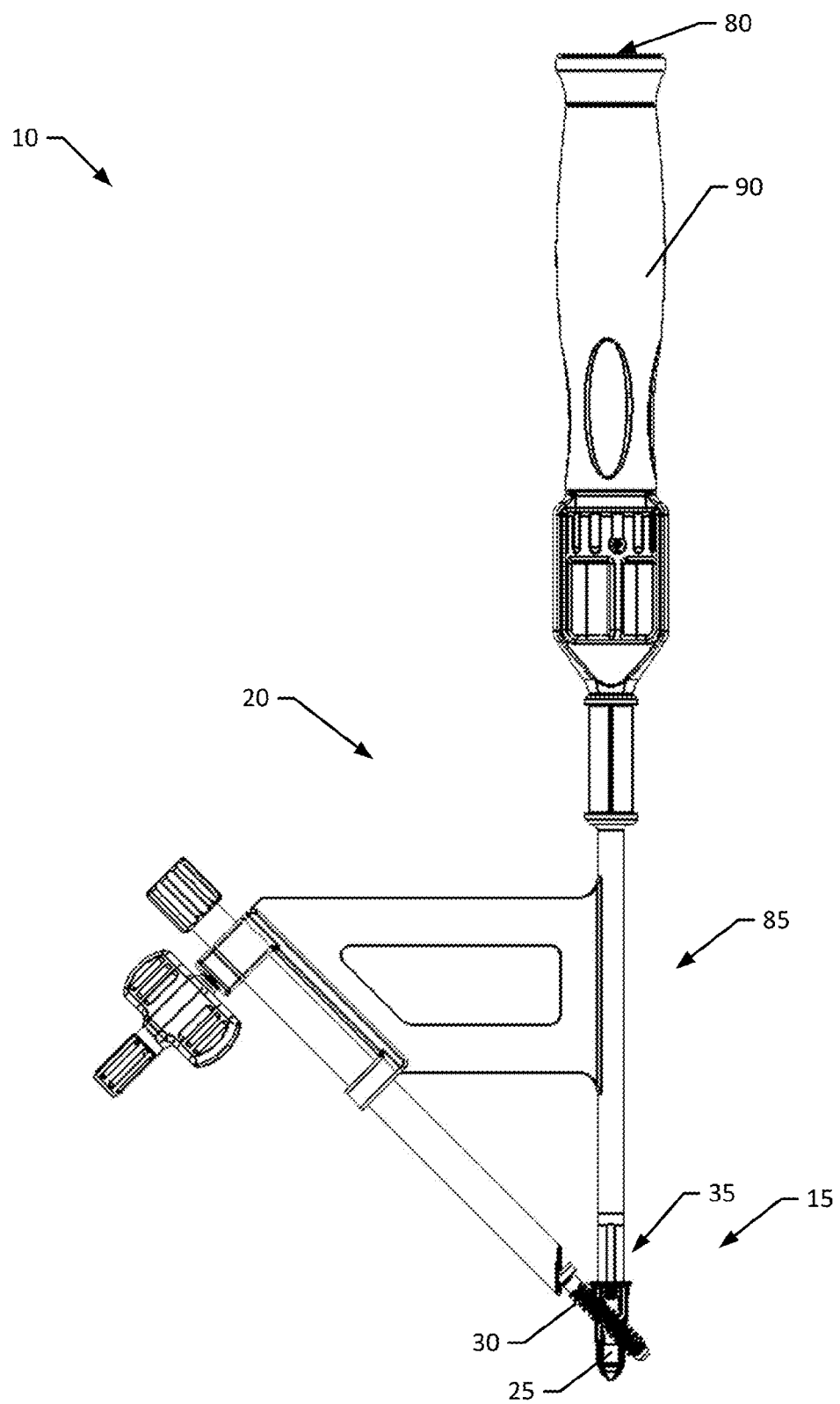
FIG. 1 is side view of the implant assembly mounted on a delivery tool.

Implementations of the present disclosure involve a system for fusing a sacroiliac joint. Referring to FIG. 1, the system 10 includes a delivery tool 20 and an implant assembly 15 delivered to a sacroiliac joint (not shown) via the delivery tool 20. The implant assembly 15 may include an implant 25 and an anchor 30 configured to fuse the sacroiliac joint once implanted at the joint. The elements of the delivery tool 20 are arranged and configured to quickly, accurately and reliably deliver the anchor 30 through a graft window (not shown) formed within the implant 25. The implant 25 is supported off of a distal end 35 of the delivery tool 20, thereby maintaining the implant 25 and the anchor 30 in an appropriate alignment relative to the anatomical features of the sacroiliac joint region as well as to one another. The alignment of the implant 25 and anchor 30 provided by the delivery tool 20 may reduce the potential for injury of sensitive tissues including, but not limited to, nerve tissue and vascular tissue. The alignment of the anchor 30 and implant 25 provided by the delivery tool 20 may further quickly, accurately, and reliably prevent mechanical interference between the implant 25 and anchor 30 during blind insertion of the anchor 30 during a surgical implantation procedure.

I. Implant Assembly

Figure 2:
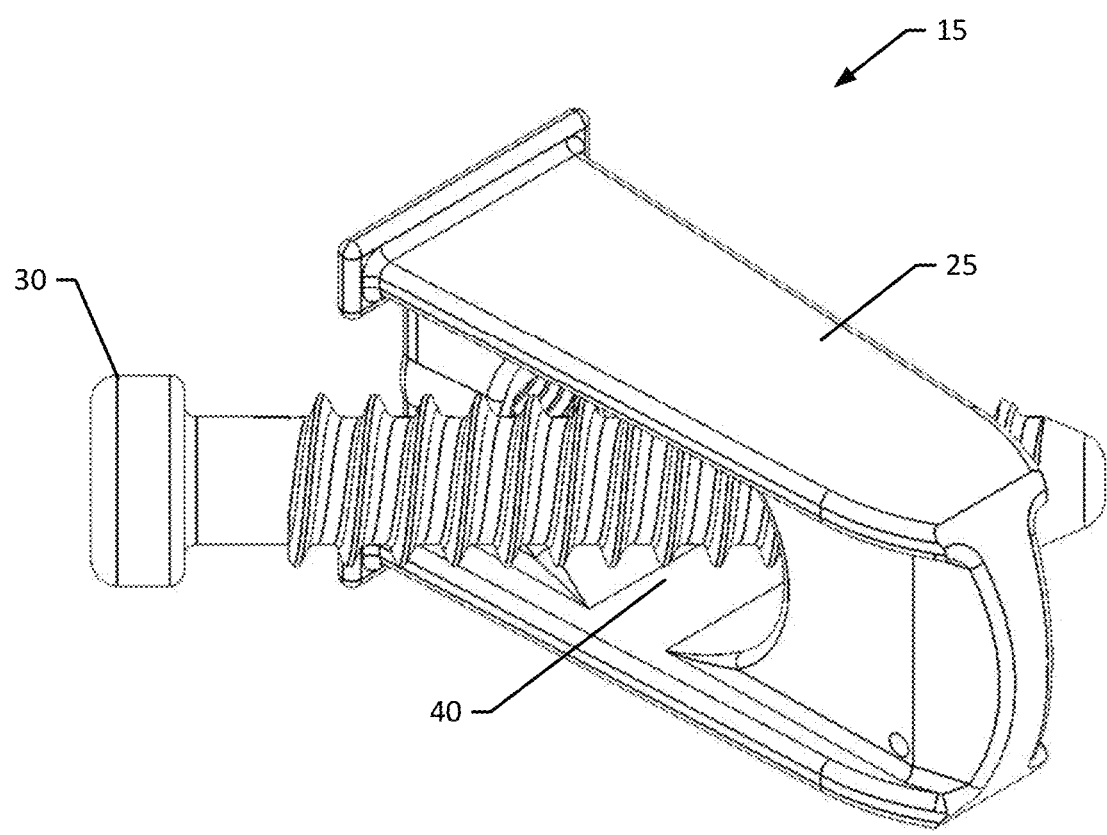
FIG. 2 is a side isometric view of an anchor and an implant of an implant assembly.

To begin a detailed discussion of components of an implant assembly 15, reference is made to FIG. 2, a side isometric view of the implant assembly 15. The implant assembly 15 may include an implant 25 and an anchor 30 in various aspects. The implant 25 may further include a graft window 40 formed within the implant 25 through which the anchor 30 may be inserted in an aspect.

Figure 3:
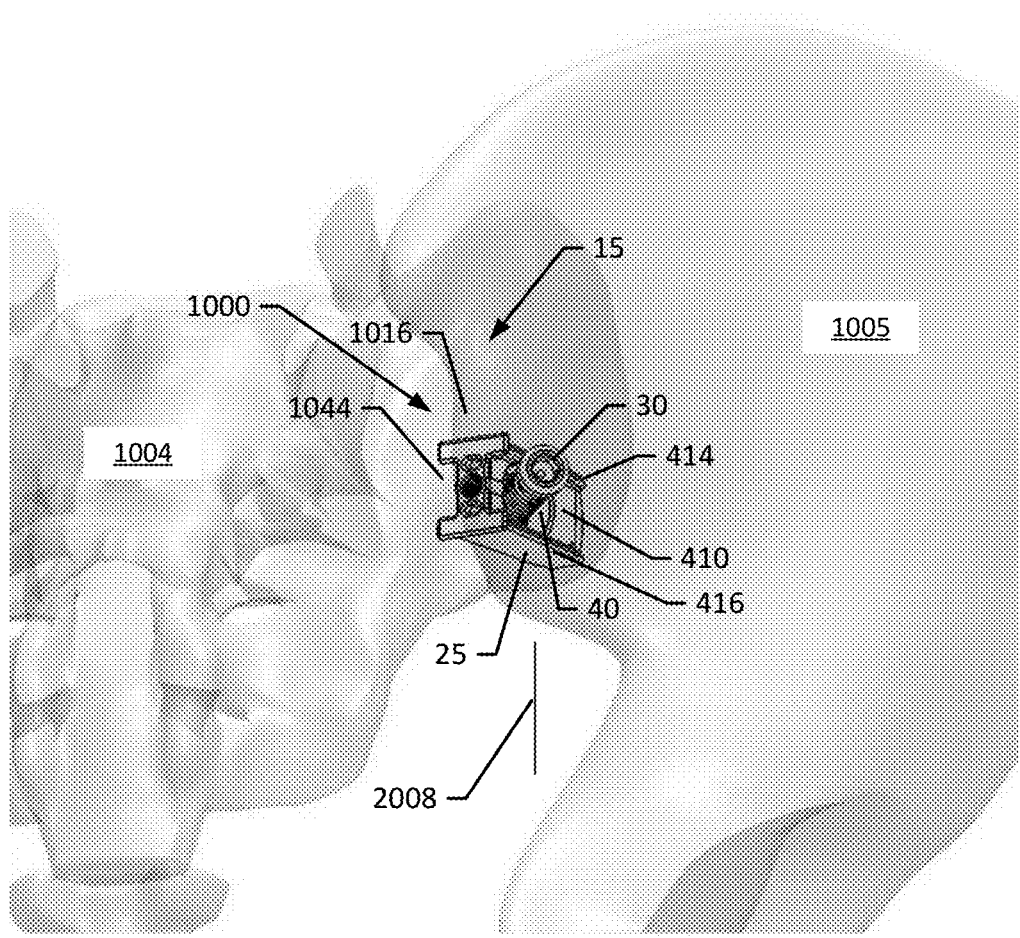
FIG. 3 is a posterior view of an anchor and an implant secured within a sacroiliac joint of a subject.

Referring to FIG. 3, the implant assembly 15 may be implanted to stabilize a sacroiliac joint 1000 in one aspect. The implant 25 of the implant assembly 15 may be situated in a non-transverse placement within the sacroiliac joint space 1044 between the articular surfaces 1016 of the sacroiliac joint 1000. The anchor 30 typically extends through the ilium 1005 and graft window 40 of the implant 25 and into the sacrum 1004 in a trajectory characterized as generally transverse to the sacroiliac joint 1000 and implant 25. In this transverse trajectory, the anchor 30 may draw the ilium 1005 and sacrum 1004 together about the implant 25, thereby enhancing the robust fixation of the implant 25 within the sacroiliac joint space 1044 by compressing the articular surfaces 1016 of the sacroiliac joint 1000 against the external surfaces of the implant 25. With the implant 25 securely implanted in the sacroiliac joint 1000, the articular surfaces 1016 may fuse together about the implant 25 as well as across the graft window 40 of the implant 25.

In various other aspects (not shown) the implant assembly 15 may further include one or more additional anchors inserted along additional trajectories to further enhance the fixation of the implant 25 within the sacroiliac joint space 1044. In other additional aspects, the anchor 30 and/or an additional anchor may be directed in an offset trajectory that is generally transverse to the sacroiliac joint 1000, but offset from the trajectory illustrated in FIG. 3 such that the anchor 30 passes above (cranially) or below (caudally) the implant 25. By way of non-limiting example, this offset trajectory may be used to draw the ilium 1005 and sacrum 1004 together about the implant 25 when the design of the graft window 40 of the implant 25 precludes insertion of the anchor 30 through the implant 25.

a. Implant

Referring again to FIG. 3, the implant assembly 15 includes an implant 25 for non-transverse placement between articular surfaces 1016 of a sacroiliac joint 1000 to dispose a sacrum 1004 and an ilium 1005 in a substantially immobilized relation.

Figure 4A:
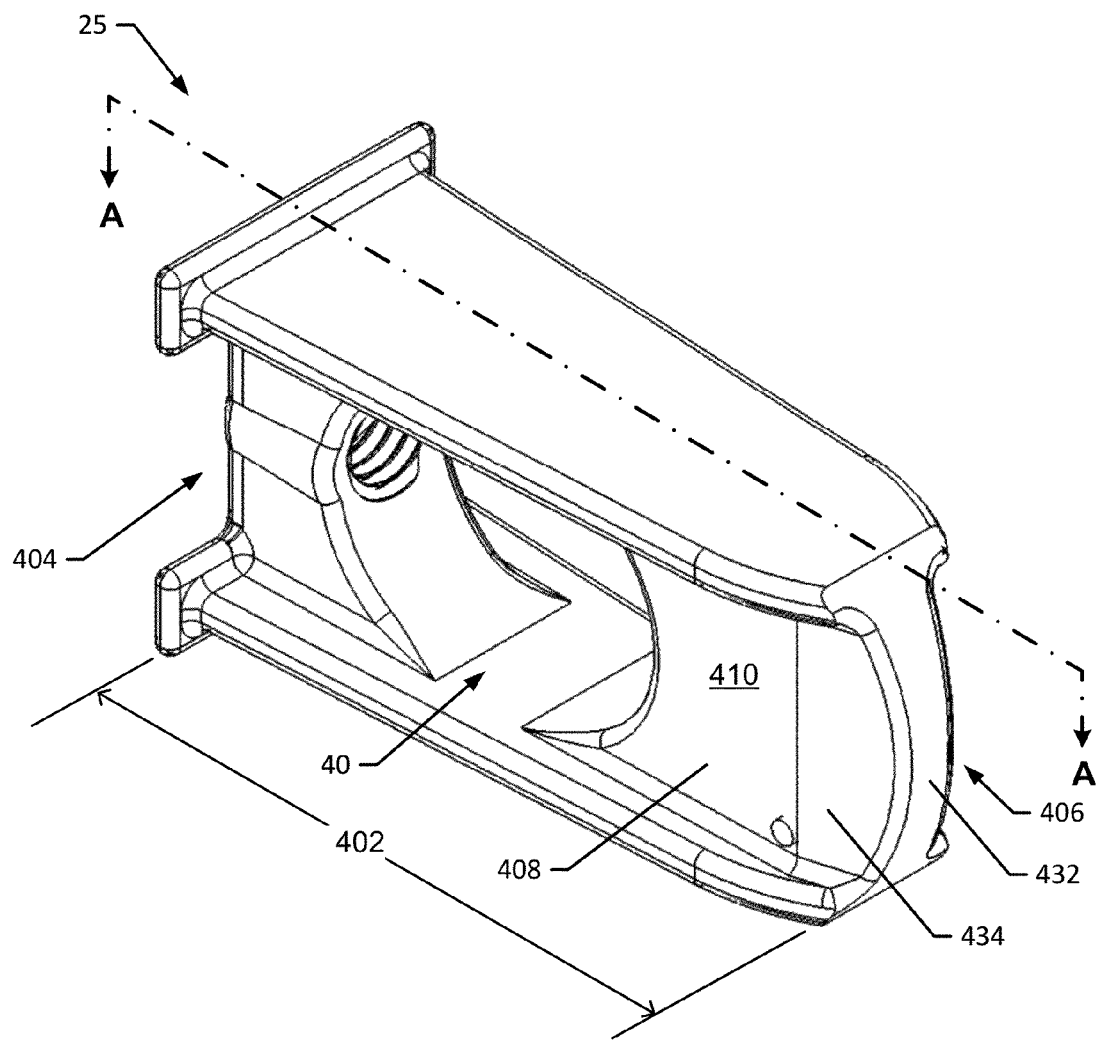
FIG. 4A is a side isometric view of an implant.
Figure 4B:
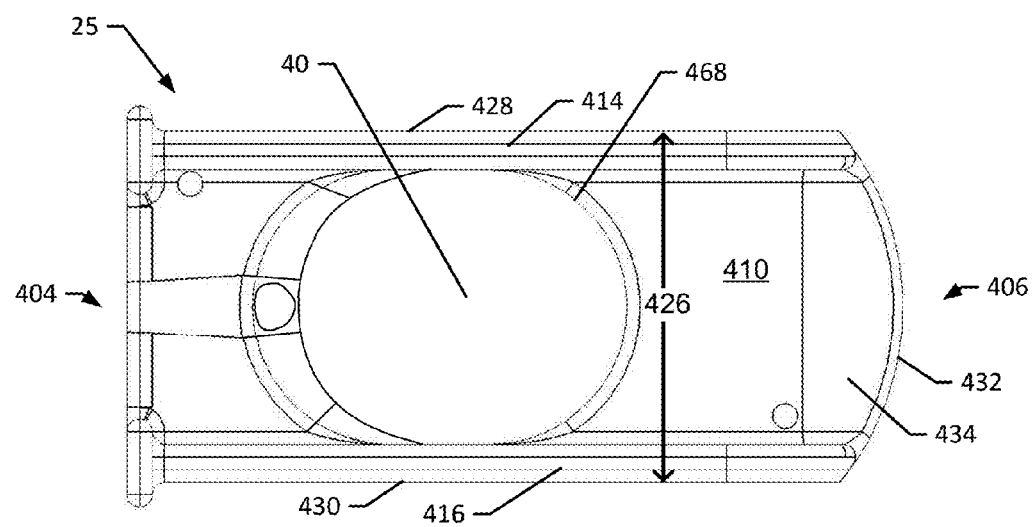
FIG. 4B is a side view of an implant.
Figure 4C:
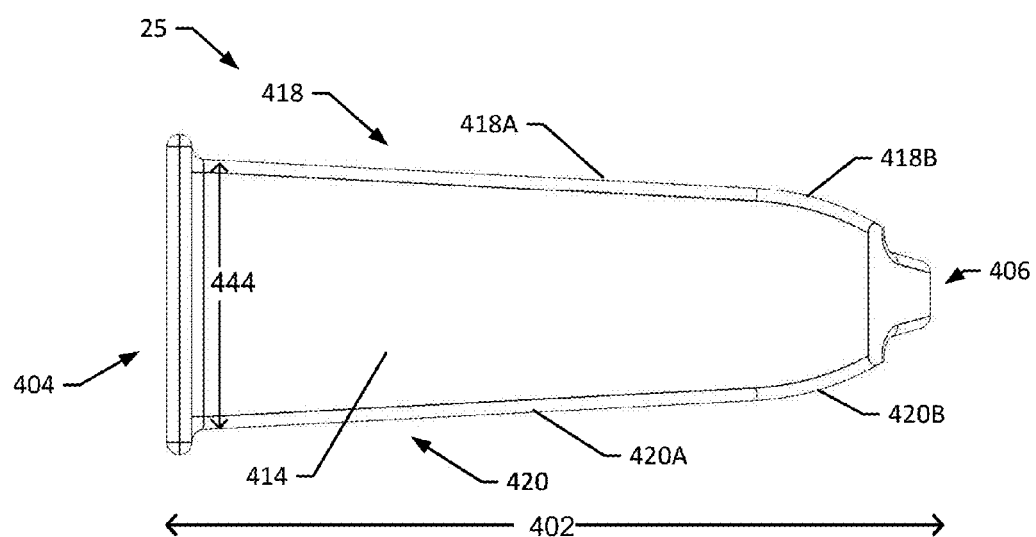
FIG. 4C is a top view of an implant.
Figure 4D:
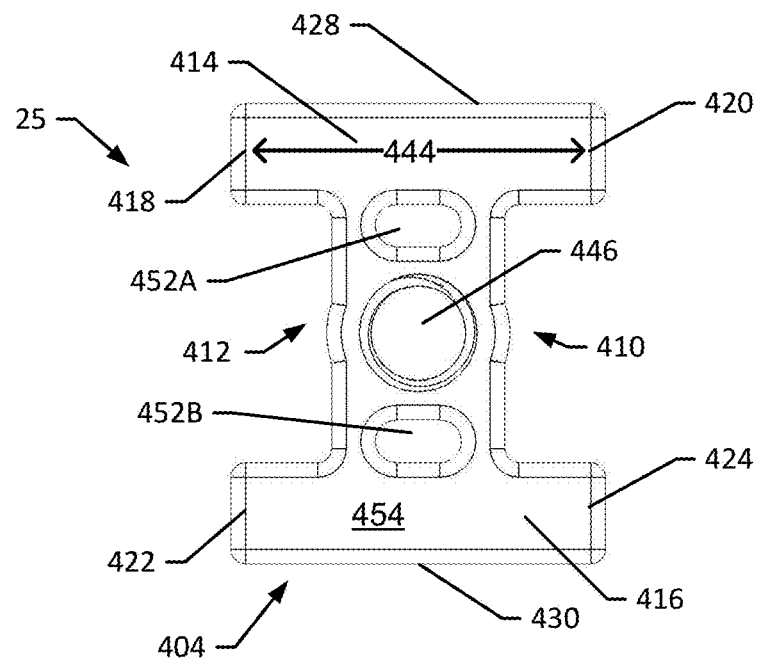
FIG. 4D is a proximal view of an implant.
Figure 4E:
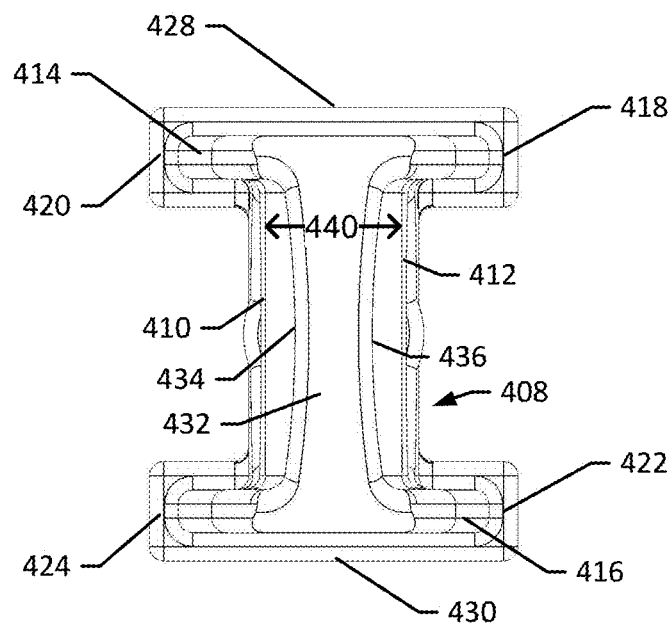
FIG. 4E is a distal view of an implant.

FIGS. 4A-4E are various views of an implant 25 in an aspect: a side isometric view (FIG. 4A); a side view (FIG. 4B); a top view (FIG. 4C); a proximal view (FIG. 4D); and a distal view (FIG. 4E). Referring to FIG. 4A, the implant 25 may have an implant length 402 extending from a proximal end 404 to a distal end 406. Referring to FIG. 4B, the implant 25 may further have an implant height 426 extending from a top edge 428 to a bottom edge 430. The distal end 406 may be introduced between the articular surfaces 1016 of a sacroiliac joint 1000 during implantation, as illustrated in FIG. 3. The implant 25 may include various features and elements to facilitate the insertion of the implant 25 into the sacroiliac joint 1000 of the subject, to enhance the fixation of the implant 25 within the sacroiliac joint 1000, and to facilitate the fusion of the sacroiliac joint 1000 and implant 25 over extended use.

In various aspects, the implant length 402 may range from about 15 mm to about 60 mm. In various other aspects, the implant length 402 may range from about 15 mm to about 25 mm, from about 20 mm to about 30 mm, from about 25 mm to about 35 mm, from about 30 mm to about 40 mm, from about 35 mm to about 45 mm, from about 40 mm to about 50 mm, from about 45 mm to about 55 mm, and from about 50 mm to about 60 mm. In various additional aspects, the implant length 402 may be 15 mm, 20 mm, 25 mm, 30 mm, 35 mm, 40 mm, 45 mm, 50 mm, 55 mm, and 60 mm.

In various aspects, the implant height 426 may range from about 10 mm to about 20 mm. In various other aspects, the implant height 426 may range from about 10 mm to about 12 mm, from about 11 mm to about 13 mm, from about 12 mm to about 14 mm, from about 13 mm to about 15 mm, from about 14 mm to about 16 mm, from about 15 mm to about 17 mm, from about 16 mm to about 18 mm, from about 17 mm to about 19 mm, and from about 18 mm to about 20 mm. In various additional aspects, the implant height 426 may be 10 mm, 11 mm, 12 mm, 13 mm, 14 mm, 15 mm, 16 mm, 17 mm, 18 mm, 19 mm, and 20 mm.

Figure 4F:
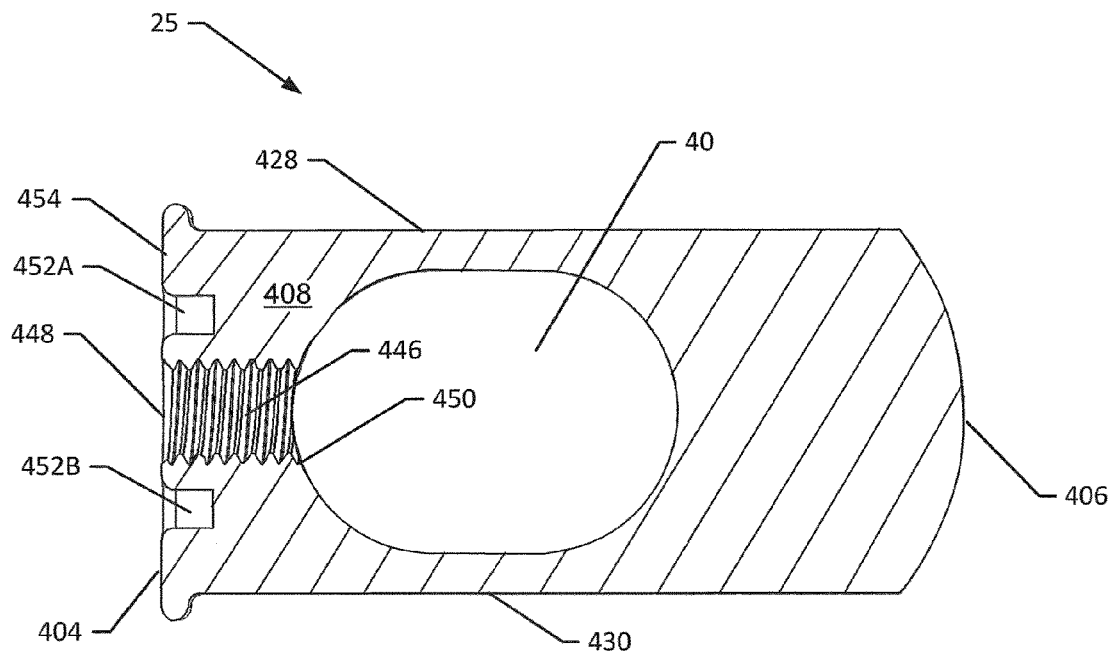
FIG. 4F is a longitudinal cross-section of an implant taken along A-A of FIG. 4A.
Figure 5A:
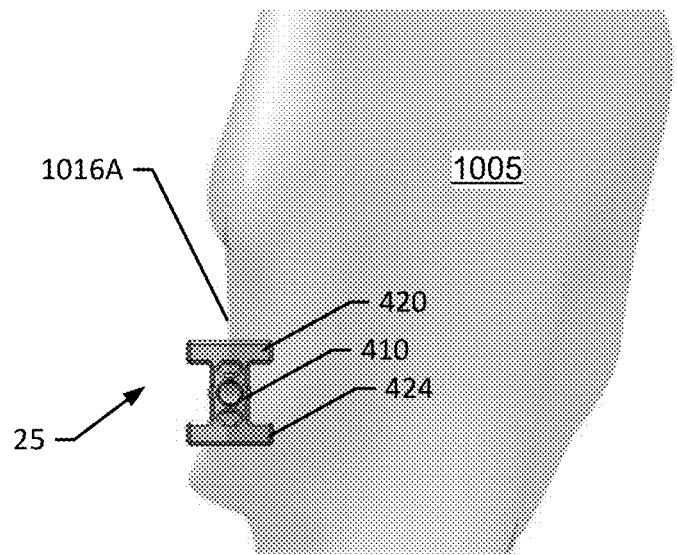
FIG. 5A is a posterior view of an implant secured within a sacroiliac joint of a subject in which the sacrum is hidden.
Figure 5B:
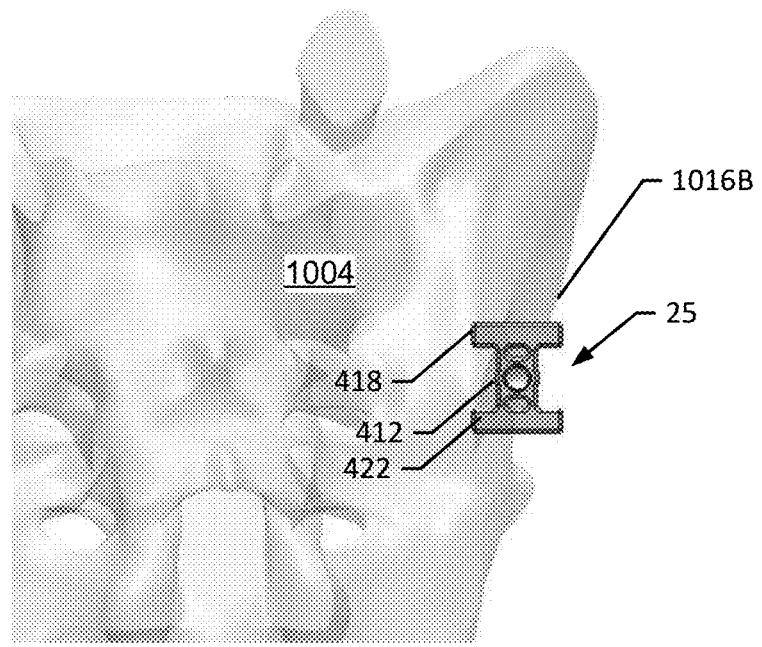
FIG. 5B is a posterior view of an implant secured within a sacroiliac joint of a subject in which the ilium is hidden.

Referring again to FIGS. 4A-4F, the implant 25 may include an intra-articular element 408 extending at least a portion of the implant length 402. The intra-articular element 408 may include a first articular face 410 and an opposed second articular face 412. The first and second articular faces 410/412 may contact the articular surfaces 1016 of the sacroiliac joint 1000 when implanted, as illustrated in FIG. 3. Referring to FIG. 5A, the first articular face 410 may contact the articular surface 1016A of the ilium 1005. Referring to FIG. 5B, the second articular face 412 may contact the sacrum 1004 or the articular surface 1016B of the sacrum 1004.

Referring to FIG. 4E, the intra-articular element 408 may include an intra-articular thickness 440 extending from the first articular face 410 and the second articular face 412. The intra-articular thickness 440 may be influenced by any one or more of at least several factors including, but not limited to the width of the joint space 1044 at the region of the sacroiliac joint 1000 within which the implant 25 is to be inserted, the desired amount of taper at the distal end 406 of the implant 25, the desired structural integrity of the implant, the length of the anchor 30 to be inserted transversely across the intra-articular element 408, and the size of any holes, bores, windows, fittings, and the like to be formed at least partially within the intra-articular element 408. In various aspects, the intra-articular thickness 440 may range from about 3 mm to about 10 mm. In various other aspects, the intra-articular thickness 440 may range from about 3 mm to about 5 mm, from about 4 mm to about 6 mm, from about 5 mm to about 7 mm, from about 6 mm to about 8 mm, from about 7 mm to about 9 mm, and from about 8 mm to about 10 mm. In various additional aspects, the intra-articular thickness 440 may be 3 mm, 4 mm, 5 mm, 6 mm, 7 mm, 8 mm, 9 mm, and 10 mm.

In various embodiments, the first and second articular faces 410/412 of the implant 25 may be selected to match the contour of the joint space of the sacroiliac joint 1000 within which the implant 25 is to be inserted. For example, the first and second articular faces 410/412 of the implant 25 may be configured to be generally convex to match the contour of a sacral auricular bony surface or to match the contour of an extra-articular region of a sacrum 1004 (e.g., a sacral fossa). In one aspect, the sacral, medial or second articular face 412 of the implant 25 may be generally a surface negative of the articular surfaces 1016 of the extra-articular space 3007 and/or intra-articular region 1044 of the sacrum 1004. As another example, the lateral, iliac or second articular face 410 of the implant 25 may be configured to be generally concave to match the contour of an iliac auricular boney surface or to match the contour of an extra-articular region of an ilium (e.g., an iliac tuberosity). In one aspect, the lateral, iliac or second articular face 410 of the implant 25 may be generally a surface negative of the articular surfaces 1016 of the extra-articular space 3007 and/or intra-articular region 1044 of the ilium 1005.

Referring again to FIGS. 4A-4F, the intra-articular element 408 may further contain a graft window 40 extending in an essentially transverse direction through the first and second articular faces 410/412. The graft window 40 may reduce the amount of an implant material including, but not limited to, a metal, within the joint space 1044 of the sacroiliac joint 1000. The graft window 40 may further provide a space through which the bone tissues of the sacrum 1004 and ilium 1005 may grow and fuse during long-term residence of the implant 25 in the sacroiliac joint 1000. In addition, the graft window 40 may provide a path through which the anchor 30 may pass transversely through the implant 25 in order to secure the implant 25 within the sacroiliac joint 1000, as illustrated in FIG. 2 by way of non-limiting example.

Figure 4G:
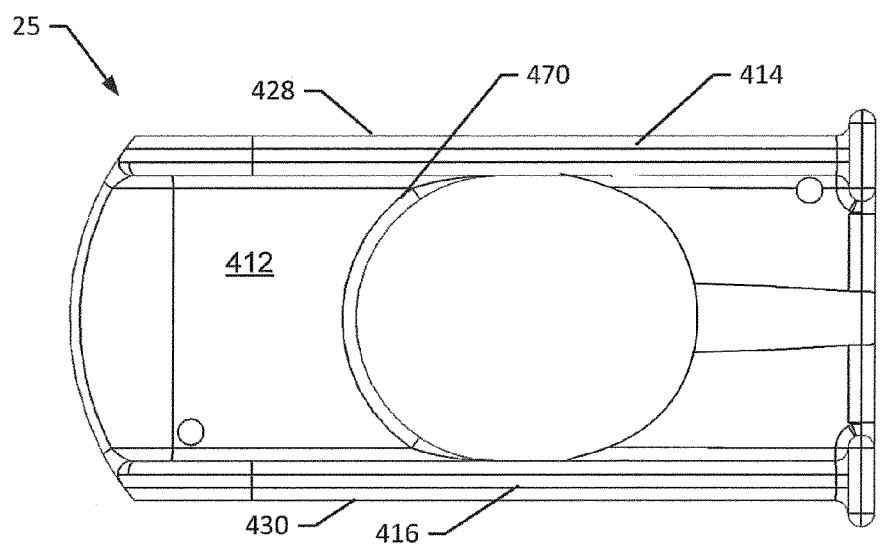
FIG. 4G is a side view of an implant opposite to the side view illustrated in FIG. 4B.

The graft window 40 may occupy at least a portion of the area of the first and second articular faces 410/412. Without being limited to any particular theory, a relatively large graft window 40 may provide a wider range of fastener trajectories for any anchors 30 passing through the graft window 40, may reduce the amount of material within the joint space 1044 or occupying the sacroiliac joint plane 1030 and associated risk of complications, and may enhance the potential fusion of the implant 25 with the surrounding bone tissue within the joint space 1044. However, the size of the graft window 40 may be limited to a maximum size above which 1) the structural integrity of the implant 25 may be compromised due to the reduction in implant material associated with the graft window 40, or 2) the surface area of the first and second articular faces 410/412 may have insufficient engagement or contact with the bone which may result in subsidence of the implant 25 into the bones. Referring to FIG. 4B and FIG. 4G, the graft window 40 may have a first window opening 468 on the first articular face 410 as illustrated in FIG. 4B. The first window opening 468 may be situated in close proximity to the ilium 1005. Referring to FIG. 4G, the graft window 40 may have a second window opening 470 on the second articular face 412. The second window opening 470 may be situated in close proximity to the sacrum 1004. The first window opening 468 may be larger than the second window opening 470 due to a greater likelihood of subsidence of implant 25 into the sacrum 1004 due to lower bone density. An implant 25 with a larger first window opening may have a first articular face 410 with an area that is less than the area of the second articular face 412.

In an aspect, the first window opening 468 and the second window opening 470 may be equal, yet the first articular face 410 may have an area which is less than the area of the second articular face 412. Without being limited to a particular theory, this configuration may permit a greater dispersion of force upon the sacrum over a greater area, thereby lessening the possibility of subsidence.

Referring to FIG. 4B, the graft window 40 may include a window length 442 extending from a proximal edge to a distal edge of the graft window 40. The window length 442 may vary based on a variety of factors, including the factors related to the overall size of the graft window 40 described herein previously, as well as the implant length 402. In various aspects, the window length 442 may range from about 40% to about 70% of the implant length 402. In various other aspects, the window length 442 may vary from about 40% to about 50%, from about 45% to about 55%, from about 50% to about 60%, from about 55% to about 65%, and from about 60% to about 70% of the implant length 402. In various additional aspects, the window length 442 may be about 40%, about 45%, about 50%, about 55%, about 60%, about 65%, and about 70% of the implant length 402. In various aspects, the window length 442 may range from about from about 10 mm to about 40 mm. In various other aspects, the window length 442 may range from about 10 mm to about 20 mm, from about 15 mm to about 25 mm, from about 20 mm to about 30 mm, from about 25 mm to about 35 mm, and from about 30 mm to about 40 mm. In various additional aspects, the window length 442 may be 10 mm, 12 mm, 14 mm, 15 mm, 16 mm, 18 mm, 20 mm, 22 mm, 24 mm, 25 mm, 26 mm, 28 mm, 30 mm, and 40 mm.

Figure 7A:
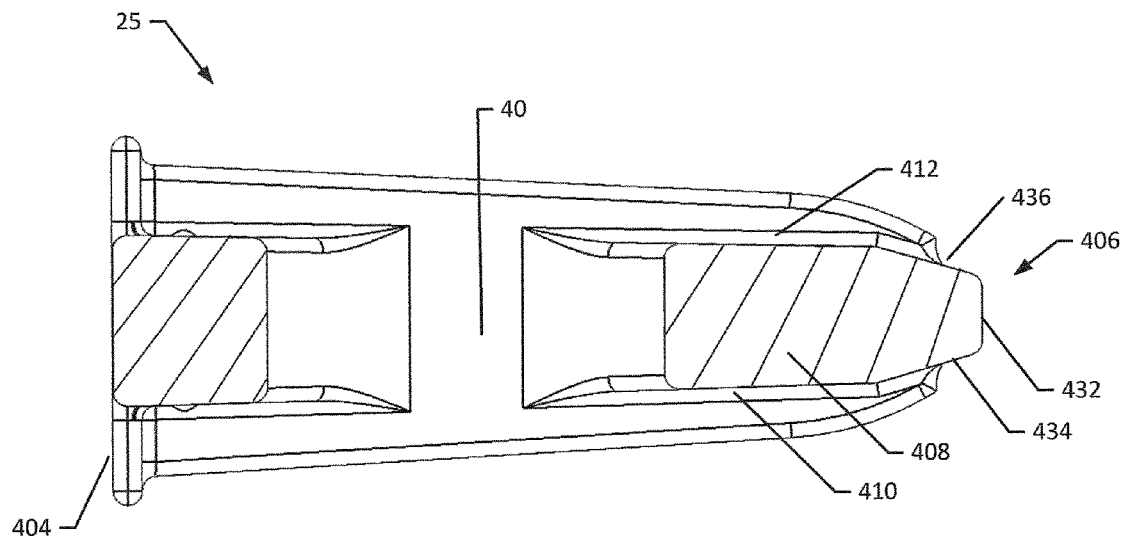
FIG. 7A is a side view of a dual-keel implant with a graft window extending perpendicularly through an intra-articular element of the implant.
Figure 7B:
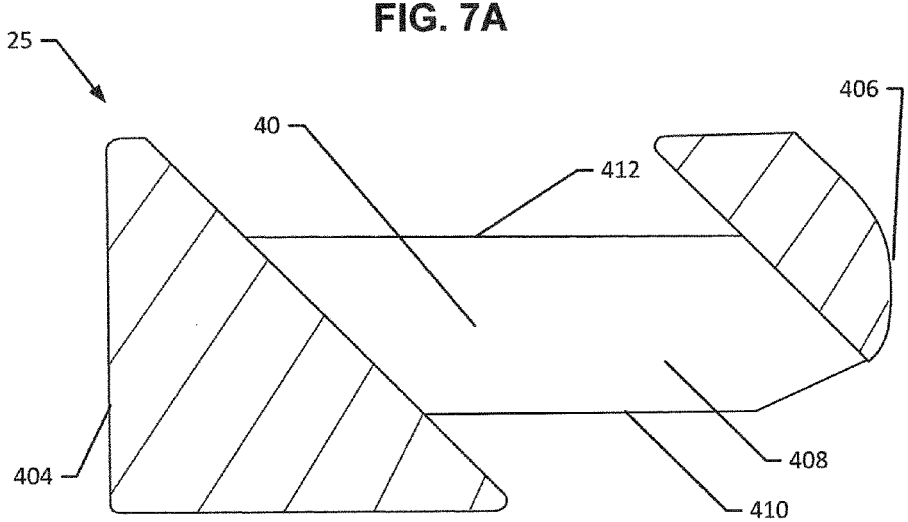
FIG. 7B is a side view of a single-keel implant with a graft window extending at a 45° angle through an intra-articular element of the implant.

In various aspects, the graft window 40 may pass through the intra-articular element 408 at a range of angles relative to a plane parallel to the first and second articular faces 410/412. In various aspects, the graft window 40 may pass through the intra-articular element 408 at a range of angles relative to a plane parallel to the first and second articular faces 410/412 ranging from about 45° to about 90° (i.e. normal to the first and second articular faces 410/412). In various other aspects, the graft window 40 may pass through the intra-articular element 408 at a range of angles relative to a plane parallel to the first and second articular faces 410/412 ranging from about 45° to about 55°, from about 50° to about 60°, from about 55° to about 65°, from about 60° to about 70°, from about 65° to about 75°, from about 70° to about 80°, from about 75° to about 85°, and from about 80° to about 90°. In various other aspects, the graft window 40 may pass through the intra-articular element 408 at an angle of 45°, 50°, 55°, 60°, 65°, 70°, 75°, 80°, 85°, and 90° angles relative to a plane parallel to the first and second articular faces 410/412. Referring to FIG. 4F, the graft window 40 may pass through the intra-articular element 408 at an angle of about 90° in an aspect. Referring to FIGS. 7A and 7B, the graft window 40 may pass through the intra-articular element 408 at an angle of 90° (see FIG. 7A) in one aspect, and at an angle of 45° (see FIG. 7B) in another aspect.

In various aspects, the implant 25 may include a graft window 40 in which the perimeter of the graft window 40 may be provided with any known profile without limitation. Non-limiting examples of suitable profiles for the graft window 40 in various aspects include: a circular profile, an elliptical profile, a square profile, and a rectangular profile. In one aspect the profile of the graft window 40 may be provided in the form of an elliptical profile, as illustrated in FIG. 4B by way of non-limiting example.

Figure 13:
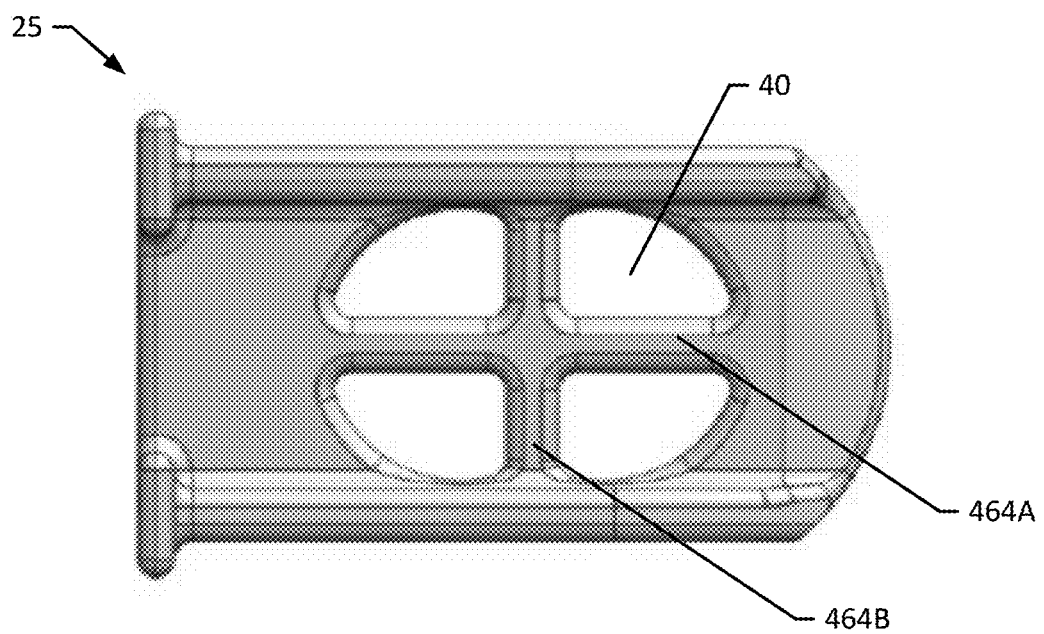
FIG. 13 is a side view of an implant with additional reinforcing elements within a graft window.

Referring to FIG. 13, the graft window 40 of the implant 25 may further include at least one reinforcing element 464 to enhance the structural integrity of an implant 25 containing a graft window 40 in various aspects. In various aspects, the graft window 40 may further include a horizontal reinforcing element 464A extending along the length of the graft window 40 and/or a vertical reinforcing element 464B extending along the height of the graft window 40. In these various aspects, the at least one reinforcing element 464 may occlude the anchor trajectory of an anchor 30 (not shown) through the graft window 40, necessitating the use of additional anchors (not shown) directed along anchor trajectories that pass essentially transversely to the intra-articular element 408 of the implant 25 and caudad and/or cephalad relative to the implant 25.

Figure 10:
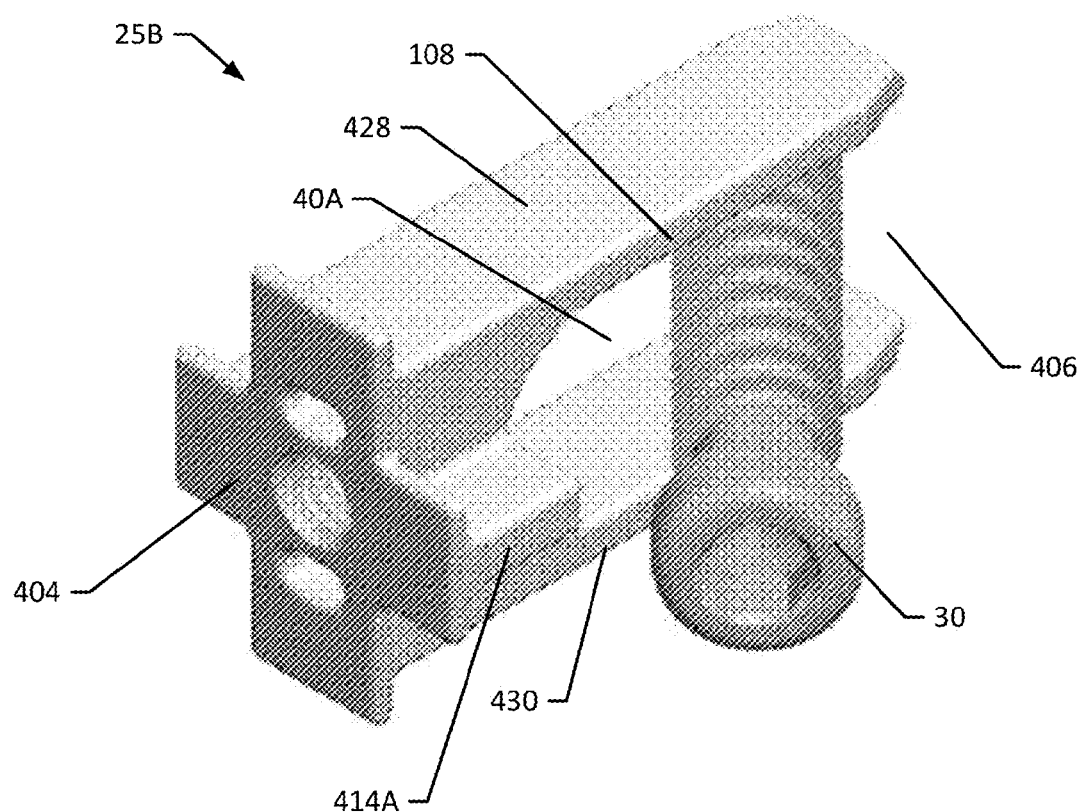
FIG. 10 is a proximal perspective view of an implant with an extended graft window and an anchor inserted transversely through the extended graft window.

Referring to FIG. 10, in one aspect an implant 25B may include an extended graft window 40A that includes an open distal end 406. In this aspect, the extended graft window 40A may permit a wider range of potential anchor trajectories by eliminating the possibility of mechanical interference between the anchor 30 and the distal end 406 of the implant 25B. Further, the extended graft window 40A may reduce the amount of implant material maintained within the joint space 1044 due to the elimination of the distal end 406 and associated structure of the implant 25B. In addition, the extended graft window 40A may be produced with any number of transverse keels while maintaining lateral symmetry, thereby simplifying the manufacturing and implantation of the implant 25B. The extended graft window 40A also permits the implant 25B to be inserted into the joint space 1044 after the anchor 30 has been inserted in a transverse trajectory across the sacroiliac joint 1000.

Without being limited to any particular theory, the surface area of all material introduced into the joint plane of the sacroiliac joint 1000 by the insertion of the implant 25 and associated anchor 30 may be associated with a risk of adverse effects, in particular if the implant 25 and anchor 30 are formed of a material which is not sufficiently osseointegrating. FIG. 4F is a cross-section of the implant 25 taken through a plane approximating the joint plane of the sacroiliac joint 1000. As illustrated in FIG. 4F, a significant portion of the surface area of material within the joint plane comprises the intra-articular element 408, and this area is significantly reduced by the inclusion of the graft window 40. In one aspect, the total surface area of material introduced within the joint plane by the insertion of the implant 25 and anchor 30 may be less than about 400 mm$^2$. In various other aspects, the total surface area of material introduced within the joint plane by the insertion of the implant 25 and anchor 30 may be less than about 380 mm$^2$, less than about 360 mm$^2$, less than about 340 mm$^2$, less than about 320 mm$^2$, less than about 300 mm$^2$, less than about 280 mm$^2$, less than about 260 mm$^2$, less than about 240 mm$^2$ less than about 220 mm$^2$, less than about 200 mm$^2$, less than about 180 mm$^2$, less than about 160 mm$^2$, less than about 150 mm$^2$, less than about 145 mm$^2$, and less than about 140 mm$^2$.

Referring again to FIG. 7A, the distal end 406 of the implant 25 may further include various features to facilitate the insertion of the implant 25 into the joint space 1044 of the sacroiliac joint 1000 of the subject. In one aspect, the profile of the distal end 406 along the height 426 of the implant 25 may be tapered in order to provide a gradual increase in cross-sectional area as the distal end 406 is inserted into the joint space 1044. In one aspect, profile of the distal end 406 along the height 426 of the implant 25 may be provided in the form of a rounded leading edge 432, as illustrated in FIG. 4B. In addition, the leading edge 432 may include a first lateral facet 434 and a second lateral facet 436 to provide a gradual transition from the relatively narrow leading edge 432 to the relatively wider remainder of the intra-articular element 408 situated proximal to the leading edge 432.

In various aspects, the implant 25 may further include at least one transverse keel extending over at least a portion of the implant length 402. Referring again to FIGS. 4A-4F, the implant 25 may include a top keel 414 and a bottom keel 416 situated along the top edge 428 and bottom edge 430 of the implant 25, respectively. The top keel 414 may project perpendicularly from the first and second articular faces 410/412, ending in a first top lateral edge 418 and an opposed second top lateral edge 420. The bottom keel 416 may project perpendicularly from the first and second articular faces 410/412, ending in a first bottom lateral edge 422 and a second bottom lateral edge 424.

Referring again to FIG. 3, each keel 414/416 may project transversely across the sacroiliac joint 1000 in various aspects. This transverse projection of the keels 414/416 may inhibit the cranial and/or caudal movements of the implant within the joint space 1044. In addition, the keels 414/416 may provide additional contact area to facilitate the overgrowth of bone tissue over the implant 25. Referring to FIG. 5B, the first top lateral edge 418 and the first bottom lateral edge 422 may project into an articular surface 1016B of the sacrum 1004 in an aspect. Referring to FIG. 5A, the second top lateral edge 420 and the second bottom lateral edge 424 may project into an articular surface 1016A of the ilium 1005 in an aspect.

Figure 6A:
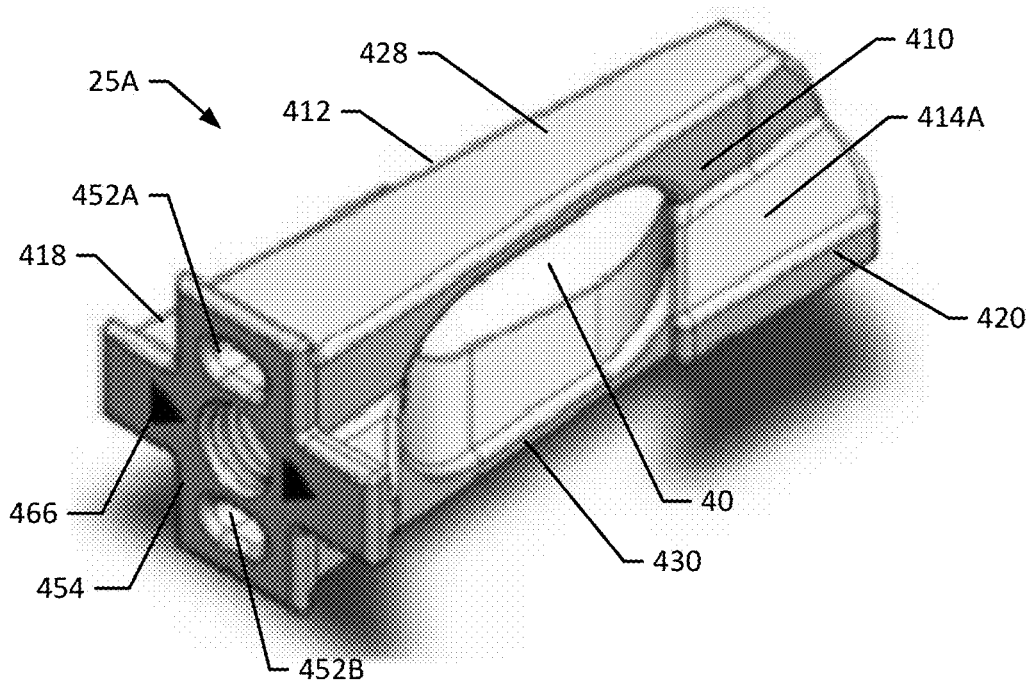
FIG. 6A is a proximal perspective view of a single-keel implant.
Figure 6B:
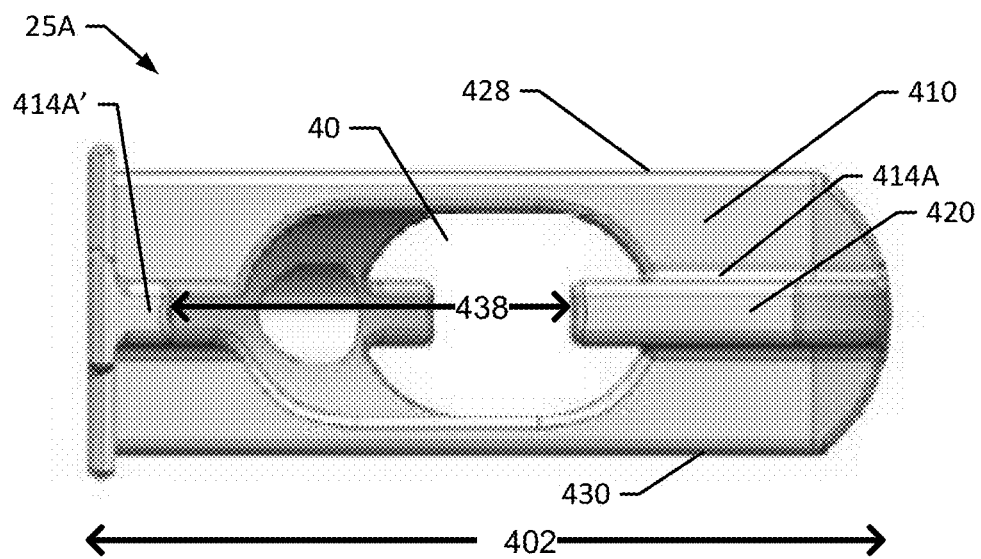
FIG. 6B is a side view of a single-keel implant.

In various aspects, the implant 25 may further include at least one transverse keel extending over at least a portion of the implant length 402. In one aspect, the implant may be a dual keel implant 25, as illustrated in FIGS. 4A-4F. In another aspect, the implant may be a single keel implant 25A, as illustrated in FIGS. 6A-6B. In various aspects, the implant 25 may include 1 keel, 2 keels, 3 keels, 4 keels, 5 keels, 6 keels, and 7 keels.

Referring to FIGS. 6A-6B, the implant 25 may include a single keel 414A situated between the top edge 428 and bottom edge 430 of the implant 25. The single keel 414A may project perpendicularly from the first and second articular faces 410/412, ending in a first top lateral edge 418 and an opposed second top lateral edge 420.

Referring again to FIGS. 4A-4F, the dual keel implant 25 in one aspect may include a top keel 414 and a bottom keel 416 situated along the top edge 428 and bottom edge 430 of the implant 25, respectively. The top keel 414 may project perpendicularly from the first and second articular faces 410/412, ending in a first top lateral edge 418 and an opposed second top lateral edge 420. The bottom keel 416 may project perpendicularly from the first and second articular faces 410/412, ending in a first bottom lateral edge 422 and a second bottom lateral edge 424.

Referring again to FIG. 3, each keel 414/416 may project transversely across the sacroiliac joint 1000 in various aspects. This transverse projection of the keels 414/416 may inhibit the cranial and/or caudal movements of the implant within the joint space 1044. In addition, the keels 414/416 may provide additional contact area to facilitate the growth of bone tissue about the implant 25. Referring to FIG. 5B, the first top lateral edge 418 and the first bottom lateral edge 422 may project into the sacrum 1004 in an aspect. Referring to FIG. 5B, the second top lateral edge 420 and the second bottom lateral edge 424 may project into the ilium 1005 in an aspect.

Figure 6C:
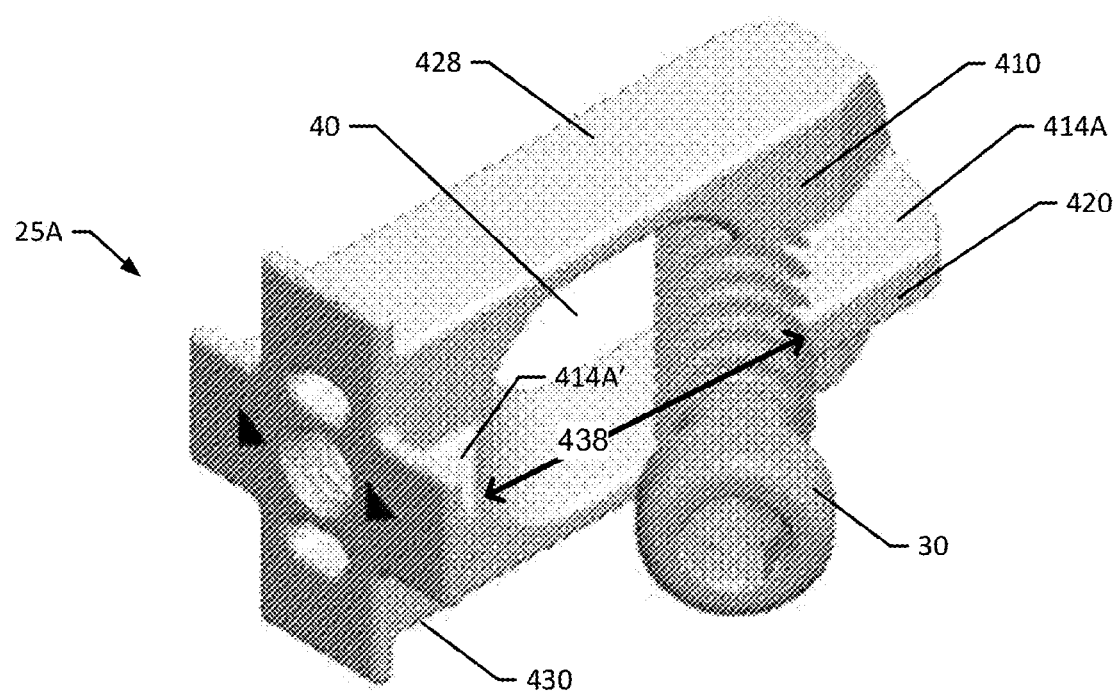
FIG. 6C is a proximal perspective view of a single-keel implant with an anchor through a graft window.

FIGS. 6A and 6B are rear isometric and side views, respectively, of an implant 25 that includes a single keel 414A extending distally along at least a portion of the implant length 402 between the top edge 428 and the bottom edge 430 of the implant. In this aspect, the single keel 414 extends perpendicularly outward from the first and second articular faces 410/412, and is typically situated transversely across a sacroiliac joint 1000 during use. In this aspect, the single keel 414 may extend distally across the graft window 40 of the intra-articular element 408. As illustrated in FIGS. 6A and 6B, the single keel 414 may include a proximal keel portion 414A' and a distal keel portion 414A" separated by a gap 438 over the graft window 40. Referring to FIG. 6C, the gap 438 may provide a clear anchor trajectory for the insertion of an anchor 30 through the graft window 40 to secure the implant 25 within the sacroiliac joint 1000 (not shown).

Referring again to FIGS. 4D and 4E, the at least one keel 414/416 projects transversely away from the intra-articular element 408 may end at a first lateral edge 418/422 and a second lateral edge 420/424. The lateral edges 418/420/422/ 424 may have any cross-sectional profile without limitation. Non-limiting examples of suitable cross-sectional profiles for the lateral edges 418/420/422/424 include planar profiles, faceted or polygonal profiles such as triangular, square, octagonal and the like; rounded profiles such as semi-circular, semi-elliptical, parabolar, and the like.

Figure 9A:
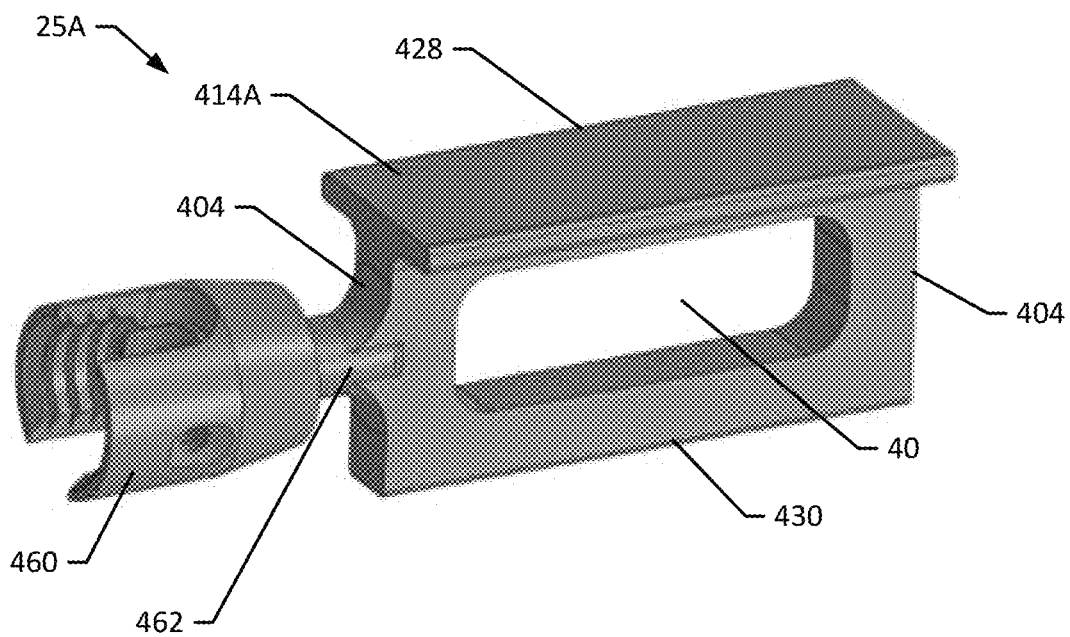
FIG. 9A is a side view of a single keel implant with a monoaxial or polyaxial attachment fitting coupled to a proximal end of the implant.

In various aspects, the at least one keel 414/416 extends in a proximal direction along the length 402 of the implant 25 at any location on the implant 25 without limitation. In one non-limiting example, illustrated in FIG. 4A, the dual keels 414/416 may be situated at or near the top edge 428 and bottom edge 430 of the implant 25. In another non-limiting example, illustrated in FIG. 6A, the single keel 414A may be situated at a location between the top edge 428 and bottom edge 430 of the implant 25. In yet another example, illustrated in FIG. 9, the single keel 414A of a single keel implant 25A may be situated at the top edge 428 of the implant 25A.

In various aspects, the lateral edges 418/420/422/424, first and second articular faces 410/412, keels 414/414A/416, and edges 428/430 may further include additional surface textures to enhance the securing of the implant 25 within the joint space 1044. Non-limiting examples of suitable surface textures include: serrations, holes, furrows, and other depressions; and/or bumps, ridges, points, knurling, and other raised surface features. In one aspect, the lateral edges 418/420/422/424 may have a planar profile, as illustrated in FIGS. 4D-4E.

Referring to FIG. 4C, the lateral edges 418 and 420 may define an overall profile of the implant 25 as viewed from above. In various aspects, the lateral edges 418 and 420 of a keel 414 as viewed from above may be linear, curved, or a combination of linear and curved. In one aspect (not shown), at least a portion of the first lateral edge 418 and at least a portion of the second lateral edge 420 may be parallel to one another along the length 402 of the implant 25. In another aspect, the first lateral edge 418 and the second lateral edge 420 may taper inward toward the distal end 406 to enhance the ease of insertion of the implant 25 into the joint space 1044 or bone. Referring to FIG. 4C, a distal portion 418A/420A of the first and second lateral edges 418/420 may taper to a lesser extent than the taper of a proximal portion 418B/420B of the first and second lateral edges 418/420. Other pairs of lateral edges on opposite sides of the same keel may be similarly tapered in other aspects.

Figure 8:
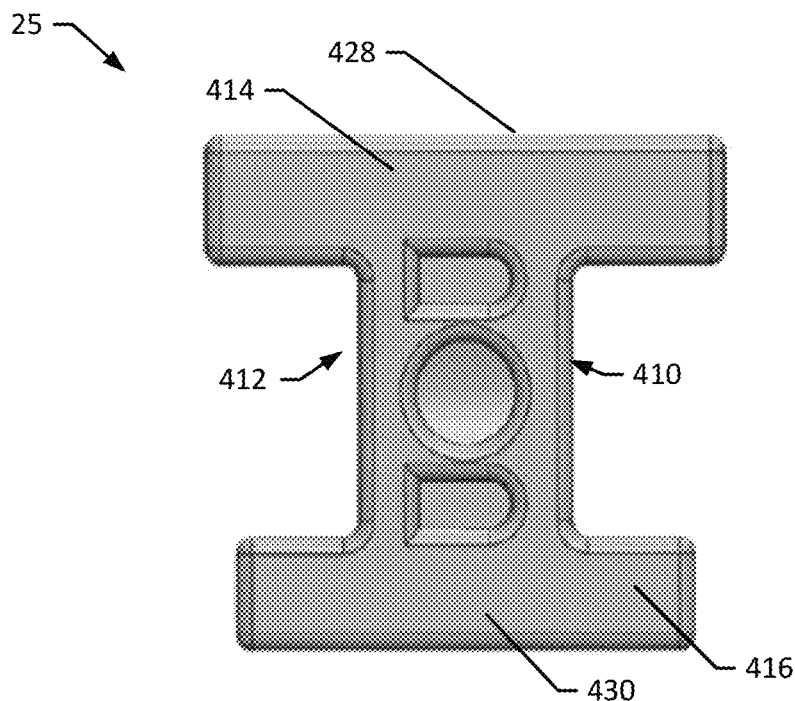
FIG. 8 is a proximal view of a dual-keel implant with unequal keel widths and thicknesses.

In one aspect, the keels may be sized according to the local region of the bone and joint space 1044 within which the keels are to be inserted. In one aspect, shown in FIG. 8, a bottom keel 416 to be situated in the vicinity of a sciatic notch 2008 (not shown) may be narrower than a top keel 414 situated further cephalad with respect to the sciatic notch 2008. In one aspect, the narrower bottom keel 416 may enhance the compatibility of this keel 416 with the articular surfaces 1016 near the sciatic notch, which may include relatively thinner cancellous bone or lesser bone volume of the ilium or sacrum in close proximity to the anticipated placement of the narrower bottom keel 416. In another aspect, shown in FIG. 4D, the top and bottom keels 414/416 may be of similar width; the width of the top and bottom keels 414/416 may be selected to be compatible with the thickness of cancellous bone near the sciatic notch 2008. In this other aspect, the similar widths of the top and bottom keels 414/416 permit the implant 25 to be implanted with the top keel 414 facing upward or inverted with the top keel 414 facing downward without need to reconfigure the delivery tool 20.

Referring to FIGS. 4D and 4E, each keel 414 may include a width 444 extending between the lateral edges 418 and 420 of top keel 414 in an aspect. Referring to FIG. 4C, this width 444 typically defines an overall width of the implant 25 in various aspects. The width 444 may correspond to a maximum width if the keel 414 is tapered, as illustrated in FIG. 4C in one aspect. In another aspect (not shown) the width may be relatively constant if the lateral edges 418 and 420 extend distally in an essentially parallel manner.

In various aspects, the width 444 of each keel 414/414A/416 may range from about 8 mm to about 20 mm. In various other aspects, the width 444 of each keel 414/414A/416 may range from about 8 mm to about 10 mm, from about 9 mm to about 11 mm, from about 10 mm to about 12 mm, from about 11 mm to about 13 mm, from about 12 mm to about 14 mm, from about 13 mm to about 15 mm, from about 14 mm to about 16 mm, from about 15 mm to about 17 mm, from about 16 mm to about 18 mm, from about 17 mm to about 19 mm, and from about 18 mm to about 20 mm. In various additional aspects, the width 444 of each keel 414/414A/416 may be 8 mm, 9 mm, 10 mm, 11 mm, 12 mm, 13 mm, 14 mm, 15 mm, 16 mm, 17 mm, 18 mm, 19 mm, and 20 mm.

The keel width 444 of a keel 416 for insertion in the joint space 1044 near the sciatic notch 2008 may be slightly reduced as described herein previously to provide compatibility with the relatively thin cancellous bone is this region in an aspect. In this aspect, the keel width 444 may range between about 10 mm and about 16 mm, or within any of the subranges between about 10 mm and about 16 mm defined herein above. In various aspects, the keel width 444 of each keel 414/416 of a dual keel implant 25 (see, for example, FIGS. 4A-4E) may be slightly narrower compared to a keel width 444 of a single keel implant 25A with comparable implant length 402 and implant height 426.

Figure 11A:
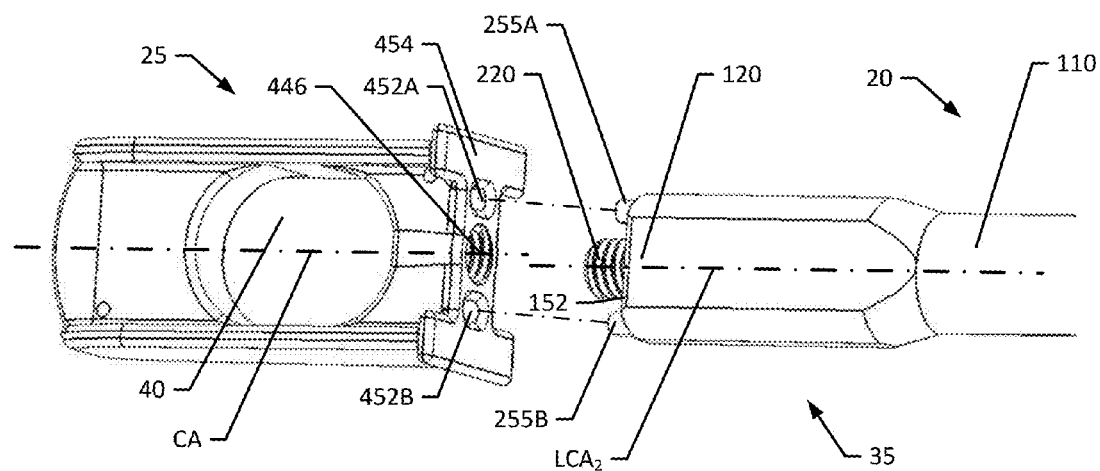
FIG. 11A is an exploded side view of a dual-keel implant separated from a distal end of a delivery tool.
Figure 11B:
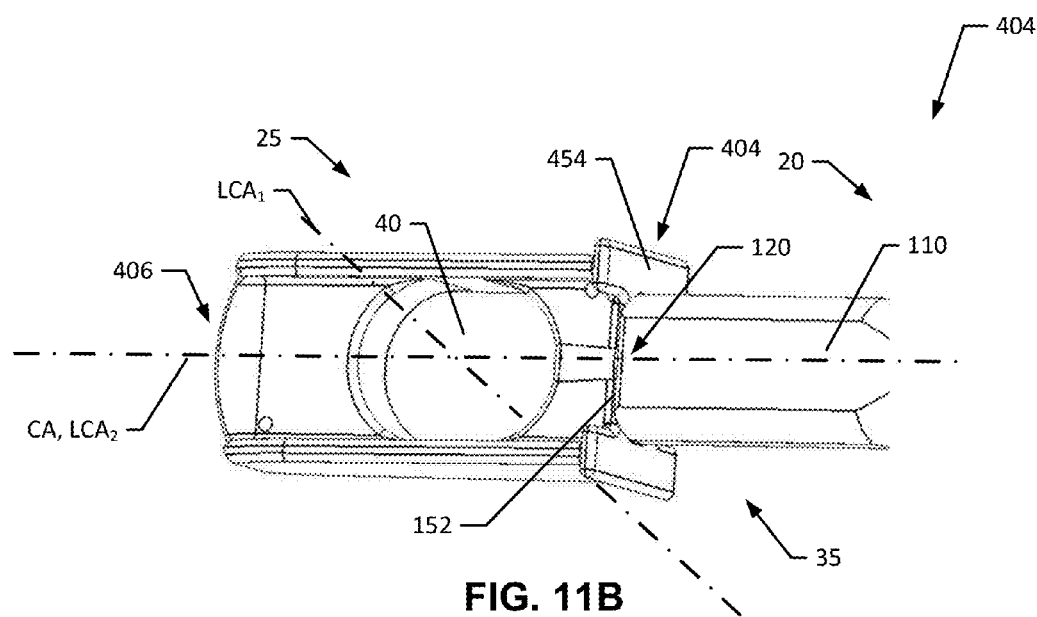
FIG. 11B is a side view of a dual-keel implant mounted to a distal end of a delivery tool.

Referring again to FIG. 4D, the proximal end 404 of the implant 25 may include at least one or more features associated with reversibly attaching the implant 25 to a distal end 35 of a delivery tool 20, as illustrated previously in FIG. 1. In various aspects, the proximal end 404 of the implant 25 may include a threaded bore 446 formed in the proximal end 404 and extending distally from the proximal face 454 of the proximal end 404 into the implant 25. Referring to FIG. 4F, the threaded bore 446 may extend distally through the material of the intra-articular element 408, and may open at a distal bore opening 450 into the graft window 40 opposite to a proximal bore opening 448 at the proximal face 454. Referring to FIG. 11A, the threaded bore 446 may receive a distal end of an implant engagement feature in the form of a threaded shaft 220. The threaded shaft 220 may be advanced into the threaded bore 446 and tightened to reversibly couple the proximal end 404 of the implant 25 to the distal end 35 of the delivery tool 20, as illustrated in FIG. 11B.

In various aspects, the internal diameter of the threaded bore 446 may be matched to the diameter of the threaded shaft 220 and may range from about 3 mm to about 5 mm. The diameter of the threaded shaft 220 may be sufficiently large to secure the implant 25 to the delivery tool 20 without significantly increasing the thickness 440 of the intra-articular element 408. In various aspects, the internal diameter of the threaded bore 446 may range from about 3 mm to about 5 mm. In various other aspects, the internal diameter of the threaded bore 446 may range from about 3 mm to about 3.4 mm, from about 3.2 mm to about 3.6 mm, from about 3.4 mm to about 3.8 mm, from about 3.6 mm to about 4.0 mm, from about 3.8 mm to about 4.2 mm, from about 4 mm to about 4.4 mm, from about 4.2 mm to about 4.6 mm, from about 4.4 mm to about 4.8 mm, and from about 4.6 mm to about 5 mm. In various additional aspects, the internal diameter of the threaded bore 446 may be 3 mm, 3.2 mm, 3.25 mm, 3.5 mm, 3.75 mm, 3.8 mm, 3.9 mm, 4 mm, 4.2 mm, 4.25 mm, 4.5 mm, 4.75 mm, and 5 mm.

Figure 12:
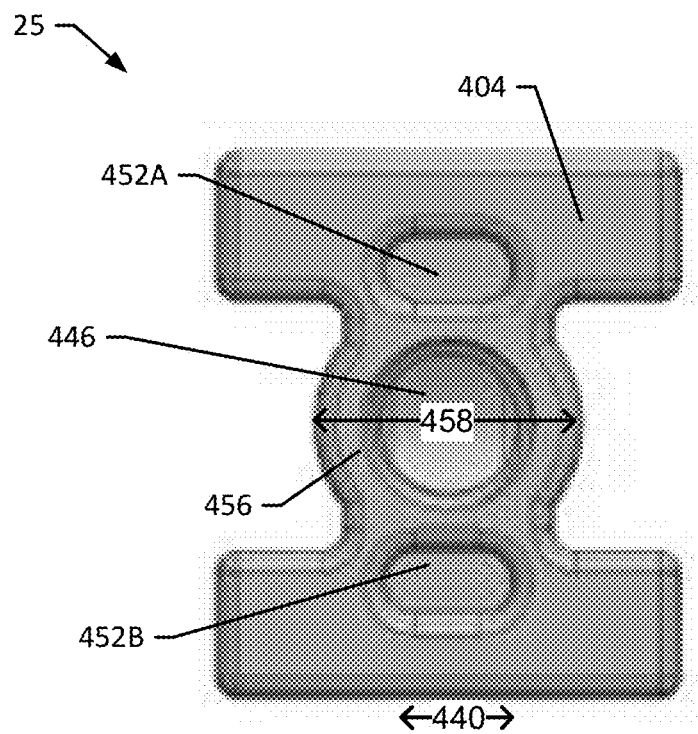
FIG. 12 is a proximal view of an implant with a halo of additional material surrounding a threaded bore formed within the proximal end of the implant.

In various aspects, the desired thickness 440 of the intra-articular element 408 may be less than the internal diameter of the threaded bore 446. Referring to FIG. 12, in one aspect, the proximal end 404 of the implant 25 may further include a halo 456 surrounding the threaded bore 446. In this one aspect, the halo 456 may include an amount of material to contain the threaded bore 446 and maintain sufficient structural integrity during mounting of the implant 25 to the delivery tool 20, as well as during subsequent insertion of the implant 25 into the joint space 1044 of the sacroiliac joint 1000. In various aspect, the halo 456 may result in a minimum thickness of material surrounding the threaded bore 446 of at least about 1 mm, at least about 1.2 mm, at least about 1.4 mm, at least about 1.5 mm, at least about 2 mm, and at least about 4 mm. In various other aspects, a diameter 458 of the halo 456 may range from about 5 mm to about 10 mm. In various other aspects, the diameter 458 of the halo 456 may range from about 5 mm to about 6 mm, from about 5.5 mm to about 6.5 mm, from about 6 mm to about 7 mm, from about 6.5 mm to about 7.5 mm, from about 7 mm to about 8 mm, from about 7.5 mm to about 8.5 mm, from about 8 mm to about 9 mm, from about 8.5 mm to about 9.5 mm, and from about 9 mm to about 10 mm. In various additional aspects, the diameter 458 of the halo 456 may be 5 mm, 5.5 mm, 6 mm, 6.5 mm, 7 mm, 7.5 mm, 8 mm, 8.5 mm, 9 mm, 9.5 mm, and 10 mm.

Referring again to FIG. 11A, the implant 25 may further include one or more alignment bores 452A/452B configured to receive one or more corresponding alignment protrusions 255A/255B extending distally from the distal end 35 of the delivery tool 20. Referring to FIG. 4F, the one or more alignment bores 452A/452B are blind bores extending distally from the proximal face 454 into the material of the intra-articular element 408. The alignment bores 452A/452B are situated at a distance away from the threaded bore 446 corresponding to the positions of the alignment protrusions 255A/255B on the distal end 35 of the delivery tool 20. As the threaded shaft 220 is advanced into the threaded bore 446 and tightened, the alignment protrusions 255A/255B are similarly advanced into the alignment bores 452A/452B. The inner contour of the alignment bores 452A/452B may be essentially matched to the outer contours of the alignment protrusions 255A/255B, thereby reducing mechanical play of the alignment protrusions 255A/255B within the alignment bores 452A/452B upon insertion. In various aspects, the inserted alignment protrusions 255A/255B may ensure that the implant 25 is properly aligned on the distal end 35 of the delivery tool 20. In various other aspects, the inserted alignment protrusions 255A/255B may prevent unwanted movements or shifts in position of the implant 25 and the delivery tool 20 including, but not limited to, twisting or torsional movements.

Alternatively, referring again to FIG. 11A and FIG. 4F, the distal end 35 of the delivery tool 20 may include one or more alignment bores (not shown) configured to receive one or more corresponding alignment protrusions (not shown) extending proximally from the proximal end 404 of the implant 25.

Referring again to FIG. 4D, each alignment bore 452A/452B may include a symmetrical contour in which an alignment protrusion 255 may be inserted in at least two different orientations in one aspect. Non-limiting examples of suitable symmetrical profiles include circular profiles, elliptical profiles, square profiles, rectangular profiles, and any other suitable profile with at least bilateral symmetry. In this one aspect, the implant 25 may have symmetrical features in which the implant 25 may be inserted either upright or inverted as described herein previously. Referring to FIG. 6A, the alignment bores 452A/452B may include a non-symmetrical inner profile in one aspect such that the implant 25 may only be mounted in the distal end 35 of the delivery tool 20 in a single unique orientation to ensure that the implant 25 is properly inserted into the joint space 1044 of the sacroiliac joint 1000. In another aspect, the proximal face 454 of the implant 25 may be provided with one or more alignment markings 466 to aid a practitioner in mounted the implant 25 to the distal end 35 of the delivery tool 20. In various aspects, any combination of non-symmetrical profiles within the alignment bores 452A/452B and/or one or more alignment markings 466 on the proximal face 454 may be included to facilitate alignment of the implant 25 on the delivery tool 20.

Referring again to FIG. 11A, the proximal face 454 of the implant 25 may include a contour that is matched to a corresponding contour (not shown) of the distal end 35 of the delivery tool 20. In one aspect, the proximal face 454 may be essentially planar, thereby enhancing the degree of direct contact between the distal end 35 of the delivery tool 20 and the proximal end 404 of the implant 25. In another aspect, the proximal face 454 of the implant 25 may have a non-planar contour that may be matched to a corresponding non-planar contour of the distal end 35 of the delivery tool 20, including, but not limited to a spherical or hemispherical contour; an ellipsoidal contour, a saddle-shaped contour, and any other suitable contour. In one aspect, the contour of the proximal face 454 may be non-symmetrical and may function as a means of aligning the implant 25 on the distal end 35 of the delivery tool 20.

Referring again to FIGS. 9A and 9B, in various embodiments the implant engagement feature may be provided in forms other than a threaded shaft 220 as described herein previously. In one aspect, the implant 25A may be provided with a monoaxial or polyaxial attachment fitting 460 attached at the proximal end 404 of the implant 25 via a ball joint-type fitting 462. In this aspect, the implant 25 may be secured to the delivery tool 20 using standard tools used to install pedicle screws and other orthopedic devices outfitted with polyaxial heads that are well-known in the art. Once the implant 25 is secured within a sacroiliac joint 1000, the monoaxial or polyaxial attachment fitting 460 may protrude from the sacroiliac joint 1000 and may be configured for use as an anchor for an orthopedic device such as a spinal stabilization appliance. In this embodiment, the delivery tool 20 may be modified to accommodate the monoaxial or polyaxial attachment fitting 460 during insertion of the implant 25.

Figure 9B:
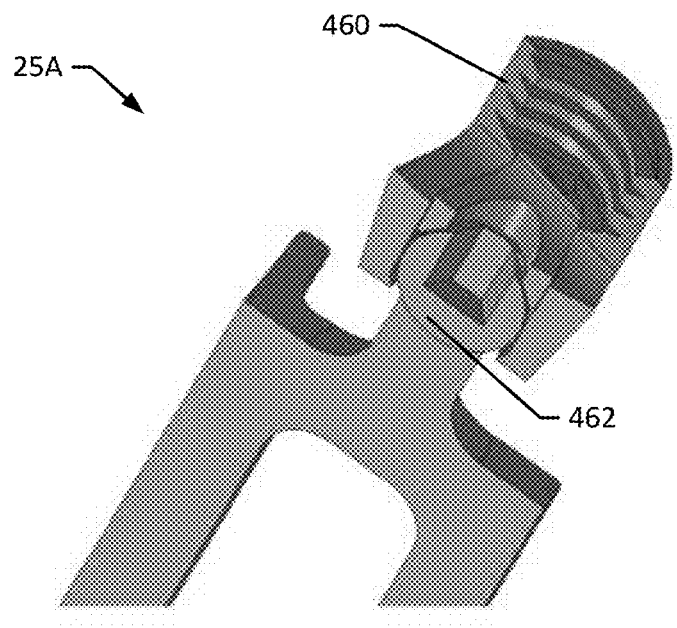
FIG. 9B is a longitudinal cross-sectional view of a single keel implant with a polyaxial head attached at a proximal end of the implant.

The monoaxial or polyaxial attachment fitting 460 may be attached to the proximal end 404 of the implant 25 using a ball joint-type fitting 462, as illustrated in FIG. 9B. The resulting joint may be rotatable in any direction to a limited extent or may be uniplanar.

While reference is made to the embodiment of the implant 25 in FIGS. 4A-4F, the reference numerals are similarly applicable to the implant designs in the other figures.

In various aspects, the implant 25 may be machined, molded, formed, or otherwise manufactured from stainless steel, titanium, metallic implant alloys, ceramic, polymer, composite, bone or other biocompatible materials. In one aspect, the implant 25 may be machined from a metallic implant alloy including, but not limited to a titanium-aluminum-vanadium ELI (Extra Low Interstitial) alloy (ASTM F136). In another aspect, the implant 25 may be machined from a polymer including, but not limited to a polyetheretherketone (PEEK) polymer such as ZENVIA ZA-500. In yet another aspect, the implant 25 may further include a coating to improve osseointegration including, but not limited to, a commercially pure Ti coating (ASTM F1580).

b. Anchor

Referring again to FIG. 3, the implant assembly 15 may include an anchor 30 inserted transversely across the sacroiliac joint 1000 to hold the implant 25 in place within the joint space 1044 of the sacroiliac joint 1000. The anchor 30 may be inserted along a generally lateral-medial fastener trajectory in which the anchor passes through the ilium 1005, through the graft window 40 of the implant 25, and penetrate the sacrum 1004. In various aspects, the anchor 30 may be provided in the form of any suitable elongated body including, but not limited to: a nail, a rod, a pin, a threaded screw, an expanding body, a cable (e.g., configured with a ball end), and the like. In one aspect, the anchor 30 is configured to be received in the graft window 40 defined through intra-articular element 408 of the implant 25. The graft window 40 extends through the implant 25 and is sized such that the anchor element 30 may extend through the implant 25 as illustrated in FIG. 3. In one aspect, the graft window 40 and at least one keel 414 may be sized to minimize toggling of the anchor 30 through a range of anchor trajectories through the graft window 40 of the implant 25.

Figure 14:
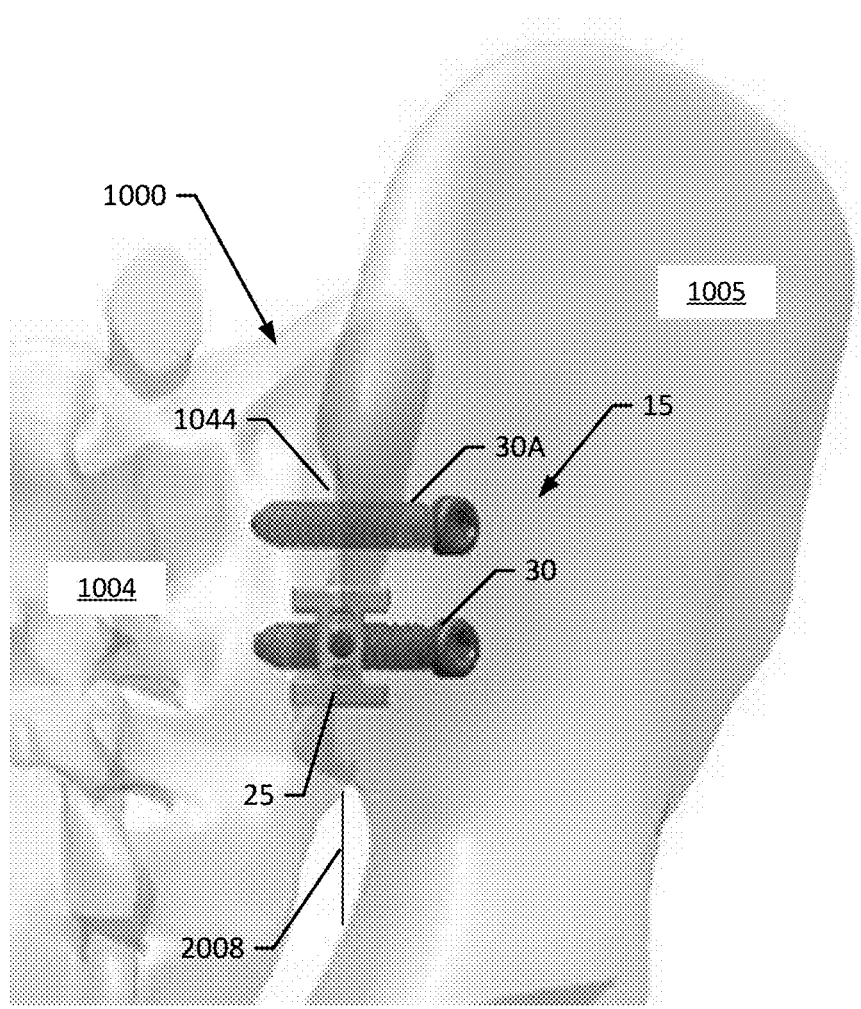
FIG. 14 is a posterior view of an anchor, an additional anchor, and an implant secured within a sacroiliac joint of a subject.

Referring to FIG. 14, the implant assembly 15 may further include an additional anchor 30A, also inserted transversely across the sacroiliac joint 1000 in a generally lateral-medial fastener trajectory. In one aspect, the second anchor 30A may be inserted along a fastener trajectory situated caudad relative to the implant 25 such that the second anchor 30A crosses the joint space 1044 without passing through the graft window. In one aspect, the additional anchor 30A may be used instead of the anchor 30 to hold the implant 25 in place within the joint space 1044 as needed. In one non-limiting example, the additional anchor 30A may be used if the articular surfaces 1016 are degraded in the region adjacent to the implant 25, thereby limiting the effectiveness of an anchor 30 inserted through the implant 25. In another non-limiting example, the additional anchor 30A may be used in certain aspects of the implant in which the graft window 40 may be partially occluded by additional reinforcement elements 464, as illustrated in FIG. 13.

Figure 15A:
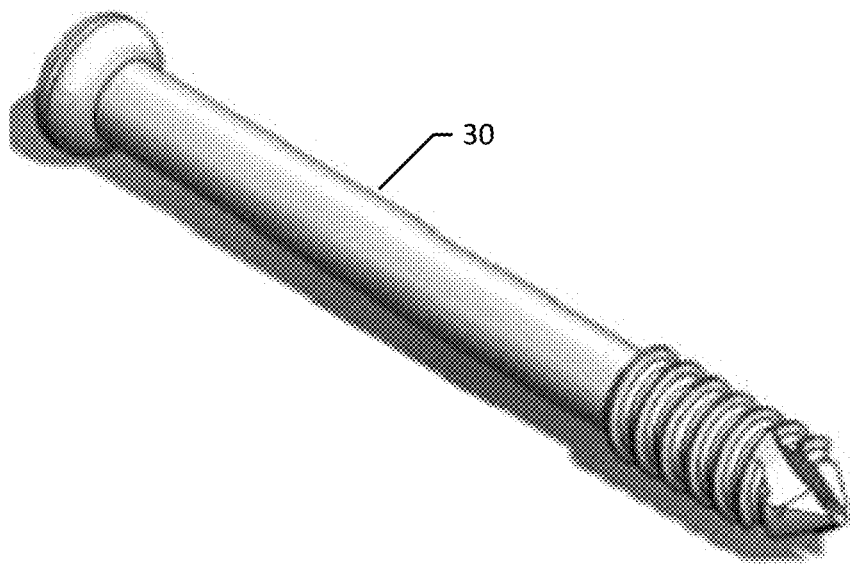
FIG. 15A is a distal perspective view of a lag-type screw.
Figure 15B:
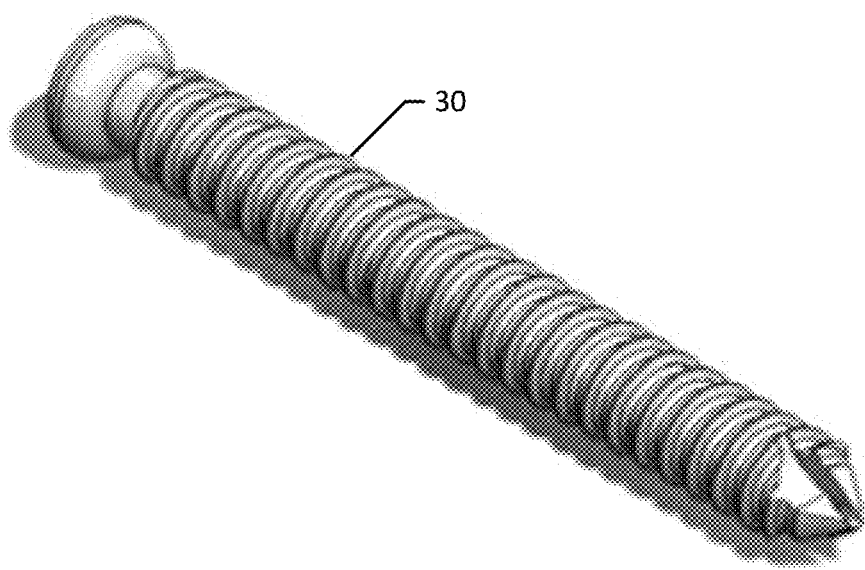
FIG. 15B is a distal perspective view of a fully threaded screw.
Figure 16:
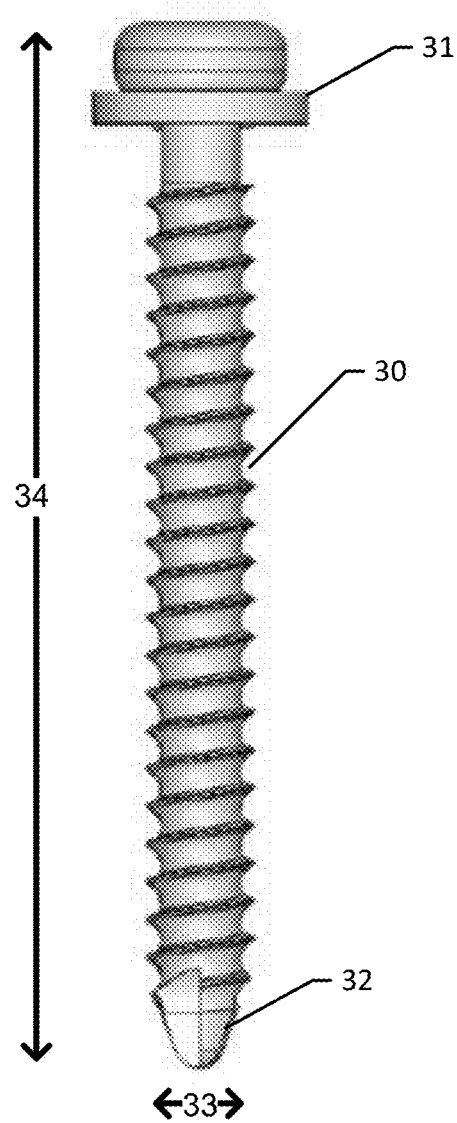
FIG. 16 is a side view of a fully threaded screw and a washer.

In various aspects, the anchor 30 and additional anchor 30A may be provided in the form of a screw. Referring to FIGS. 15A and 15B, each anchor 30 may be a "lag" type screw (FIG. 15A) which serve to pull the S1 joint together, or fully threaded (FIG. 15B) for capturing multiple cortices, enhancing stability. In other aspects, each anchor 30 may include a single lead or a dual lead. In yet other additional aspects, the anchor may be cannulated or non-cannulated. Referring to FIG. 16, the anchor 30 may be further provided with a washer 31 in various aspects. In various other aspects, the distal end 32 of the anchor 30 may include various features to enhance the function of the anchor 30 including, but not limited to, a self-tapping tip as illustrated in FIG. 16. In other aspects, each anchor 30 may include a single lead or a dual lead.

In various aspects, the anchor 30 may have an anchor diameter 33 ranging from about 4 mm to about 8 mm. In various aspects, anchor diameter 33 may range from about from about 4 mm to about 5 mm, from about 4.5 mm to about 5.5 mm, from about 5 mm to about 5.2 mm, from about 5.1 mm to about 5.3 mm, from about 5.2 mm to about 5.4 mm, from about 5.3 mm to about 5.5 mm, from about 5.4 mm to about 5.6 mm, from about 5.5 mm to about 5.7 mm, from about 5.6 mm to about 5.8 mm, from about 5.7 mm to about 5.9 mm, from about 6.0 mm to about 6.2 mm, from about 6.1 mm to about 6.3 mm, from about 6.2 mm to about 6.4 mm, from about 6.3 mm to about 6.5 mm, from about 6.4 mm to about 6.6 mm, from about 6.5 mm to about 6.7 mm, from about 6.9 mm to about 7.1, and from about 7 mm to about 8 mm. In various additional aspects, the anchor diameter 33 may be 4 mm, 4.5 mm, 5 mm, 5.5 mm, 6 mm, 6.5 mm, 7 mm, 7.5 mm, and 8 mm.

In various other aspects, the anchor 30 may have an anchor length 34 ranging from about 20 mm to about 80 mm. In various aspects, anchor length 34 may range from about from about 20 mm to about 30 mm, from about 25 mm to about 35 mm, from about 30 mm to about 40 mm, from about 35 mm to about 45 mm, from about 40 mm to about 50 mm, from about 45 mm to about 55 mm, from about 50 mm to about 60 mm, from about 55 mm to about 65 mm, from about 60 mm to about 70 mm, from about 65 mm to about 75 mm, and from about 70 mm to about 80 mm. In various additional aspects, the anchor length 34 may be 20 mm, 25 mm, 30 mm, 35 mm, 40 mm, 45 mm, 50 mm, 55 mm, 60 mm, 65 mm, 70 mm, 75 mm, and 80 mm.

In various other aspects, the anchor 30 may be provided in the form of a S2 alar iliac (S2AI) screw. In these aspects, the anchor 30 may by inserted in a medial-lateral fastener trajectory in which the anchor 30 may enter the bone of sacrum 1004 near the first sacral foramen (S2AI trajectory) then into or through graft window 40 and may further enter the bone of the ilium 1005. In an aspect, the anchor 30 may enter the sacrum 1004 just lateral to the lateral edge of the S1 foramen and, in some instances, generally superiorly-inferiorly even with the superior edge of the S1 foramen so as to mimic an S2 alar iliac pelvic fixation. In other aspects, the anchor 30 may penetrate the sacrum 1004 just lateral to the lateral edge of the S2 foramen and, in some instances, generally superiorly-inferiorly even with the superior edge of the S2 foramen.

The anchor 30 may be machined, molded, formed or otherwise manufactured from similar biocompatible materials. In one aspect, the implant 25 may be machined from a metallic implant alloy including, but not limited to a titanium-aluminum-vanadium ELI (Extra Low Interstitial) alloy (ASTM F136). In another aspect, the implant 25 may be machined from a polymer including, but not limited to a polyetheretherketone (PEEK) polymer such as ZENVIA ZA-500.

II. Delivery Tool

Referring again to FIG. 1, the system 10 for fusing a sacroiliac joint may include a delivery tool 20 to insert the implant assembly 15 into the sacroiliac joint (not shown) of a subject. The delivery tool 20 may include a distal end 35 and a proximal end 80. The distal end 35 may detachably support the implant assembly 25 during insertion into the joint space of the sacroiliac joint of the subject. The proximal end 80 may be configured to be grasped and manipulated to facilitate the insertion of the implant 25 into the sacroiliac joint.

Figure 17:
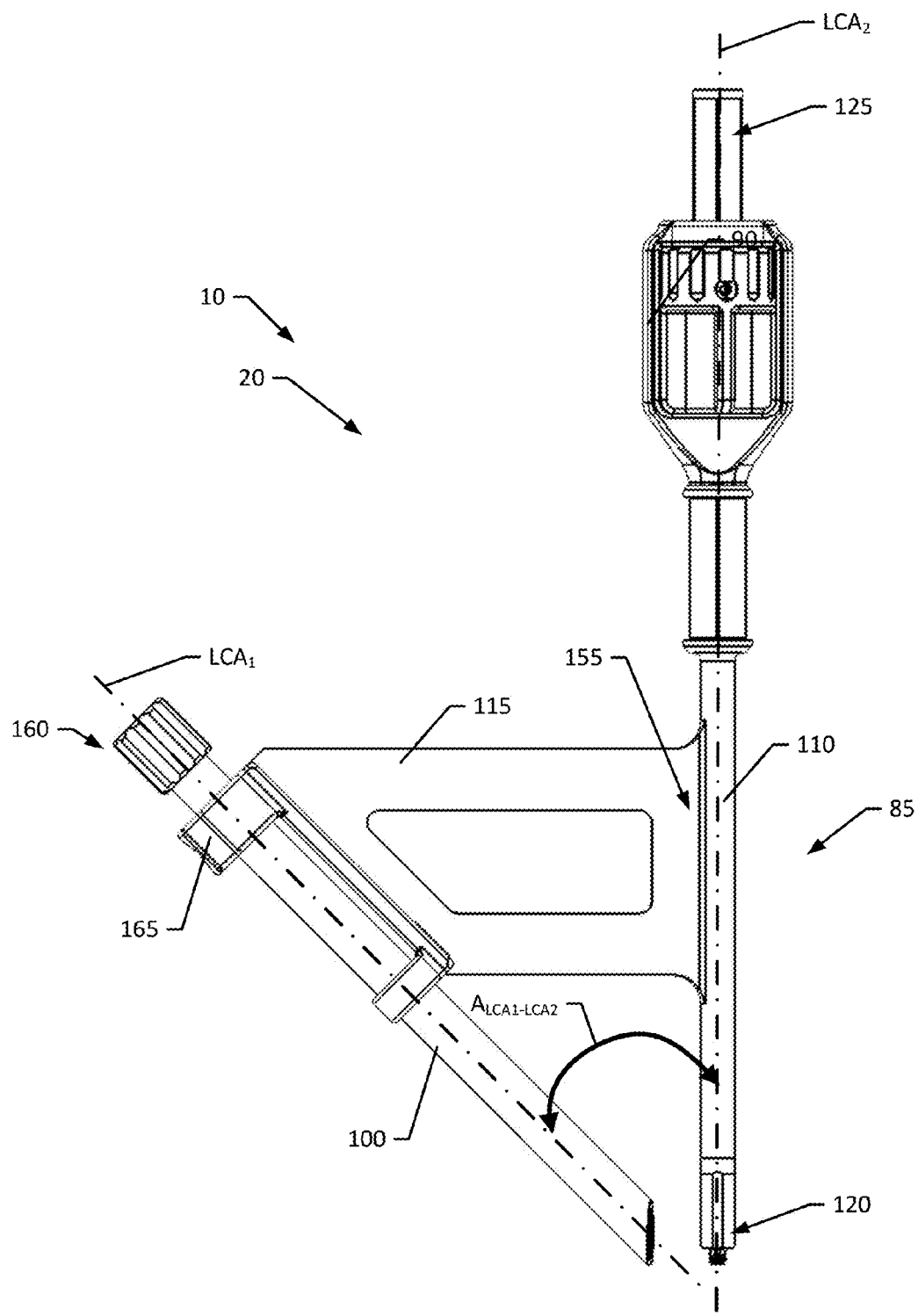
FIG. 17 is a side view of an implant assembly.
Figure 18:
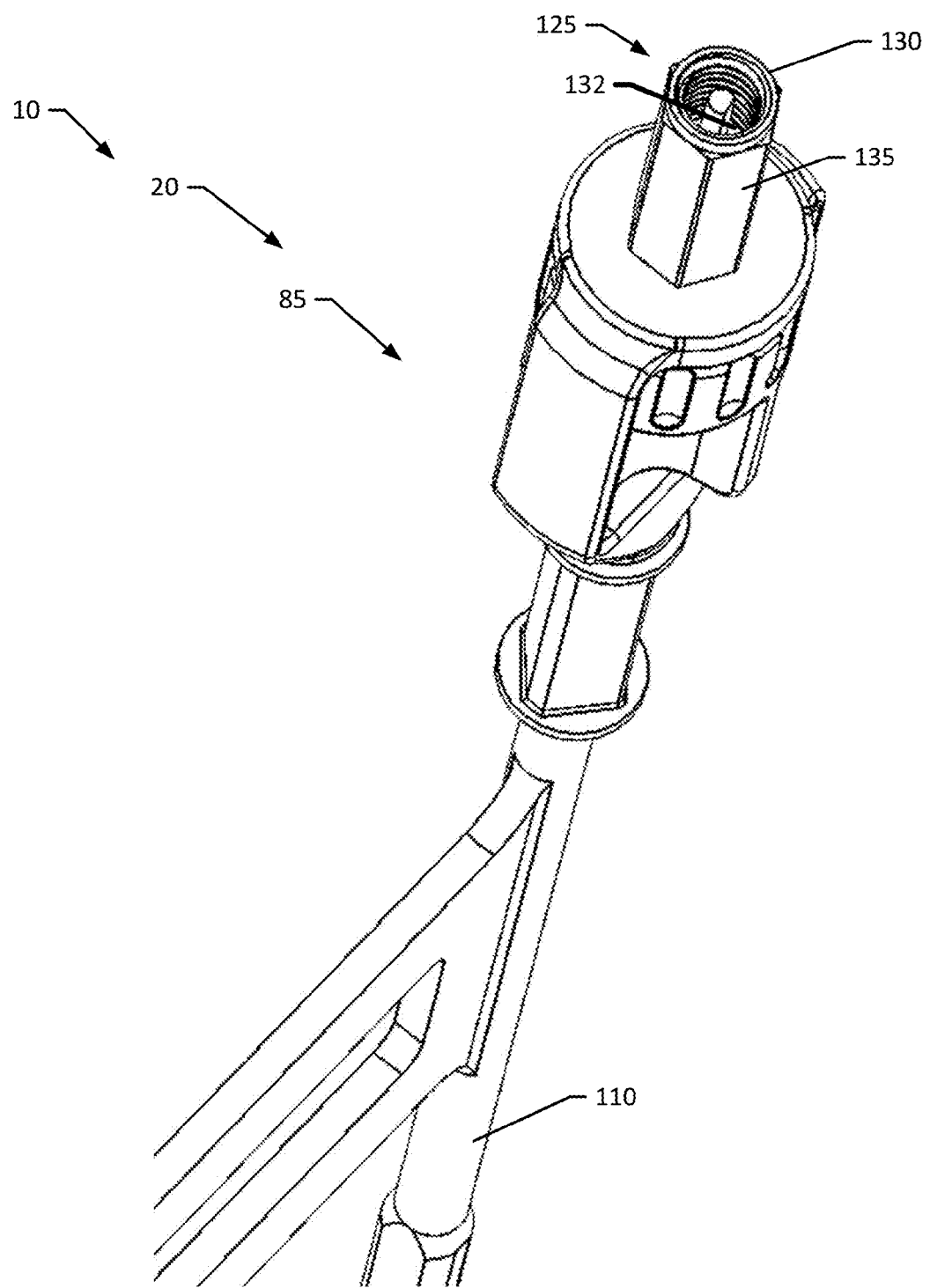
FIG. 18 is a proximal perspective view of an implant arm.

As illustrated in FIG. 1, the delivery tool 20 further includes an arm assembly 85 situated at the distal region of the tool 20, and a handle 90 attached at the proximal end 80 of the tool 20. Referring to FIG. 17, the arm assembly 85 may include an implant arm 110 and an anchor arm 115 supported off of the implant arm 110. The implant arm 110 includes a distal end 120 and a proximal end 125. Referring to FIG. 18, the proximal end 125 of the implant arm 110 may further include a proximal cylindrical opening 130 of a cylindrical bore 132. The proximal end 125 may also include a faceted outer surface configuration 135 that facilitates a mechanical engagement arrangement with the handle 90 (not shown) similar to a mechanical arrangement that exists between a wrench and nut.

Referring to FIGS. 19A-19C, the cylindrical bore 132 may extend the full length of the implant arm 110 from the proximal opening 130 to a distal opening 137. In an aspect, the cylindrical bore 132 may contain an implant retainer 95 attached to a retainer knob 96 contained within a frame 97 situated near the proximal end 125. In an aspect, the implant retainer 95 may extend distally along the cylindrical bore 132 and may end at a threaded shaft 220 protruding from the distal opening 137. Referring to FIGS. 11A and 11B, the threaded shaft 220 may be advanced into the threaded bore 446 of the implant 25 in order to retain the implant 25 on the distal end 35 of the delivery tool 20.

As can be understood from FIGS. 1 and 11B, when the system 10 is assembled for the delivery of the implant assembly 15 to the sacroiliac joint 1000, the proximal face 454 of the implant 25 is supported off of the implant arm distal end 120 (see FIG. 11B). Also, as shown in FIGS. 11A and 11B, when the system 10 is assembled for the delivery of the implant assembly 15 to the sacroiliac joint, the planar extreme proximal face 454 of the implant 25 abuts against the planar extreme distal face 152 of the implant arm distal end 120, the alignment protrusions 255A/255B being received in a recessed fashion in the alignment bores 452A/452B. The alignment protrusions 255A/255B being received in the alignment bores 452A/452B may prevent the implant 25 from pivoting relative to the implant arm 110. The alignment protrusions 255A/255B may be configured to have a rectangular, circular or any other cross section and the corresponding alignment bores 452A/452B may also be configured to have corresponding cross-sectional shapes.

Referring again to FIG. 17, the anchor arm 115 may be supported off of the implant arm 110 at an angle and includes a proximal end 155 attached to the anchor arm 110 and a distal end 160 distally terminating in a sleeve or collar 165 defining an anchor axis $LCA_1$ that is generally transverse to the longitudinal axis of the anchor arm 115. The collar 165 may be configured to permit and maintain accurate alignment of the first sleeve 100 along $LCA_1$ during the course of the procedure to install the implant assembly 15. The anchor arm proximal end 155 intersects the implant arm 110 at a location between the proximal end 125 and the distal end 120 of the implant arm 110.

As indicated in FIGS. 17 and 19, the implant arm 110 may also define an implant axis $LCA_2$. As shown in FIGS. 11A and 11B, when the implant 25 is mounted on the distal end 120 of the implant arm 110, the longitudinal center axis CA of the implant 25 is coaxially aligned with the longitudinal center axis $LCA_2$ of the implant arm 110. In addition, the anchor axis $LCA_1$ defined within the anchor arm collar 165 projects through the graft window 40, thereby assuring that the anchor 30 will pass through the graft window 40 without mechanical interference. Thus, the longitudinal center axis CA of the implant 25 and the implant axis $LCA_2$ of the implant arm 110 exist on a first common longitudinally extending axis, and the anchor axis $LCA_1$ of the anchor arm collar 165 passes through the graft window 40 as a result of the orientation of the anchor arm collar 165 and the implant arm 110 of the delivery tool 20. As a result, the delivery tool 20 enables the safe and accurate assembly of the implant assembly 15 within the sacroiliac joint 1000 of a subject without need for direct visual confirmation. By way of non-limiting example, the line of action for the insertion of the implant 25 into the sacroiliac joint 1000 is coaxial with the center axes of the implant 25, implant arm 110 and handle 90.

The use of the delivery tool 20 in various aspects results in a higher degree of accuracy and consistency in the implantation procedures, and further reduces invasiveness and potential for complications associated with performing an implantation procedure requiring direct visualization of the insertion of the anchor 30 through the implant 25. The anchor arm collar 165 is oriented so as to guide drills and other tools in creating a channel through tissue and bone leading to the graft window 40 when the implant 25 is positioned in the sacroiliac joint space 1044 while the implant 25 is still attached to the distal end 120 of the implant arm 110, as shown in FIG. 17. Additionally, the anchor arm collar 165 is oriented so as to guide the anchor member 30 into the graft window 40 when the implant 25 is positioned in the sacroiliac joint 1000 while the implant 25 is still attached to the distal end 120 of the implant arm 110, as shown in FIG. 1.

In one embodiment, the longitudinal center axis $LCA_1$ of the anchor arm collar 165 may form an angle $A_{LCA1\text{-}LCA2}$ with the longitudinal center axis $LCA_2$ of the implant arm 110, as illustrated in FIG. 17. In various aspects, the angle $A_{LCA1\text{-}LCA2}$ may range from about 15 degrees to about 135 degrees. In various other aspects, the angle $A_{LCA1\text{-}LCA2}$ may range from about 15 degrees to about 25 degrees, from about 20 degrees to about 40 degrees, from about 30 degrees to about 50 degrees, from about 40 degrees to about 60 degrees, from about 50 degrees to about 70 degrees, from about 60 degrees to about 80 degrees, from about 70 degrees to about 90 degrees, from about 80 degrees to about 100 degrees, from about 90 degrees to about 110 degrees, from about 100 degrees to about 120 degrees, from about 110 degrees to about 130 degrees, and from about 115 degrees to about 135 degrees. In various other aspects, the angle $A_{LCA1\text{-}LCA2}$ may be 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 110 degrees, 115 degrees, 120 degrees, 125 degrees, 130 degrees, and 135 degrees. In one aspect, the angle $A_{LCA1\text{-}LCA2}$ may be 45 degrees.

As can be understood from FIG. 17, in one aspect, the above-described coaxial and angular relationships may be rigidly maintained due to the anchor arm 115 and its collar 165 being in a fixed, non-adjustable configuration, and the interconnection between the proximal end of the anchor arm 115 and the implant arm 110 being a fixed, non-adjustable configuration, at least with respect to the angle $A_{LCA1\text{-}LCA2}$ between the longitudinal center axis $LCA_1$ of the anchor arm collar 165 and the longitudinal center axis $LCA_2$ of the implant arm 110. Thus, in one embodiment, the delivery tool 20 may be provided to a practitioner in a fixed, non-adjustable configuration having the coaxial and angular relationships articulated above with respect to FIG. 17.

a. Adjustable Anchor Arm

Figure 20:
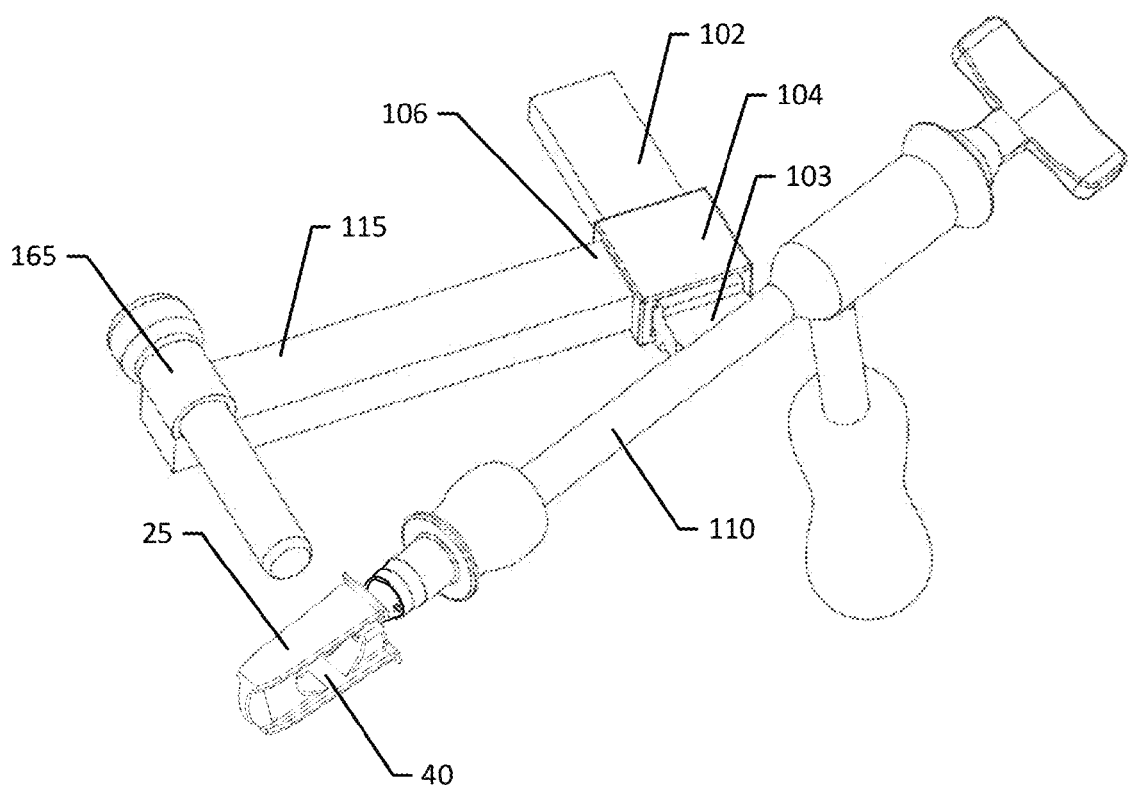
FIG. 20 is a perspective view of an adjustable delivery system with a slidable anchor arm.

In other aspects, the anchor arm 115 may be adjustable to accommodate patients of different sizes and/or fine-tune the anchor trajectory while still maintaining the angular relationships between the components of system 10 within a predefined range allow the anchor 30 to be delivered through the graft window 40 without any further adjustment to the delivery tool 20. As illustrated in FIG. 20, the anchor arm 115 may be slideably attached at one end to a guide beam 102. The guide beam 102 may be attached to the implant arm 110 at one end 103 and protrude from the implant arm 110 in a cantilevered configuration, wherein the protrusion angle of the guide beam 102 is configured to result in a predetermined anchor entry angle through the implant 25. The anchor arm 115 may be provided with a slideable fitting 104 at an end 106 opposite to the anchor arm collar 165. In this aspect, the slideable fitting 104 may be translated along the guide beam 102 to adjust the distance between anchor arm collar 165 and implant 25, while maintaining the angular relationships maintained between the implant arm 110, anchor arm 115, anchor arm collar 165, and the graft window 40.

Figure 21:
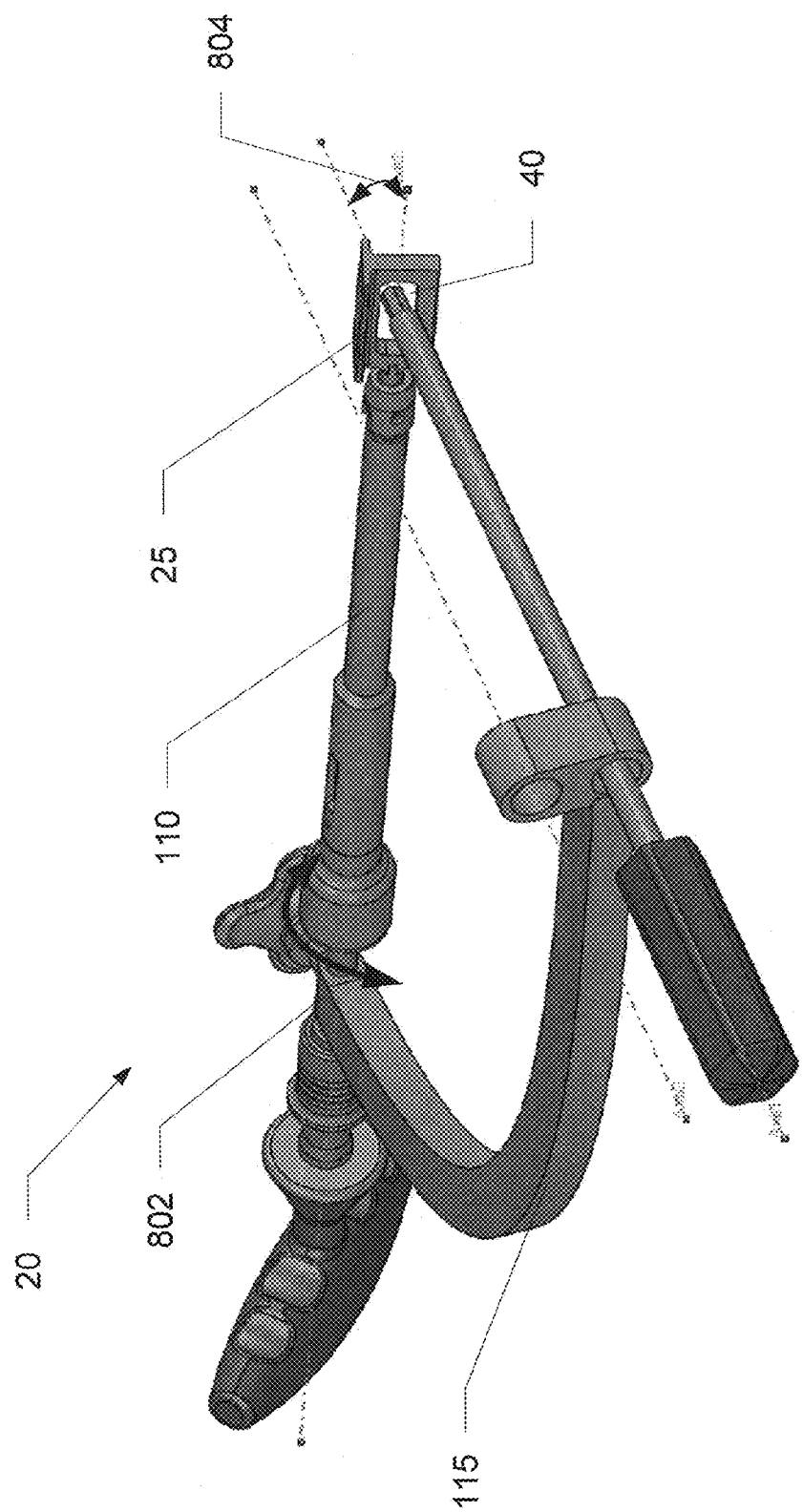
FIG. 21 is a perspective view of an adjustable delivery system with a rotating coupling to rotate the anchor arm around the implant arm axis.

Another embodiment of an adjustable delivery tool 20 is illustrated in FIG. 21. Referring to FIG. 21, the delivery tool 20 may include an anchor arm 115 attached at one end to the implant arm 110 in a rotating joint 802 configured to rotate the anchor arm 115 about the longitudinal axis of the implant arm 110 while maintaining an anchor trajectory that includes passing an anchor 30 through the graft window 40 of the implant 25. Opposite the rotating joint 802 is an anchoring guide that is configured to guide the insertion of an anchor 30 within the graft window 40. The anchoring guide may, for example, include a plurality of slots or guide holes that guide an anchor 30 or a shaft of a tool that is coupled with an anchor 30.

Stated another way, the anchor arm 115 may rotate or, conversely, the implant arm 110 may rotate within a range of trajectories that are each configured to pass an anchor 30 through the graft window 40. Additionally, the anchor arm 115, or, more particularly, the rotating joint 802 may restrict or limit the range of trajectories to a particular range of trajectories that will align the anchor 30 with the graft window 40 such that the anchor arm 115 may only rotate within the particular range. In this way, trajectories will not be chosen that result in errant placement of the anchor 30 in places other than the graft window 40. The rotation can be mechanically restricted or limited with a stop element or other mechanical feature.

In various aspects, the angle 804 that the anchor trajectory makes relative to a perpendicular trajectory through the graft window may range from about −30 degrees to about +30 degrees. In other embodiments, however, the range may be from about −5 degrees to about +5 degrees or −10 degrees to about +10 degrees, among other ranges.

Figure 22:
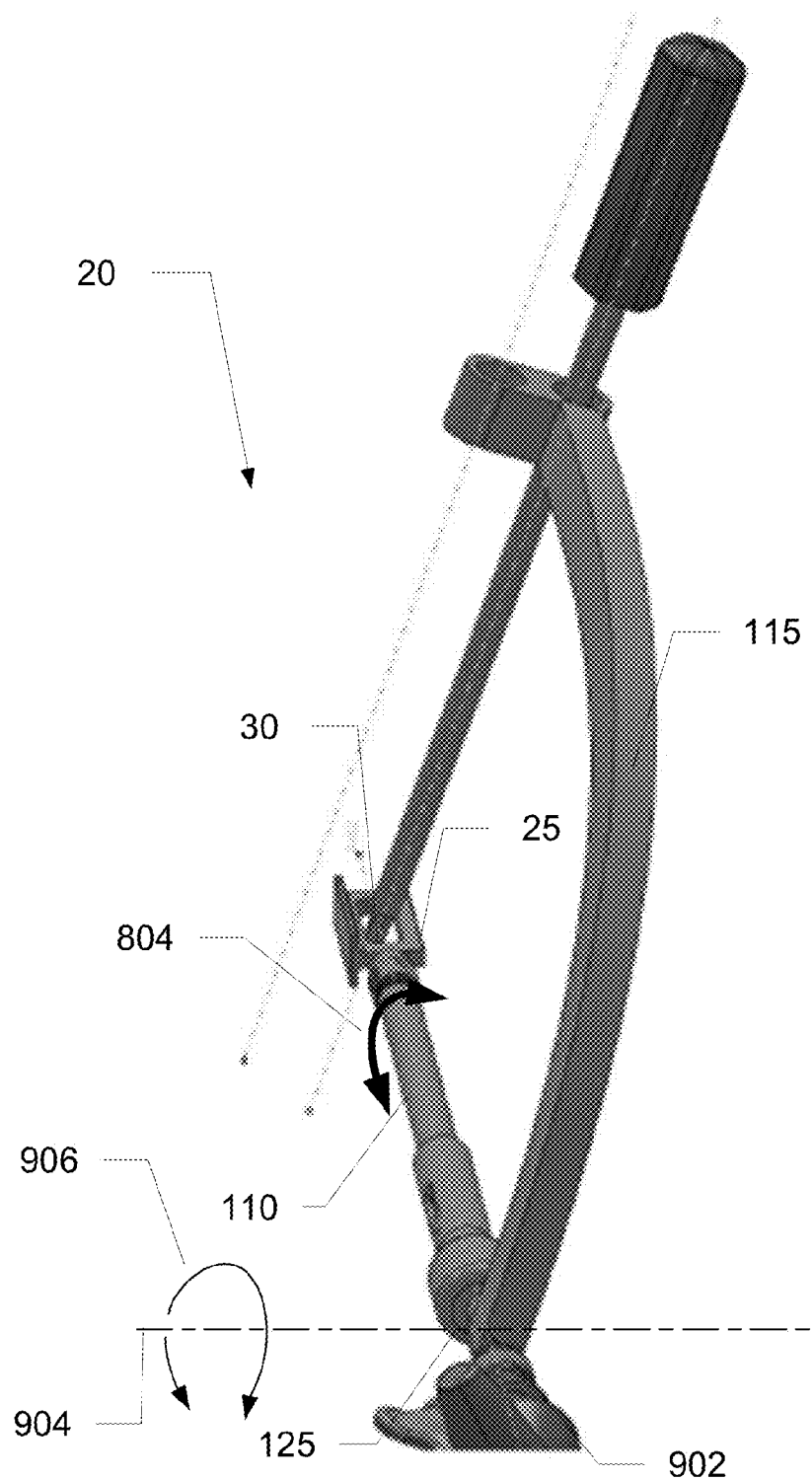
FIG. 22 is a perspective view of an adjustable delivery system with a rotating coupling to rotate the anchor arm around the implant arm and the implant arm about an axis mutually perpendicular to the implant arm and the anchor arm.

In this embodiment, the rotating joint 802 provides the capability to adjust the anchor trajectory within a predetermined envelope while restricting the anchor arm 115 from rotating to trajectories that are outside of the predetermined envelope. This predetermined envelope may be sized to ensure that the anchor trajectory passes through the graft window 40 while allowing a practitioner a limited amount of leeway to adjust the anchor trajectory as needed for each surgical procedure Referring to FIG. 22, the proximal end 125 of the implant arm 110 may attach to the anchor arm 115 using a rotating joint 902 such that the implant arm 110 may pivot or rotate about an axis 904 perpendicular to the plane formed by the anchor arm 115 and implant arm 110 within a predetermined angular range 906. In this way, the anchor arm 115 may pivot about the axis 904 such that the anchor 30 may be delivered through the graft window 40 in various orientations. For example, as seen in FIG. 22, the anchor 30 is substantially perpendicular to a plane formed by the graft window 40. The anchor arm 30 may, however, be rotated clockwise about the axis 904 such that a distal end of the anchor 30 angles more towards a distal end of the graft window 40. Conversely, the anchor arm 30 may be rotated counterclockwise about the axis 904 such that a distal end of the anchor 30 angles more towards a proximal end of the graft window 40. In this embodiment, this angular range 906 may modify the trajectory of the anchor 30 or other fastener by inserting or withdrawing the anchor 30 slightly as well as changing the angle 804 of the anchor trajectory measured in the plane formed by the anchor arm 115 and implant arm 110. Other rotating attachments between other elements of the delivery tool 20 may be incorporated in additional embodiments without limitation. For example, the rotating joint 902 may rotate about the axis 904 and the axis defined by the longitudinal axis of the implant arm 110. Or, the rotating joint may only rotate about either the axis 904 or the axis defined by the longitudinal axis of the implant arm 110.

While the anchor arm 115 of FIGS. 21-22 is depicted as being arcuate, other designs are possible and contemplated herein. The anchor arm 115 may, for example, be a single straight member or may include multiple members of differing shapes. As another example, the anchoring arm 115 may include telescoping members that enable retraction and extension of an inner telescoping member.

Figure 23:
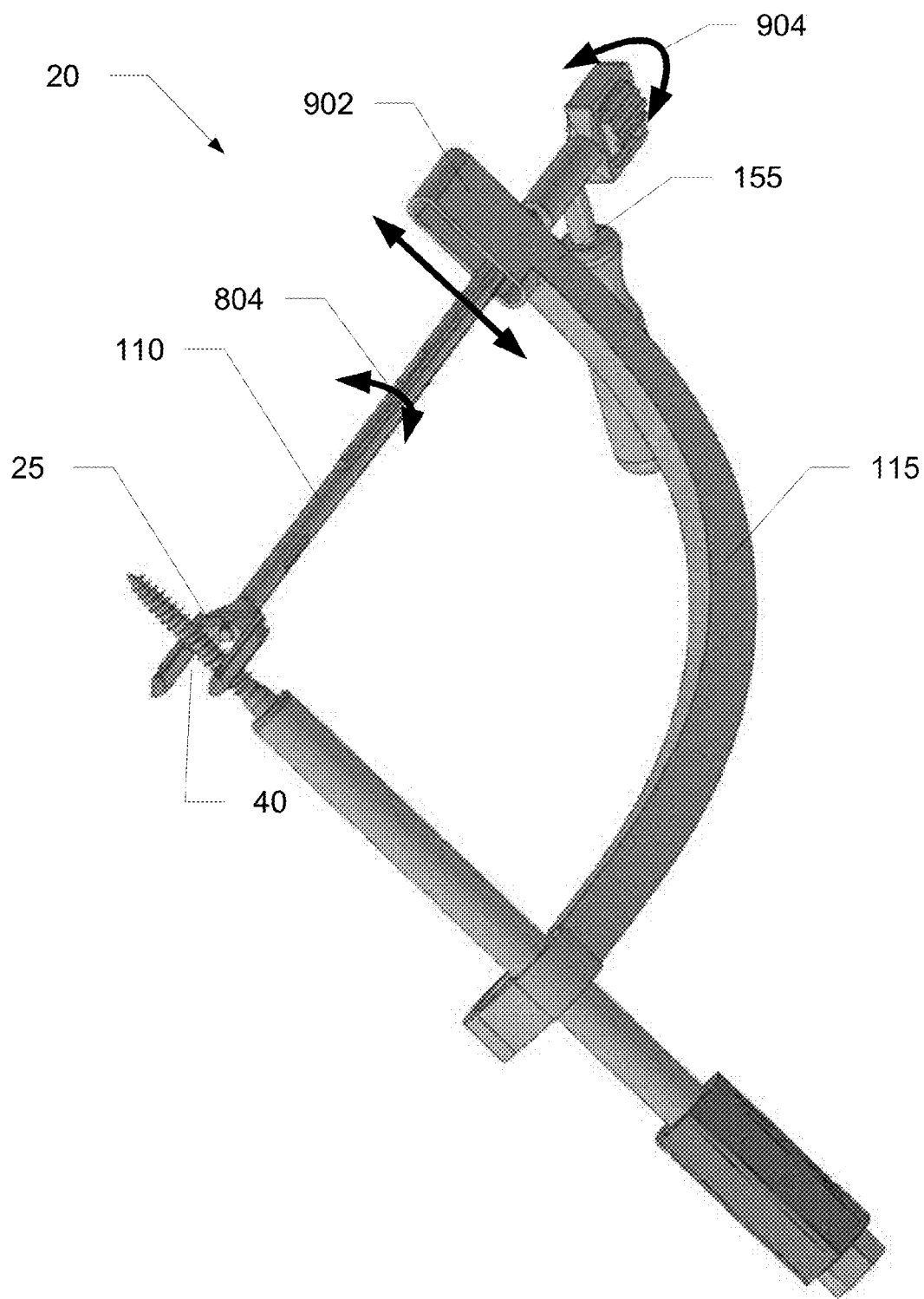
FIG. 23 is a perspective view of an adjustable delivery system with a cam and channel coupling between the anchor arm and the implant arm.
Figure 24:
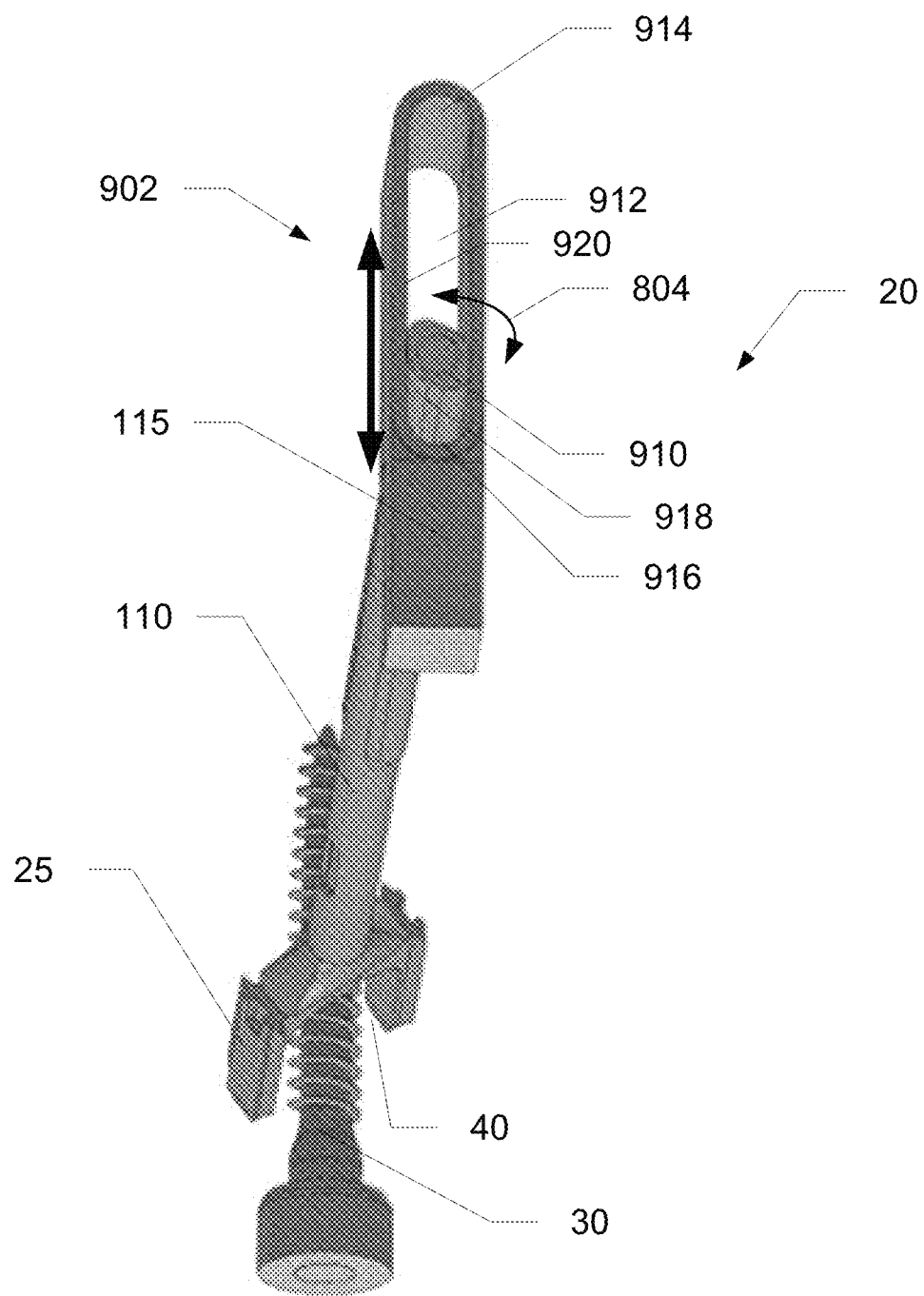
FIG. 24 is a section perspective view of an adjustable delivery system with a cam and channel coupling between the anchor arm and the implant arm.

Referring to FIGS. 23-24, in one aspect the rotating joint 902 may be provided in the form of a cam 910 engaged within a channel 912 formed within the proximal end 155 of the anchor arm 115. In this aspect, the cam 910 may slide and pivot along the channel to effectuate rotations about an axis 904 perpendicular to the plane formed by the anchor arm 115 and implant arm 110. In addition, the cam 910 may twist within the channel 912 to effectuate rotations 804 about the axis of the implant arm 110. The cam 910, as seen in FIG. 24, has a limited ability to rotate within the channel because the cam-shape inhibits full rotation of the cam 910 within the channel 912. And since the cam 910 is attached to the implant arm 110, the implant arm correspondingly includes a limited range of rotation 804 relative to the anchor 30. Additionally, the range of rotation about the axis 904 may be limited by the channel ends 914/916. The range of rotation 804 may be limited by the mechanical interference of the cam outer wall 918 with the inner wall 920 of the channel 912. The limited range of rotation is configured to allow an appropriate orientation of the anchor 30 relative to the graft window 40 in any of the limited ranges of rotation. Thus, the limited range of rotation limits the arrangement of the anchor 30 and graft window 40 to orientations that will not cause interference between the two.

It is noted that the embodiment of the insertion tool 20 in FIGS. 23-24 is configured to allow for insertion of the anchor 30 prior to the insertion of the implant 25. In certain implementations, however, the implant 25 may be inserted prior to the anchor 30.

Figure 25A:
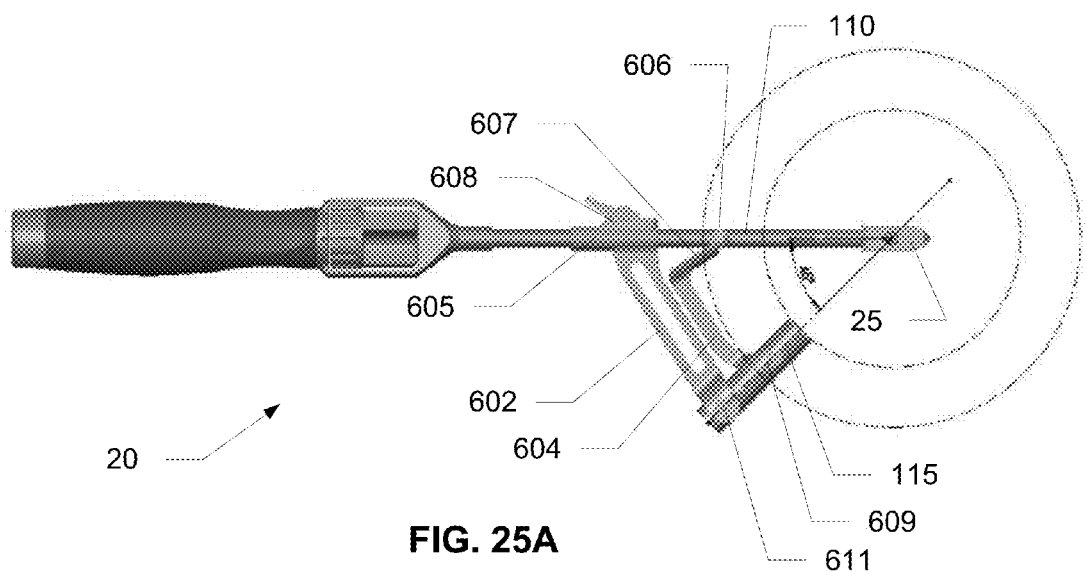
FIG. 25A is a side view of an adjustable delivery system with an articulating anchor arm in a first position.
Figure 25B:
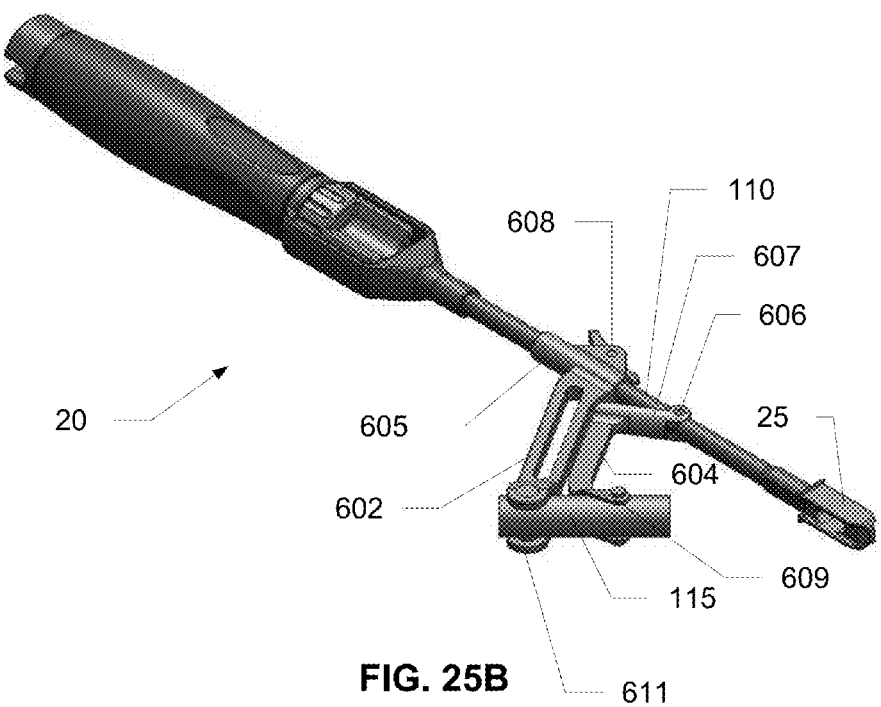
FIG. 25B is an isometric view of the adjustable delivery system with the articulating arm in the first position.
Figure 25C:
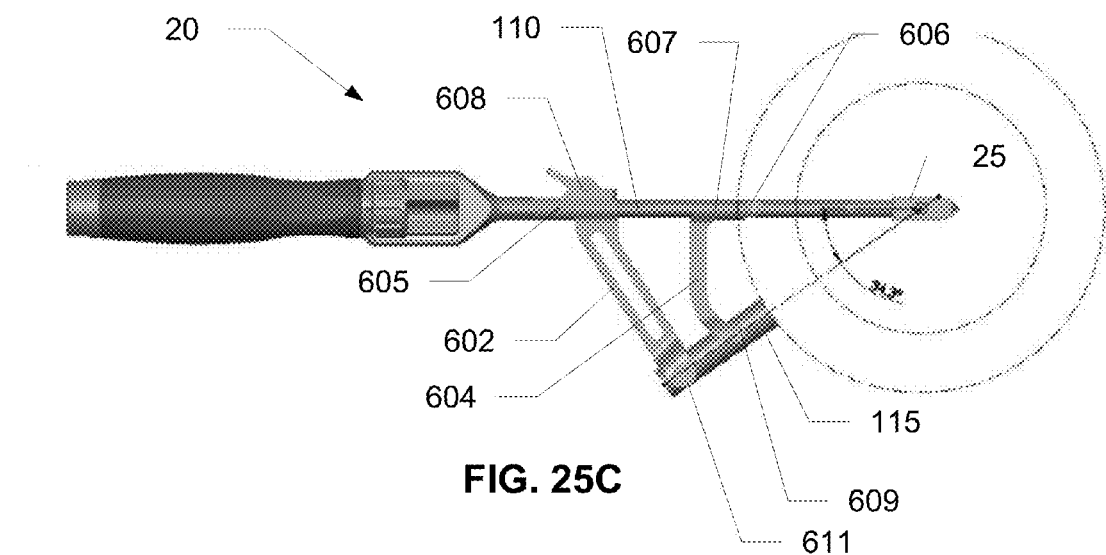
FIG. 25C is a side view of the adjustable delivery system with an articulating arm in a second position.
Figure 25D:
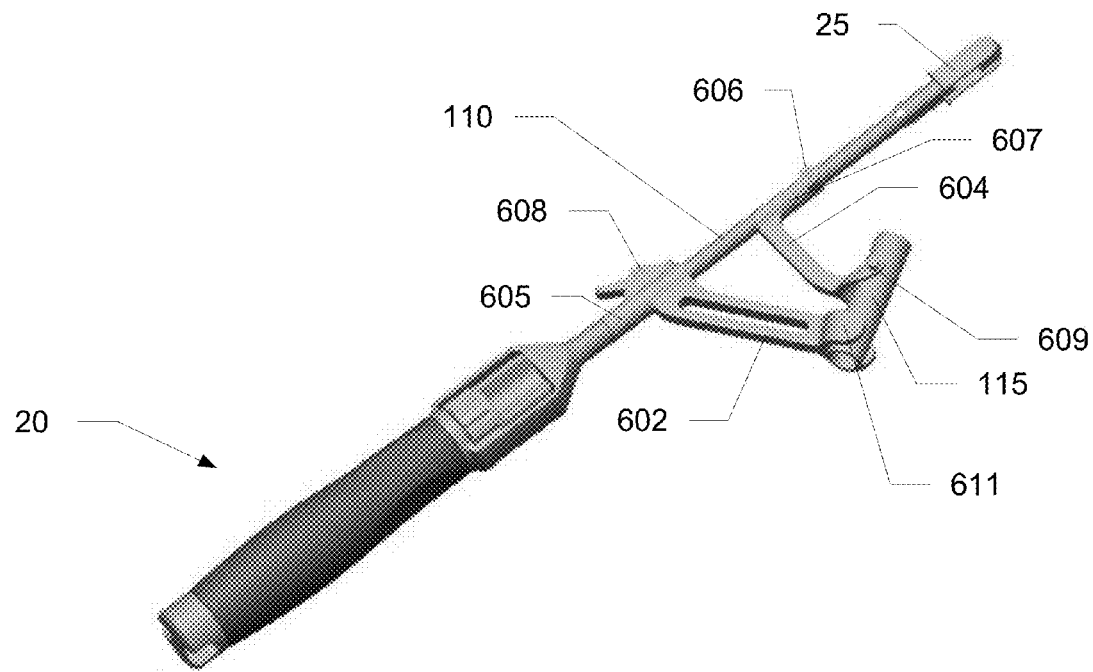
FIG. 25D is an isometric view of the adjustable delivery system with an articulating arm in a second position.
Figure 25E:
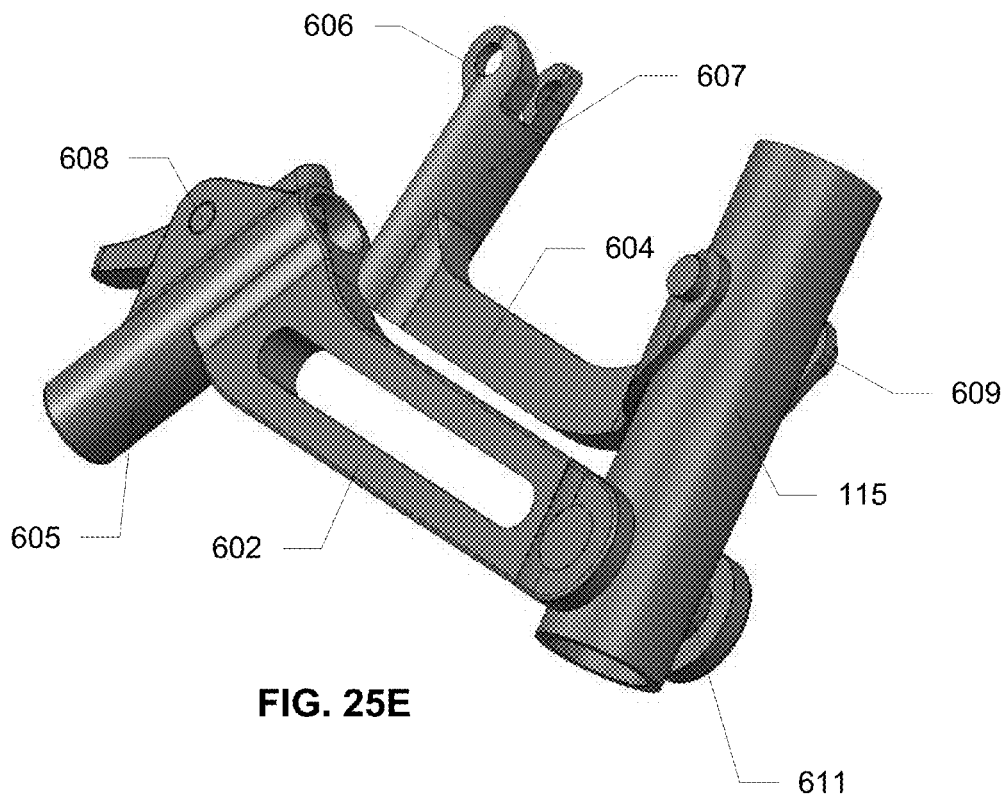
FIG. 25E is an isometric view of the articulated members and the anchor arm of the adjustable delivery system.
Figure 25F:
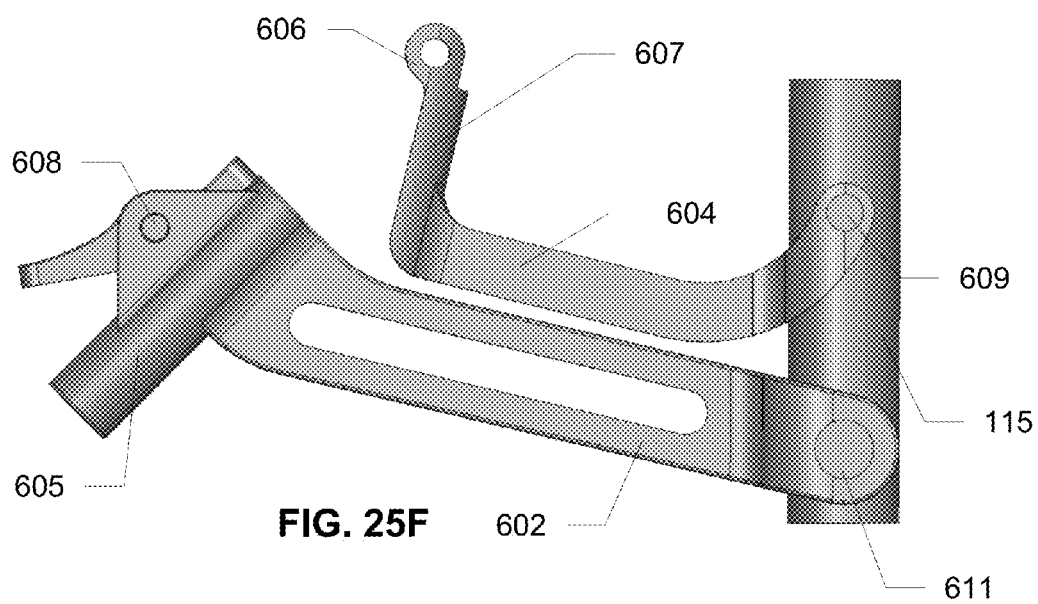
FIG. 25F is a side view of the articulated members and the anchor arm of the adjustable delivery system.
Figure 25G:
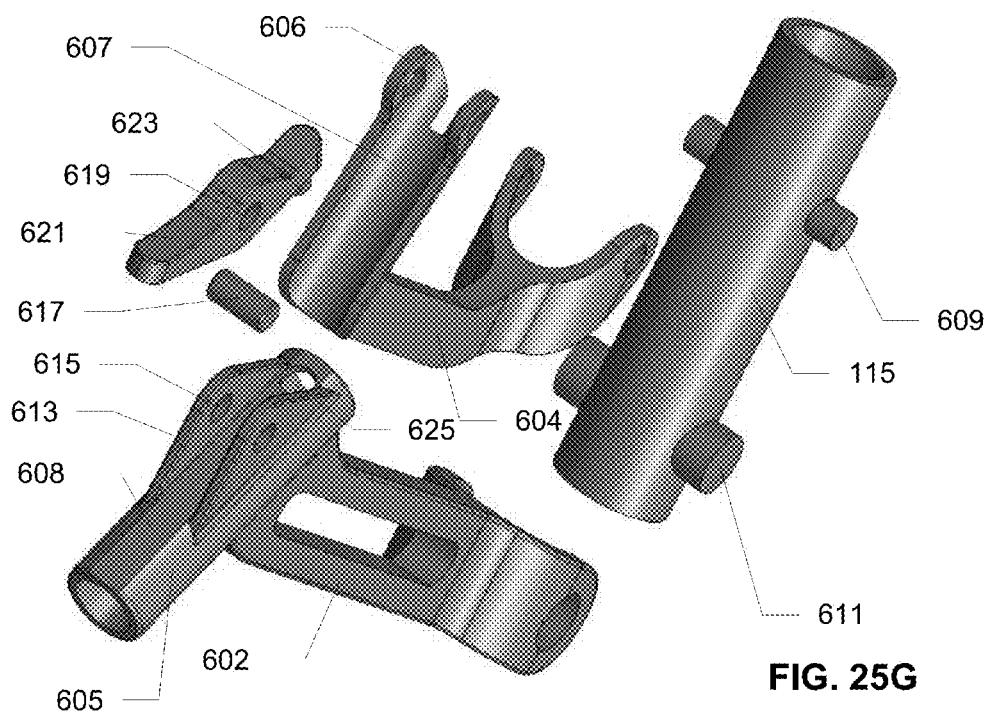
FIG. 25G is an exploded isometric view of the articulated members and the anchor arm of the adjustable delivery system.
Figure 25H:
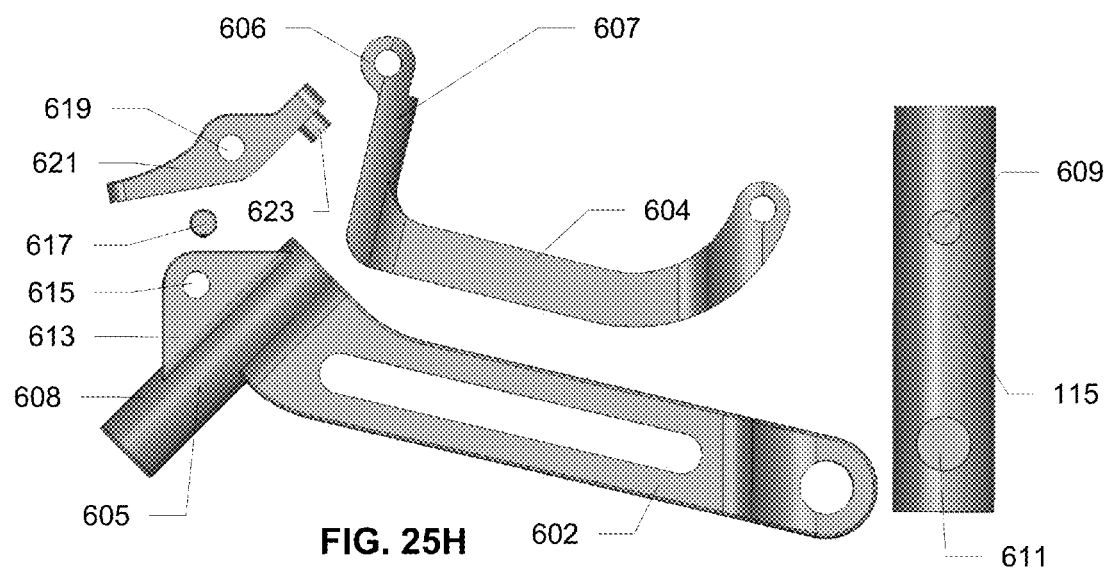
FIG. 25H is an exploded side view of the articulated members and the anchor arm of the adjustable delivery system.

Another embodiment of an adjustable delivery tool 20 is provided in FIGS. 25A-25H. Referring to FIG. 25A, the anchor arm 115 may be provided in the form of two or more articulated members 602 and 604. In this aspect, the articulating members 602 and 604 may be constrained to move between one of two locked positions: 1) a default position characterized by a 45 degree angle between the axes of the implant arm 110 and anchor arm 115, respectively as seen in FIGS. 25A and 25B; and 2) a high BMI position, as seen in FIGS. 25C and 25D, characterized by a 35 degree angle between the axes of the implant arm 110 and anchor arm 115, respectively and a higher lateral separation distance between the implant 25 and the anchor arm 115. The articulated members 602 and 604 may be attached to the anchor arm 115 by rotatable pin joints at one end, and to the implant arm 110 by a lockable sliding joint 608 and a rotatable pin joint 606, respectively. As seen in the figures, the anchor arm 115 is a tubular member pivotally coupled with the articulated members 602 and 604 at a distal point 609 and a proximal point 611, respectively. Referring to FIGS. 25G and 25H, the articulated arms 602 and 604 include U-shaped ends having through-holes that receive pegs on the anchor arm 115. Also as seen in FIGS. 25G and 25H, the sliding joint 608 includes a pair of flanges 613 extending parallel with each other and outward from the tubular member 605. Each of the flanges 613 include a through-holes 615 coaxially aligned with each other and designed to receive a pin 617 through the holes 615 as well as a through-hole 619 in a locking tab 621. The locking tab 621 includes a protrusion 623 on a bottom side thereof that is received in a corresponding opening 625 in the tubular member 605. The protrusion 623 may contact an outer surface of the implant arm 110 to stop the sliding joint 605 in the distal-most position and the proximal-most position. To move the sliding joint 605 between positions, the locking tab 621 may be depressed on a proximal end of the tab 621 and pivoted about the pin 617 so the protrusion 623 is removed from contact with the surface of the implant arm 110. In use, the lockable sliding joint 608 may be unlocked and slid to a distal-most position to assume the default position, and slid to an proximal-most position to assume the high BMI position. Because of the coupling aspect of the articulating members 602 and 604, as the lockable sliding joint 608 slides to the distal-most position, as seen in FIGS. 25A-25B, the anchor arm 115 moves distally and rotates counterclockwise. Moving from the distal-most position, as seen in FIGS. 25A-25B, to the proximal-most position, as seen in FIGS. 25C-25D, the lockable sliding joint 608 slides proximally and the anchor arm 115 moves proximally and rotates clockwise.

The articulating member 602 includes a tubular member 605 with an inner diameter that is slightly larger than an outer diameter of the implant arm 110. The relative difference in diameters facilitates the sliding of the sliding joint 608. And, the articulating member 604 includes a partial tubular member 607 that rotates about the rotatable pin joint 606 at one end of the partial tubular member 607. The partial tubular member 607 acts as a stop that inhibits rotation of the member about the rotatable pin joint 606 past a point where the partial tubular member 607 contacts the implant arm 110. Thus, in the BMI position, the partial tubular member 607 matingly contacts the tubular shaft of the implant arm 110 and inhibits further proximal sliding of the lockable sliding joint 608. In this way, the angle of the anchor arm 115, in the BMI position, is fixed by the inhibition of the partial tubular member 607 to rotate further.

b. Multiposition Anchor Guides

Figure 26:
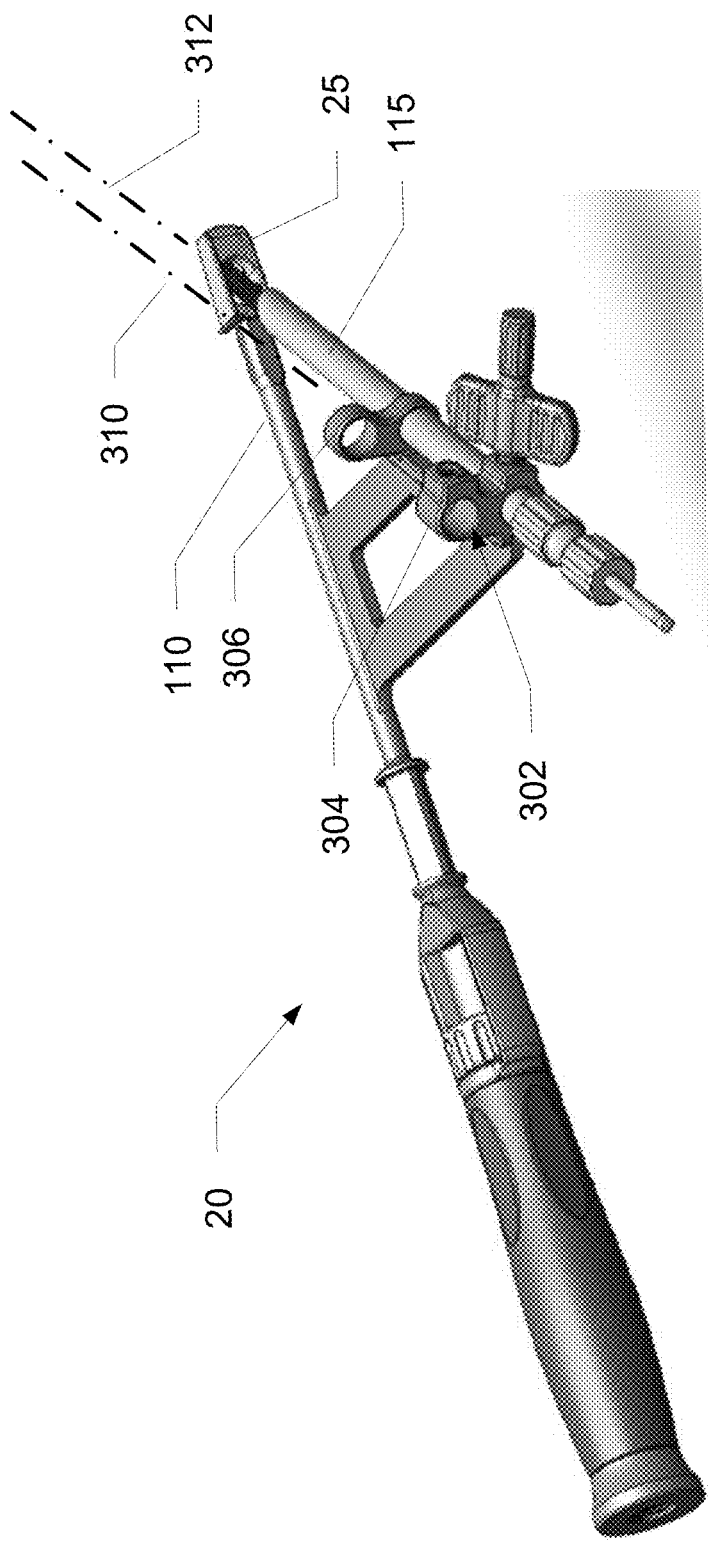
FIG. 26 is a perspective view of a delivery system with a modular anchor guide.

Referring to FIG. 26, the anchor arm 115 may be configured to deliver the anchor 30 along a first predetermined anchor trajectory through the graft window 40 of the implant 25 as well as at least one additional anchor 30A along at least one additional anchor trajectory. In one aspect, illustrated in FIG. 26, the delivery tool 20 may further include a modular anchor guide 302 attached to the anchor arm 115 of the delivery tool 20. In this embodiment, the modular anchor guide 302 may include two or more collars 304 and 306 separated along the length of the anchor arm 115 such that the centerlines of the two or more collars 304 and 306 are laterally offset and aligned with the longitudinal axis 312 of the anchor arm 115. In this aspect, the two or more collars 304 and 306 may provide a second trajectory 310 that may be aligned but offset from the longitudinal axis 312 of the anchor arm 115. This second trajectory 310 may be used to guide the path of various surgical tools and/or components including, but not limited to: an additional anchor 30A, a guidewire, a drill, a needle, a therapeutic compound, or any other surgical tool.

Figure 27:
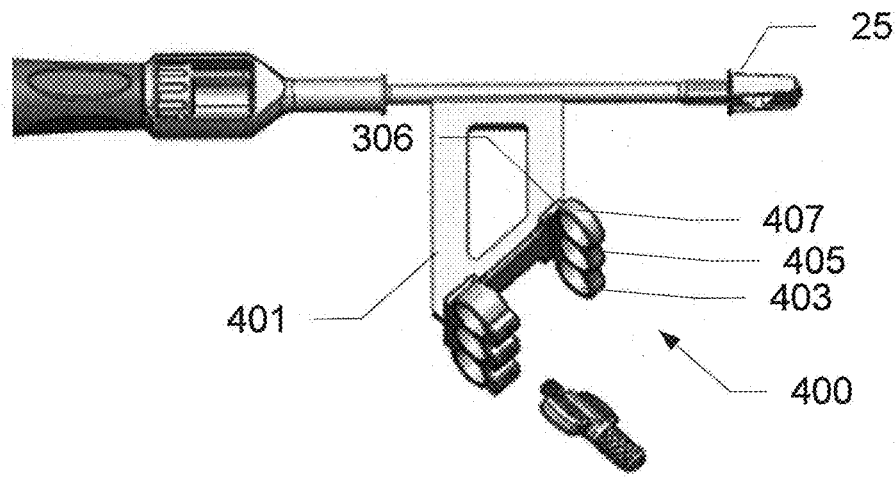
FIG. 27 is a side view of a delivery system with a multi-position anchor arm.
Figure 28:
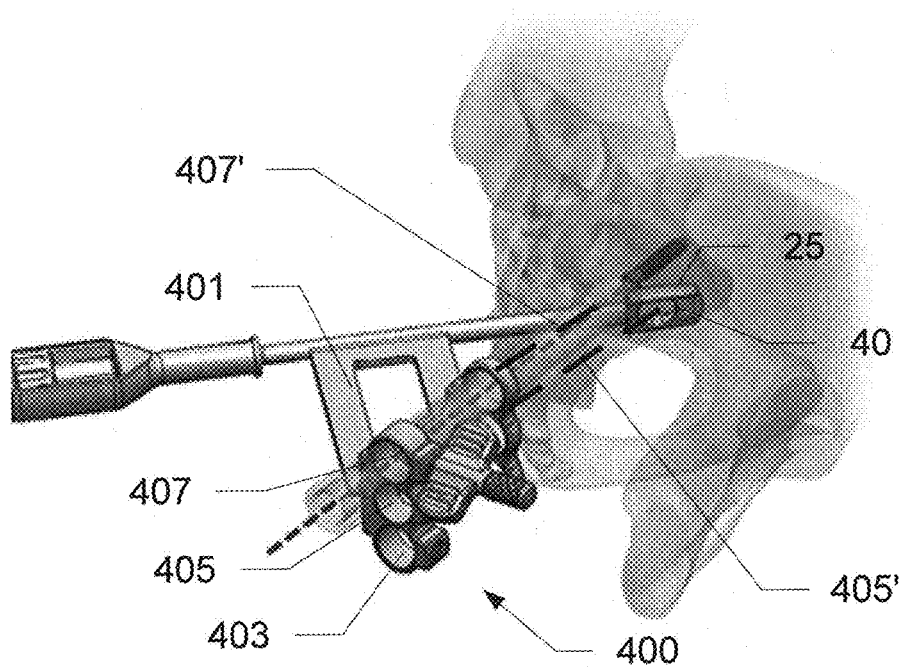
FIG. 28 is a perspective view of a delivery system with a multi-position anchor arm during an insertion of an implant assembly into a sacroiliac joint.

Referring to FIG. 27, the delivery tool 20 may further include an anchor arm 401 that distally ends in a multi-position anchor guide 400 in an aspect. The multi-position anchor guide 400 may include two or more guides 403, 405, and 407 that may be laterally offset and aligned along parallel trajectories. In use, the two or more anchor guides 403, 405, and 407 may be offset in an approximately dorsal-ventral direction to implement the insertion of an additional anchor dorsal to or ventral to the implant 25, as illustrated in FIG. 28 by way of non-limiting example. As illustrated in FIG. 28, the center guide 405 may define a center trajectory 405' directed though the graft window 40 of the implant 25 and the cephalad guide 407 may define a cephalad trajectory 407' that is aligned with the center trajectory 405' but passes cephalad to the implant 25. By way of non-limiting example, an anchor 30 and a second anchor 30A may be inserted along the center trajectory 405' and the cephalad trajectory 407' using the multi-position anchor guide 400 illustrated in FIG. 28, resulting in an implant assembly similar to that illustrated in FIG. 14. The multi-position guide 400 may compatible with a variety of surgical tools and/or components including, but not limited to: an additional anchor 30A, a guidewire, a drill, a needle, a therapeutic compound, or any other surgical tool. The surgical tools and/or components may be used to perform a variety of steps in a surgical procedure as described herein below.

c. Auxiliary Guide Arm

Figure 29:
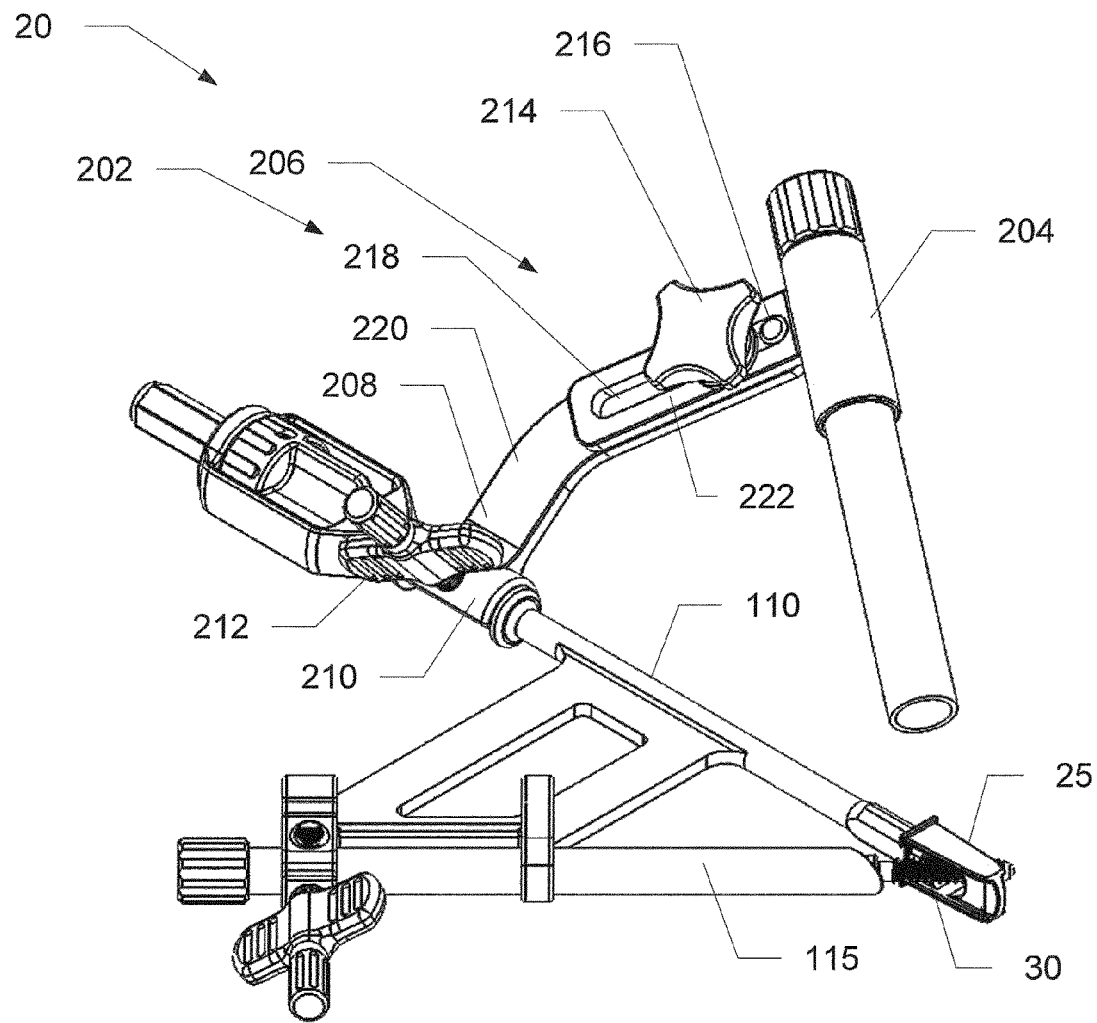
FIG. 29 is a perspective view of a delivery system with an adjustable auxiliary guide arm.

Referring to FIG. 29, the system 10 may further include an auxiliary guide arm 202 that may be used with one or more embodiments described herein. In one aspect, illustrated in FIG. 29, the auxiliary guide arm 202 may be attached at a proximal end 208 to a proximal portion of the implant arm 110. In various aspects, the auxiliary guide arm 202 may be adjustable in at least one degree of freedom. By way of non-limiting example, the auxiliary guide arm 202 may be attached to the implant arm 110 using a rotatable collar 210 that may permit the rotation of the auxiliary guide arm 202 about the longitudinal axis of the implant arm 110, and may further be provided with a locking mechanism such as a set screw 212 to lock the rotatable collar 210 in place. By way of another non-limiting example, the auxiliary guide arm 202 may be segmented with an adjustable joint between segments such as a sliding joint 206 that includes a post 216 projecting from a stationary element 224 situated within a channel 218 formed within a sliding element 222 that may be locked into place using a second locking mechanism such as a second set screw 214 to compress the sliding element 222 against the stationary element 224 when the second set screw is tightened down.

The auxiliary guide arm 202 may be further provided with an auxiliary guide collar 204 configured to guide a variety of tools and devices along a repeatable trajectory during a surgical procedure. In one non-limiting example, the auxiliary guide collar 204 may guide an additional anchor 40A or other fastener along a trajectory suitable for facilitating the anchoring of the implant 25 during a surgical procedure. In another aspect, the auxiliary guide collar 204 may guide a needle or other device into a marrow region of surrounding bone tissue; in this example, the needle may be used to extract bone paste or other biocompatible materials for use in the surgical procedure as described herein below.

d. Bone Paste Insertion Element

Figure 30:
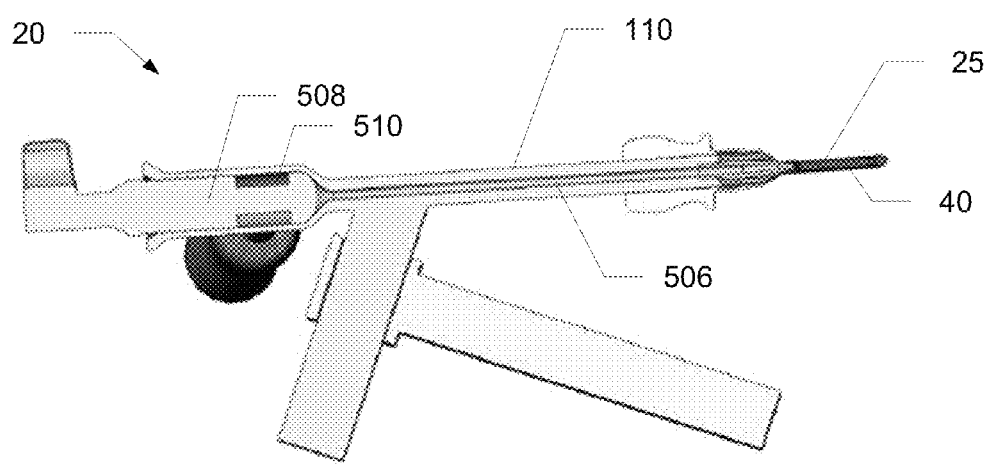
FIG. 30 is a side cross-sectional view of a delivery tool with a bone paste insertion element.

Referring now to FIG. 30, the delivery tool 20 may be further configured to inject a bone paste material, or any other biocompatible material into an implant 25. In one aspect, the implant arm 110 may be provided with a conduit 506 that opens into the graft window 40 of the implant 25. As illustrated in FIG. 30, the proximal end of the conduit 506 may be provided with a plunger 508 that may be depressed distally within a close-fitting barrel 510 formed within the proximal end 80 of the implant arm 110. The plunger 508 may provide a pressure that may cause the bone paste material or other biocompatible material to flow distally through the conduit 506 and out into the graft window 40 of the implant 25.

Figure 31:
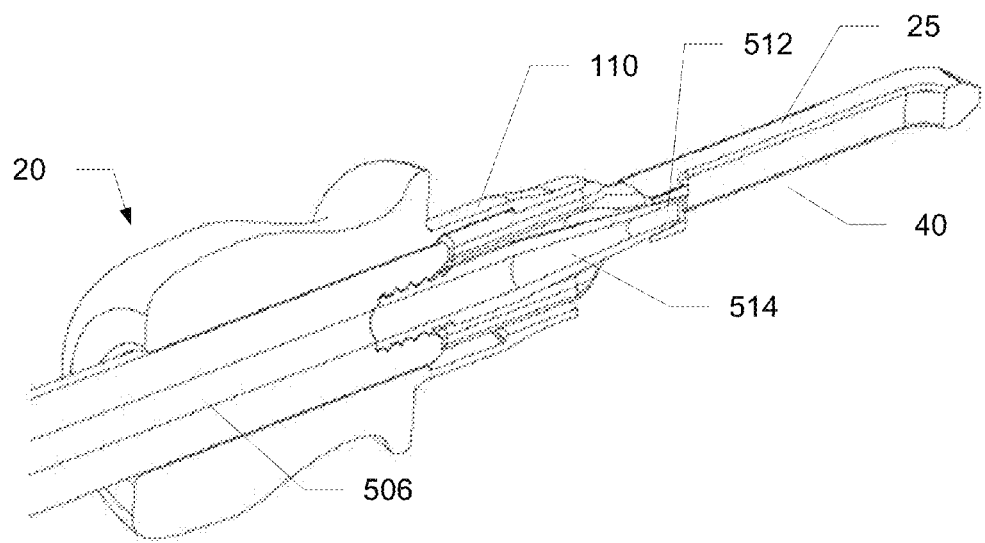
FIG. 31 is a perspective cross-sectional view of a delivery tool with a bone paste insertion element.

Referring now to FIG. 31, the conduit 506 may terminate distally at a distal opening 512 that provides a path for the bone paste material to pass into the graft window 40 of the implant 25. In an aspect, the conduit 506 may narrow in a nozzle 514 ending distally at the distal opening 512. The nozzle 514 may be sized to fit within an orifice within the implant 25 including, but not limited to the threaded bore 446 illustrated, for example at FIG. 11B. In this other aspect, the nozzle 514 may be sized to fit closely within the threaded bore 446. In an aspect, the nozzle 514 may be provided with threads configured to mesh within the threads of the threaded bore 446.

Figure 32:
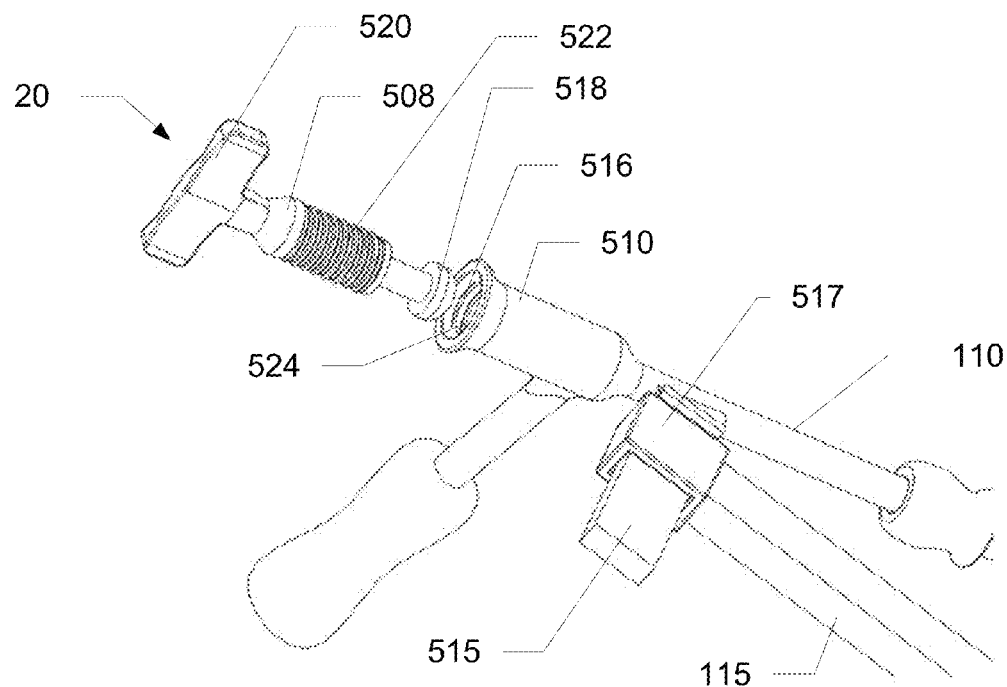
FIG. 32 is a perspective view of a delivery tool with a bone paste insertion element.

Referring now to FIG. 32, the barrel 516 may include a lumen 516 within which the bone paste material may be inserted prior to injection into the graft window 40. The plunger 508 may further include a distal end 518 configured to fit closely within the lumen 516 in order to develop pressure within the lumen when the plunger 508 is advanced distally into the lumen 516. In one aspect, the plunger 508 may be advanced by applying a distally directed force to the plunger handle 520. In another aspect, the plunger 508 may further include a threaded portion 522 configured to mesh with corresponding threads 524 formed within the barrel 510. In this aspect, the plunger may be advanced distally by twisting the threaded portion 522 into the corresponding threads 524.

Figure 33A:
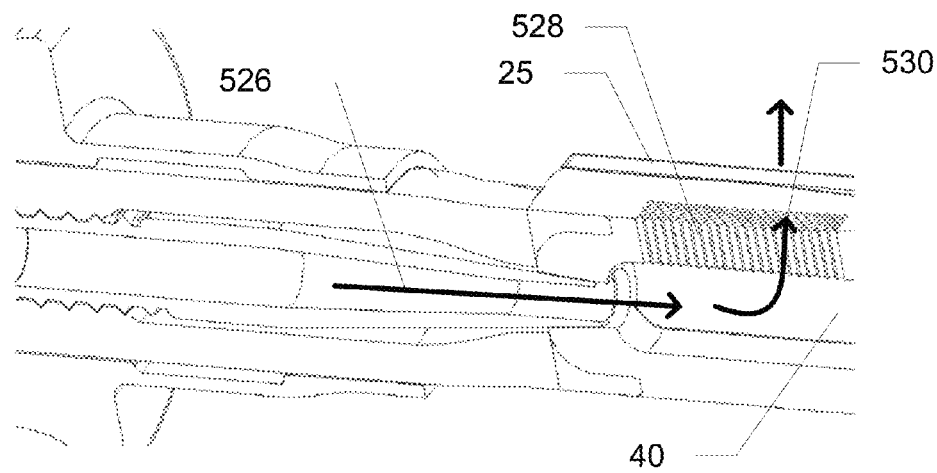
FIG. 33A is a cross-sectional close-up view of a delivery tool with a bone paste insertion element and an implant with a plurality of bone paste channels.

Referring to FIG. 33A, the bone paste material may advance outward into the graft window 40 of the implant 25 at the initial of the injection process, along a path 526. As the graft window 40 fills with bone paste material and the pressure within the graft window increases, additional bone paste material may enter the joint space (not shown) surrounding the implant 25. In an aspect, the implant 25 may be provided with a plurality of channels 528 connecting the volume within the graft window 40 to the joint space surrounding the implant 25. In this aspect, additional bone paste material may travel through the plurality of channel 528 to the joint space along a path 530. In various aspects, an amount of bone paste material sufficient to fill the graft window as well as the joint space surrounding the implant may be introduced using the delivery tool in the various aspects described herein above.

Figure 33B:
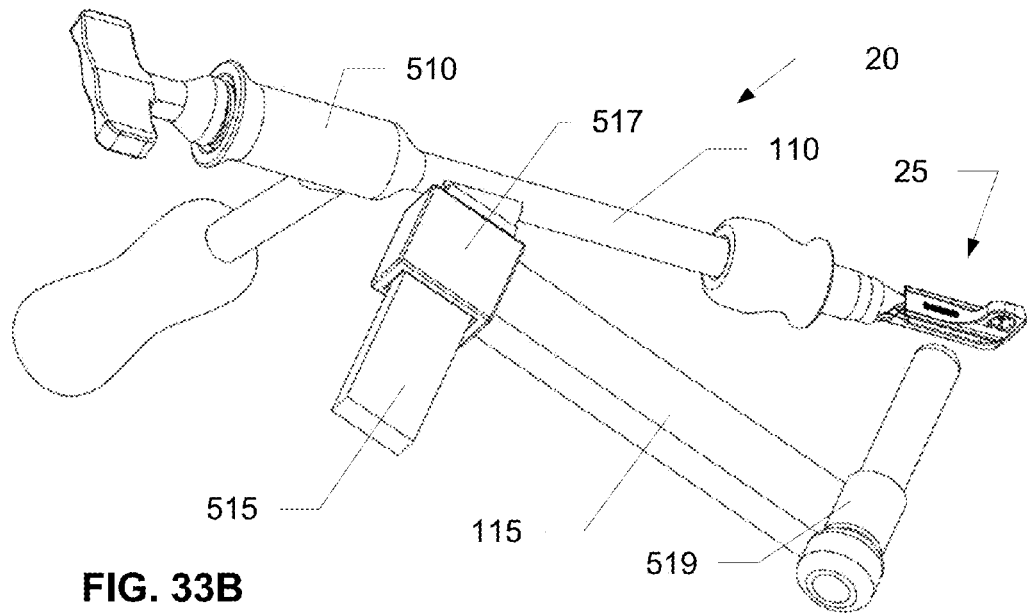
FIG. 33B is another perspective view of the delivery tool with the bone paste insertion element.
Figure 33C:
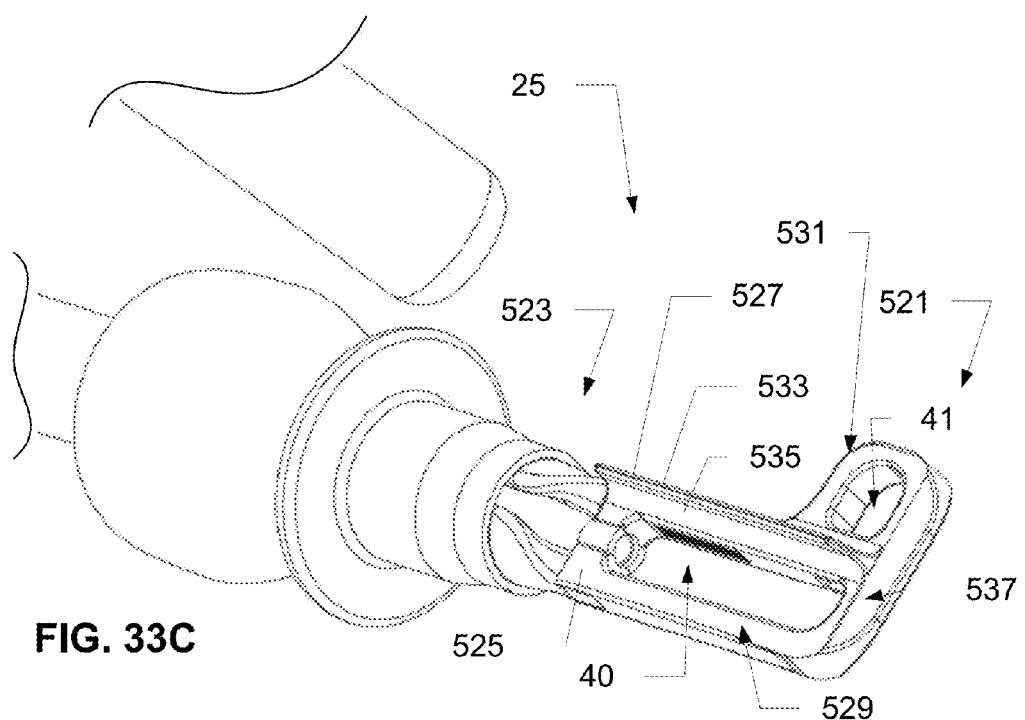
FIG. 33C is a close-up perspective view of the implant coupled to a distal end of the delivery tool.
Figure 33D:
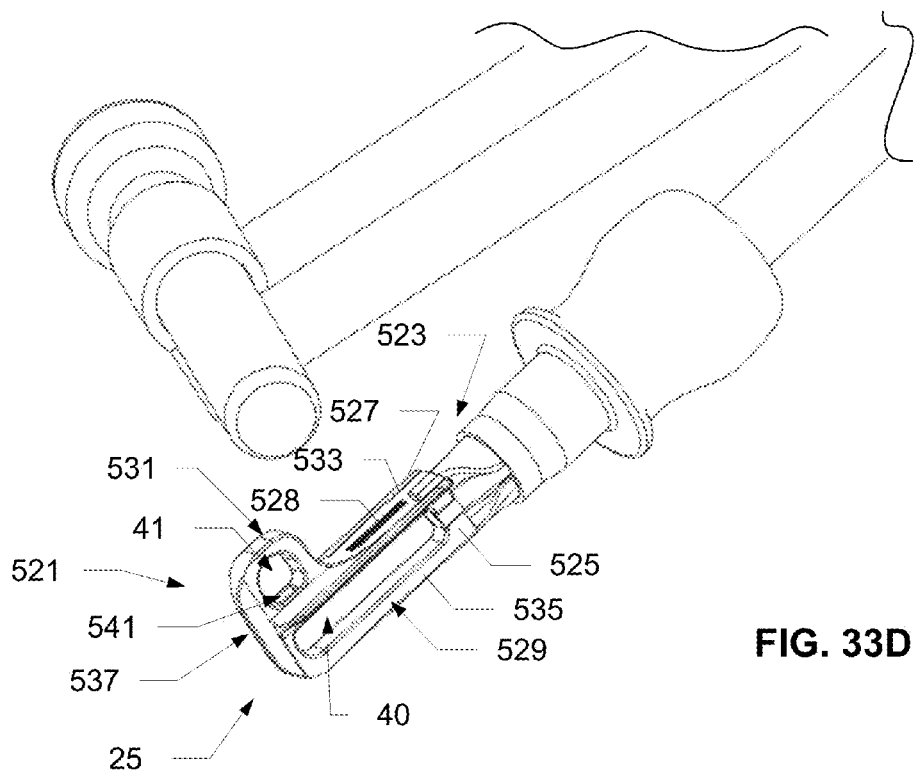
FIG. 33D is a close-up perspective view of the implant coupled to the distal end of the delivery tool from the opposite side as FIG. 33C.
Figure 33E:
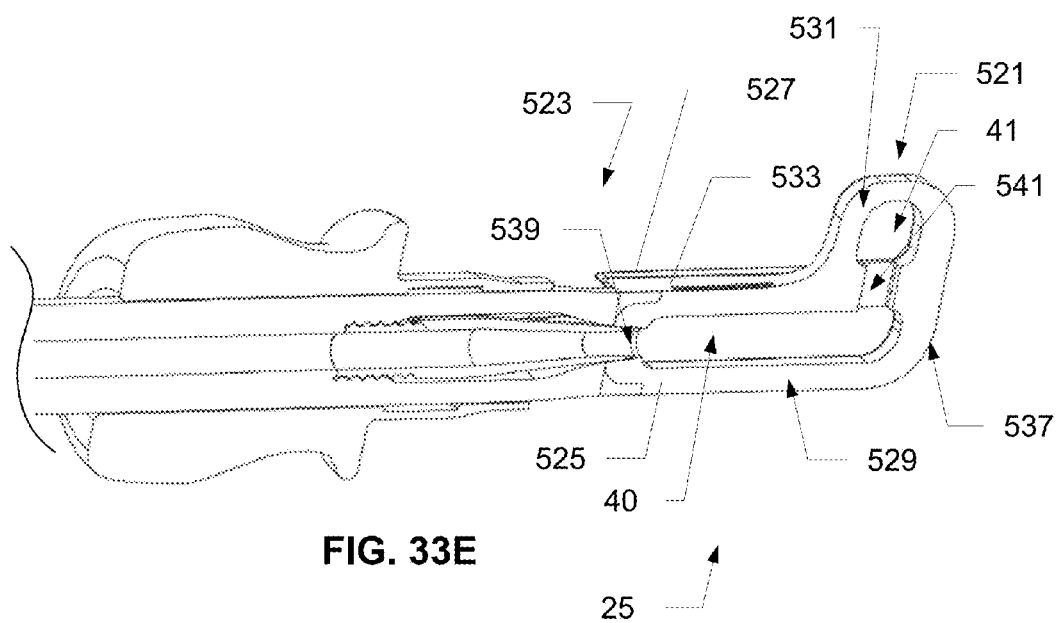
FIG. 33E is a cross-sectional side view of the implant and distal end of the delivery tool.

Reference is made to FIGS. 33B-33E, which depict additional views of the implant 25. In particular, FIG. 33B illustrates a top isometric view of the delivery tool 20 and implant 25, FIG. 33C illustrates a close-up isometric view of the implant 25 and distal end of the delivery tool 20, FIG. 33D illustrates a close-up isometric view of the implant 25 and the delivery tool 20 from an opposite side as FIG. 33C, and FIG. 33E illustrates a cross-sectional side view of the distal end of the delivery tool 20 and the implant 25.

As seen in FIG. 32, the anchor arm 115 may be slidably coupled with a guide beam 515 of the implant arm 110. The guide beam 515 may be attached to the implant arm 110 at one end and protrude from the implant arm 110 in a cantilevered configuration, wherein the protrusion angle of the guide beam 515 is configured to result in a predetermined anchor entry angle through the implant 25. The anchor arm 115 may be provided with a slideable fitting 517 at an end opposite the anchor arm collar 519, as seen in FIG. 33B. In this way, the slideable fitting 517 may be translated along the guide beam 515 to adjust the distance between the anchor arm collar 519 and the implant 25, while maintaining the angular relationship between the arms 110, 115, the collar 519, and the implant bore 40.

Referring to the implant 25, as shown in FIGS. 33B-33E, it includes a distal or leading end 521, a proximal or trailing end 523, a longitudinally extending body or intra-articular member 525, a first and second bore or void 40, 41 extending across the body 525, and keels, fins, or planar members 527 that extend outwardly away from the body 525. The shape of the body 525 is L-shaped, boot-shaped, or generally a shape matching a sacroiliac joint of a human. More particularly, the body 525 includes a rectangular body portion 529 and a projection 531 at the distal end 521 of the body 525 of the implant 25. The first void 40 extends through the rectangular body portion 529 and the second void 41 extends through the projection 531. As best seen in FIGS. 33C and 33D, the keels 527 extend outward from a superior or top edge 533 of the rectangular body portion 529 of the body 525 of the implant 25. The keels 527 extend from the proximal end 523 to the distal end 521 and bisect the rectangular body portion 529 and the projection 531.

The implant 25 includes opposite side surfaces 535 that are generally parallel with each other. The void 40 through the rectangular body portion 529 is elongate and generally extends from near the proximal end 523 to near the distal end 521. The portion of the body 525 of the implant 25 defining the distal end 521 of the implant 25 is tapered to an edge 537. At the proximal end 523 of the implant 25 is a bore 539 for coupling with the delivery tool 20 and also through which the bone paste material may be injected into the void 40 of the implant 25.

As seen in FIG. 33E, the first and second voids 40, 41 are connected by a passageway 541 so bone paste material injected into the void 40 of the implant 25 can then travel through the passageway 541 and into the second void 41 in the projection 531 at the distal end 521 of the implant 25.

III. Method of Fusing Sacroiliac Joint

Various aspects of the delivery system 10, delivery tool 20, and implant assembly 15 may be used to fuse a sacroiliac joint 1000 of a subject.

Figure 34:
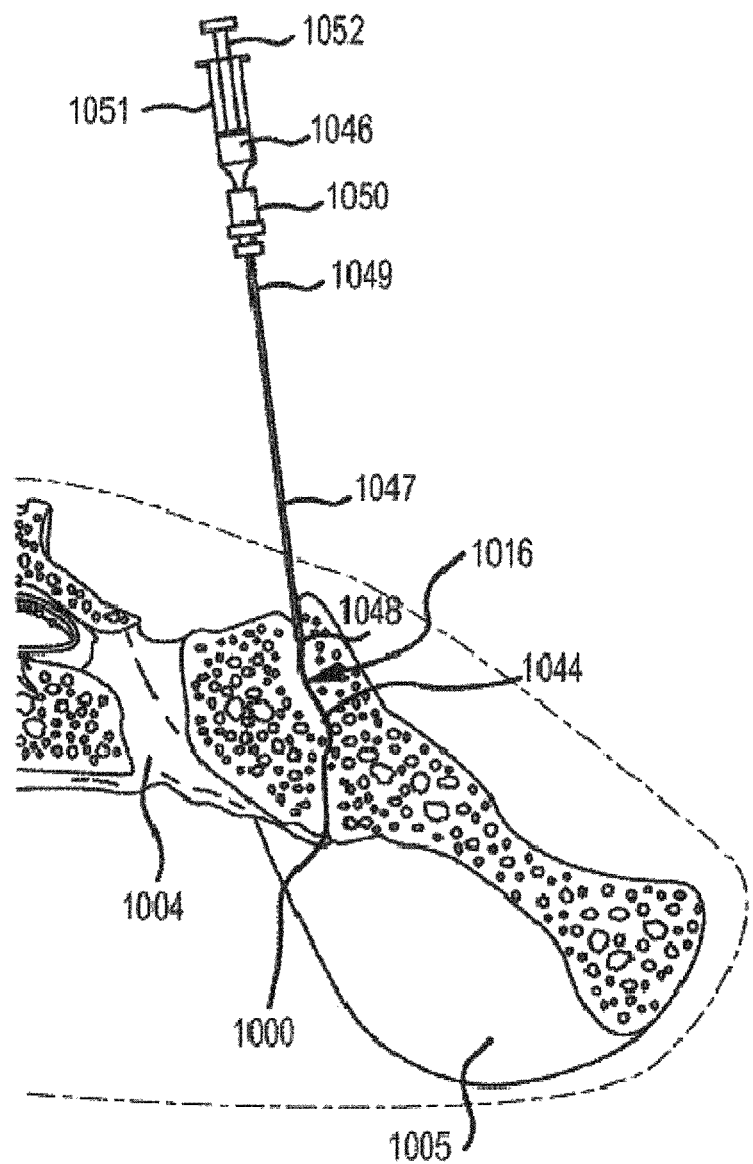
FIG. 34 is a transverse cross sectional view of a sacroiliac joint showing an injection of a radiographic contrast to outline the articular surfaces of the sacroiliac joint.

Referring to FIG. 34, the patient may be put under sedation and situated in a prone position on a translucent operating table or other suitable surface. The sacroiliac joint 1000 may be locally anesthetized to allow for injecting a radiographic contrast 1046 (as a non-limiting example, ISOVIEW 300™ radiographic contrast) under fluoroscopic guidance into the inferior aspect of the sacroiliac joint 1000 to outline the articular surfaces 1016 of the sacroiliac joint 1000 defined between the sacrum 1004 and ilium 1005 to visualize an intra-articular region 1044 of the sacroiliac joint 1000. Injection of the radiographic contrast 1046 within the sacroiliac joint 1000 may be accomplished utilizing any suitable tubular member 1047 including but not limited to a syringe needle, the tubular member 1047 having a first tubular member end 1048 which may be advanced between the articulating surfaces 1016 of the sacroiliac joint 1000. The tubular member 1047 may have a second tubular member end 1049 that removably couples to a hub 1050. The hub 1050 may be configured to removably couple to a syringe barrel 1051 or other suitable device to contain and deliver an amount of radiographic contrast 1046. In one non-limiting example, the syringe barrel 1051 may have an internal volume capable of receiving an amount of the radiographic contrast 1046 sufficient for outlining the articular surfaces 1016 of the sacroiliac joint 1000, for example, under lateral fluoroscopy. A plunger 1052 may be slidingly received within the barrel 1051 to deliver the radiographic contrast 1046 through the tubular member 1047 into the sacroiliac joint 1000. The tubular member 1047 may have a gauge ranging from about 16 gauge to about 20 gauge and may be incrementally marked on the external surface to allow determination of the depth at which the first needle end 1048 has advanced within the sacroiliac joint 1000. As the first needle end 1048 advances into the sacroiliac joint 1000, the radiographic contrast 1046 may be delivered from within the syringe barrel 1051 into the sacroiliac joint 1000 to allow visualization of the sacroiliac joint 1000 and location of the tubular needle 1047 within the sacroiliac joint 1000.

Figure 35:
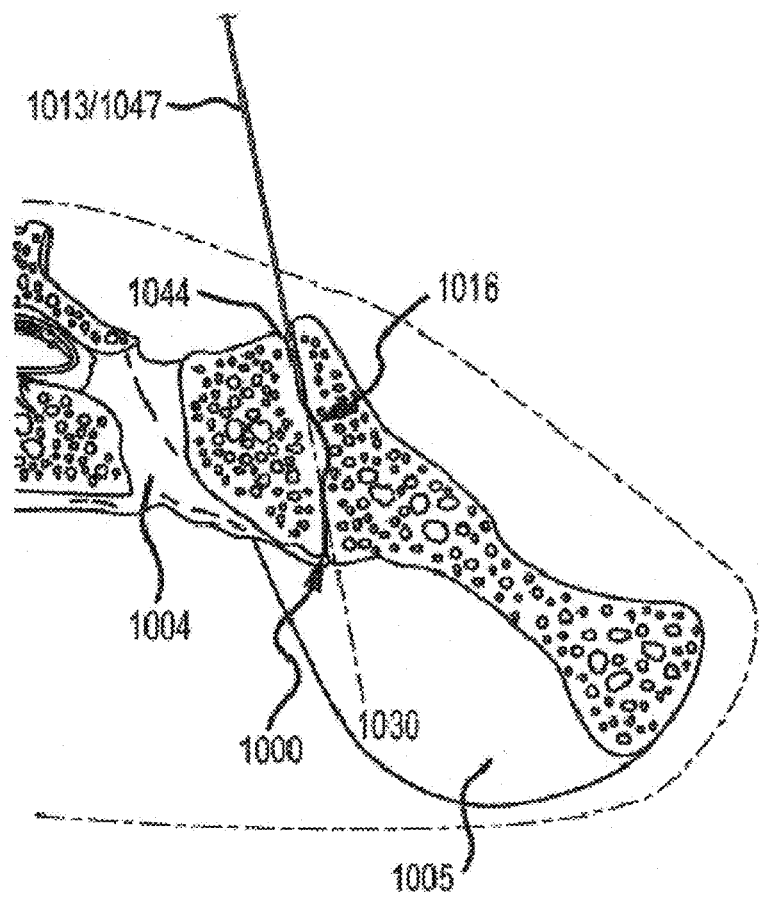
FIG. 35 is a transverse cross sectional view of a sacroiliac joint showing a tubular member fixed within the sacroiliac joint as an initial guide.

Referring now to FIG. 35, once the first tubular member end 1048 has been sufficiently advanced into the sacroiliac joint 1000 and the articular surfaces 1016 of the sacroiliac joint 1000 have been sufficiently visualized, the hub 1050 may be removed from the tubular member 1047, leaving the tubular member 1047 fixed within the sacroiliac joint 1000 as an initial guide for tools subsequently used to locate or place the sacroiliac joint implant 25 non-transversely within the joint plane 1030 generally defined between the articulating surfaces 1016 of the intra-articular region 1044 of the sacroiliac joint 1000 or to remove a portion of the sacroiliac joint 1000 within the region defined by the articular surfaces 1016 to generate an implant receiving space 1029. Alternately, one or more guide pins 1013 may be inserted along substantially the same path as the tubular member 1047 for fixed engagement within the sacroiliac joint 1000 and may be used to guide subsequent steps.

Figure 36:
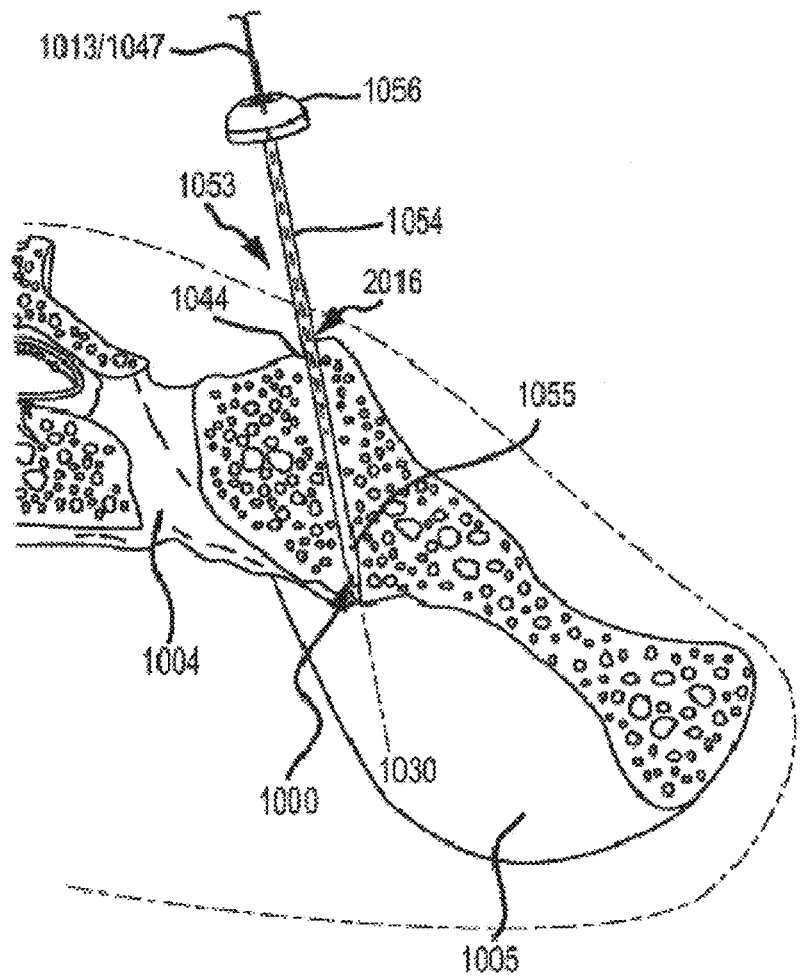
FIG. 36 is a transverse cross sectional view of a sacroiliac joint showing a cannulated probe slidingly engaged with the tubular member/guide pin extending outwardly from the sacroiliac joint.

Now referring primarily to FIG. 36, a small incision 1053 may be made in the skin at the posterior superior (or as to certain embodiments inferior) aspect of the sacroiliac joint 1000, extending proximal and distal to the tubular member 1047 along the line of the sacroiliac joint 1000 to provide a passage to access the intra-articular region 1044 between the articulating surfaces 1016 of the sacroiliac joint 1000. Referring to FIG. 42, the small incision 1053 may be made along the joint line 2019 of the sacroiliac joint 1000 in the tissue covering the posterior inferior access region 2016 of the sacroiliac joint 1000. Referring again to FIG. 36, a cannulated probe 1054 may be slidingly engaged with the tubular member 1047 (or guide pin 1013) extending outwardly from the sacroiliac joint 1000. While the sacroiliac joint 1000 may be illustrated in the FIGS. 34-41 as substantially linear for illustrative purposes, it is to be understood that the normal irregular features of the sacroiliac joint 1000 are not removed during the preparation of the sacroiliac joint 1000 prior to insertion of the implant 25. The cannulated probe 1054 may have a probe body 1054 of generally cylindrical shape terminating in a spatulate tip 1055 at the end advanced into the sacroiliac joint 1000. A removable cannulated probe handle 1056 may couple to the opposed end of the probe body 1054. The spatulate tip 1055 may be guided along the tubular needle 1047 or guide pin 1013 into the posterior portion of the sacroiliac joint 1000 and advanced to the anterior portion of the sacroiliac joint 1000 under lateral fluoroscopic visualization. The cannulated probe handle 1056 may then be removed providing the generally cylindrical probe body 1054 extending outwardly from the sacroiliac joint 1000 through the incision 1053 made in the skin.

Alternatively, the probe 1054 may be used to guide, advance or place a needle, guide wire or other instrument up to, near, or into the sacroiliac joint 1000.

Additionally, in particular embodiments, the probe handle 1056 and/or the opposed end of the probe body 1054, may be configured to have an interference fit or a luer lock hub to communicate with a syringe barrel 1051 in order to advance contrast, in situ curable biocompatible materials, stem cells, or other suitable compounds through the cannulated probe 1054 or cannulated probe handle 1056.

Figure 37:
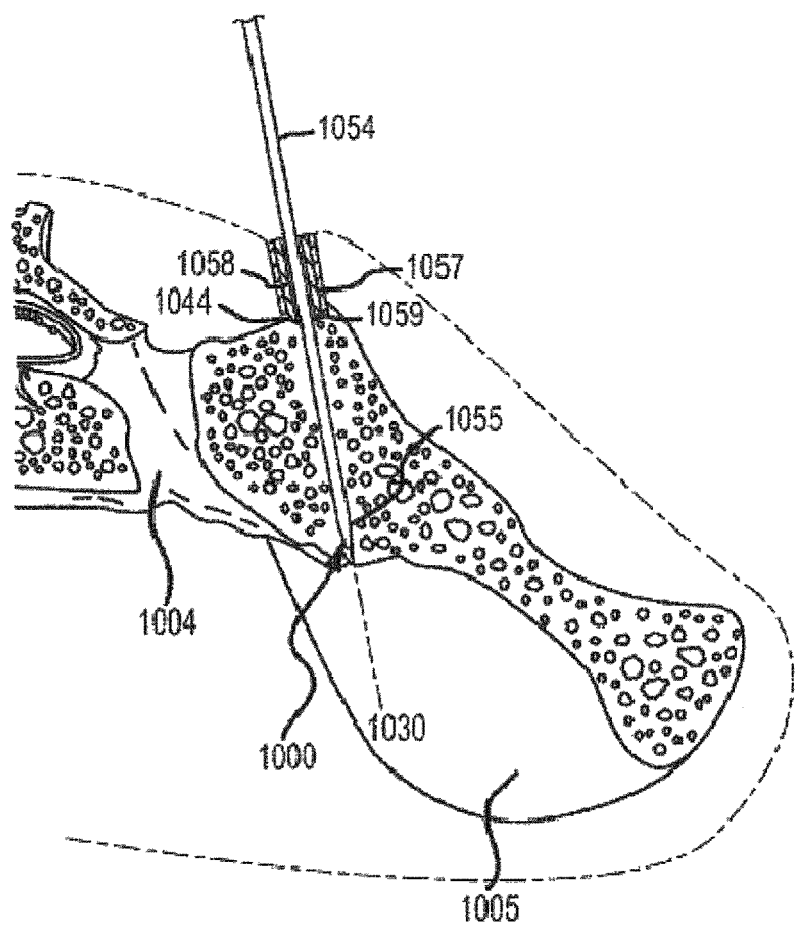
FIG. 37 is a transverse cross sectional view of a sacroiliac joint showing a soft tissue dilator advanced over a probe body and contacting the posterior aspect of the sacroiliac joint.

Now referring primarily to FIG. 37, a passage from the incision 1053 to the sacroiliac joint 1000 may be generated by inserting a cannula 1057 into the incision 1053. A soft tissue dilator 1058 having a blunt end 1059 may be advanced over the probe body 1054, or a plurality of soft tissue dilators of increasing size, until the blunt end 1059 of the soft tissue dilator 1058 and the corresponding cannula end contact the posterior aspect of the sacroiliac joint 1000. Referring to FIG. 42, in one embodiment, the ends of the dilator 1058 and cannula 1057 contact the joint line 2019 of the sacroiliac joint 1000 at the posterior inferior access region 2016 of the sacroiliac joint articular region 1044. Referring again to FIG. 37, the soft tissue dilator 1058 may be removed from within the cannula 1057. The external surface of the cannula 1057 may be sufficiently engaged with the surrounding tissue to avoid having the tissue locate within the lumen inside of the cannula 1057. A non-limiting embodiment of the cannula 1057 provides a tubular body having substantially parallel opposed side walls which terminate in a radius at both ends (lozenge shape) into which a plurality of different jigs may be inserted. Alternatively, as another non-limiting example, according to particular embodiments, the cannula 1057 and corresponding dilators 1058 and alignment jigs 1060 may be configured to have tubular bodies with an elliptical or circular cross section. In some embodiments, the cannula 1057 may be additionally configured to have within or near its walls a light source such as, for example, a fiber optic or a LED light source to assist in visualization of the working area. Also, in some embodiments, irrigation and suction tubing may communicate with the inside passage of cannula 1057.

Figure 38:
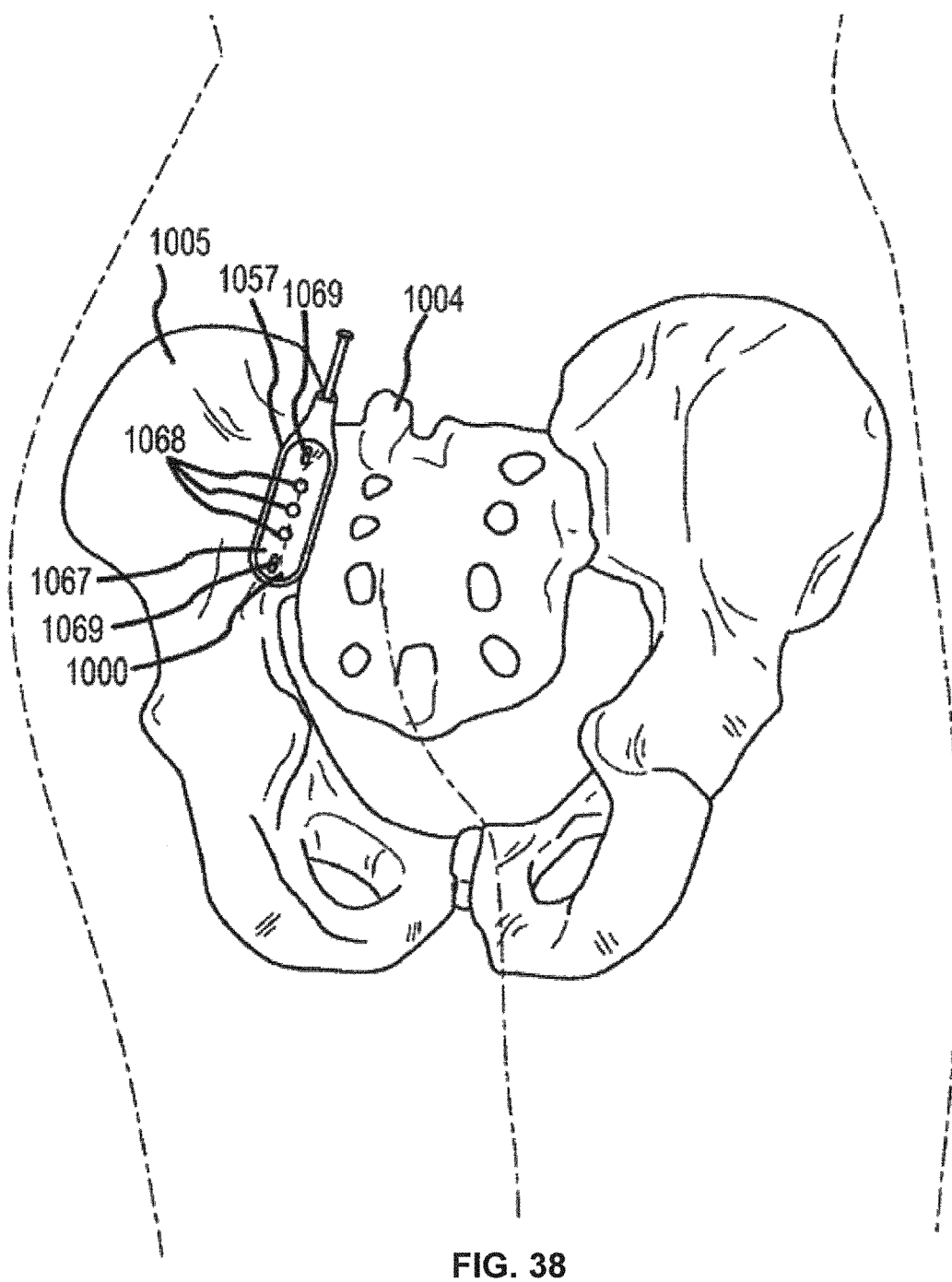
FIG. 38 is posterior-lateral view of a hip region of a subject, illustrating the placement of a cannula alignment jig.
Figure 39:
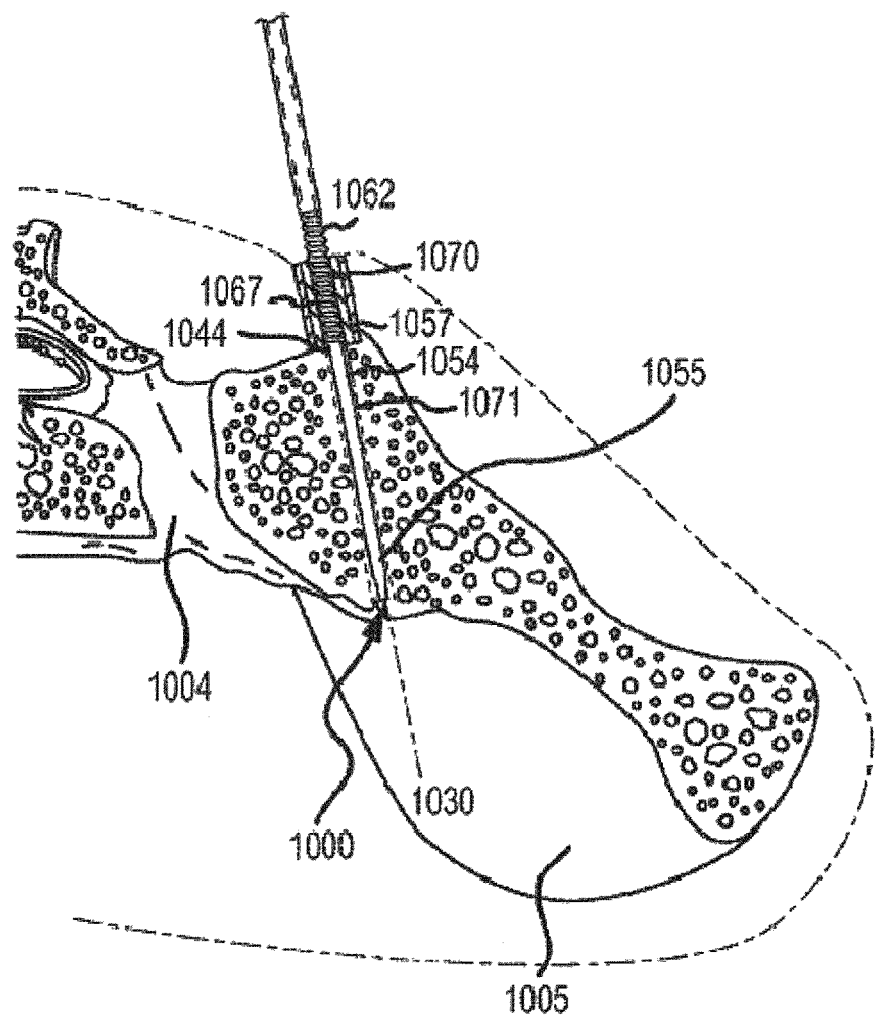
FIG. 39 is a transverse cross sectional view of a sacroiliac joint showing a cannulated drill bit advanced into the intra-articular region between the articulating surfaces of the sacroiliac joint to produce a first bore.

Now referring to FIGS. 38-39, a first drill jig 1067 may be advanced over the probe body 1054 (or guide pins 1013) and received within the cannula 1057. The probe body 1054 (or guide pin 1013) extending outwardly from the sacroiliac joint 1000 passes through a drill guide hole 1068 of the first drill jig 1067 (or a plurality of guide pins 1013 may extend through a corresponding plurality of guide pin holes 1069). The drill guide hole 1068 may take the form of a circular hole as shown in the FIG. 38, a slot, or other configuration to restrict the movement of the drill bit 1062 within the drill jig 1060 and to provide a guide for a drill bit 1062 in relation to the sacroiliac joint 1000. Guide pin holes 1069 may receive guide pins which may be positioned between the articular surfaces 1016 of the sacroiliac joint 1000 to demarcate the zone of desired treatment or safe working zones while using, for example, lateral fluoroscopy. As a non-limiting example, a first guide pin 1013 may be advanced through a first guide pin hole 1069, or alternatively a guide pin 1013 may first be inserted into the sacroiliac joint 1000 and subsequently a guide jig 1067 may be advanced over the guide pin 1013. Referring to FIG. 42, the first guide pin 1013 (not shown) may enter near the inferior end 2022 of the posterior inferior access region 2016 of the sacroiliac joint articular region 1044 via the sacroiliac joint line 2019 to border a portion of the greater sciatic notch 2008 thereby allowing a medical person, computer guided surgical system, or other observer to more easily highlight under x-ray a border which should not be crossed during the procedure due to the presence of nerve and other structures. Additionally, as a non-limiting example, first guide pin 1013 may configured as an electrode, insulated from the operator and the patient's soft tissues, and may be connected to a monitor to signal to an operator or surgeon when implant 25, configured with a stimulating electrode (NM), as discussed below, comes into contact with first guide pin. Referring again to FIGS. 38-39, a second guide pin 1013 may be placed in another guide pin hole 1069 to demarcate a second limit to a desired zone of treatment, or safe working zone. Referring to FIG. 42, a second guide pin 1013 (not shown) may enter near the superior end 2018 of the posterior inferior access region 2016 of the sacroiliac joint articular region 1044 via the sacroiliac joint line 2019 to be positioned to border an area of the sacroiliac joint 1000 such as a transition zone between the extra-articular 3007 and the intra-articular region 1044 which, for example, has been highlighted by contrast material as described above.

Referring again to FIG. 39, a cannulated drill bit 1070 may be advanced over the probe body 1054 and within a drill guide hole 1068 of the first drill jig 1067. The cannulated drill bit 1070 under fluoroscopic guidance may be advanced into the intra-articular region 1044 between the articulating surfaces 1016 of the sacroiliac joint 1000 to produce a first bore 1071 (shown in broken line) to a determined depth. As to certain embodiments of the method, an amount of articular cartilage or other tissues from between the articular surfaces 1016 of the sacroiliac joint 1000 may be removed to allow embodiments of the sacroiliac joint implant 25 to be implanted in replacement of the removed articular cartilage or tissue. Because the method removes the degenerative articular cartilage or tissue between the articular surfaces 1016 of the sacroiliac joint 1000, the articular surfaces 1016 of the sacroiliac joint 1000 may remain intact or substantially intact allowing the sacroiliac joint implant 25 to be non-transversely located between the articular surfaces 1016 of the sacroiliac joint 1000. Other instruments may be utilized separately or in various combinations with a cannulated drill bit 1062 for the removal of articular cartilage or tissue between articular surfaces 1016. Non-limiting examples of other instruments suitable for the removal of articular cartilage or tissue between articular surfaces 1016 include: endoscopy tools, box chisels, side cutting router bits, burs, flexible burs and bits, hole saws, curettes, lasers (such as $CO_2$, Neodymium/YAG (yttrium-aluminum-garnet), argon, and ruby), electrosurgical equipment employing electromagnetic energy (the cutting electrode can be a fine micro-needle, a lancet, a knife, a wire or band loop, a snare, an energized scalpel, or the like) where the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advancement into the joint without grossly penetrating much beyond the cartilage.

Figure 40:
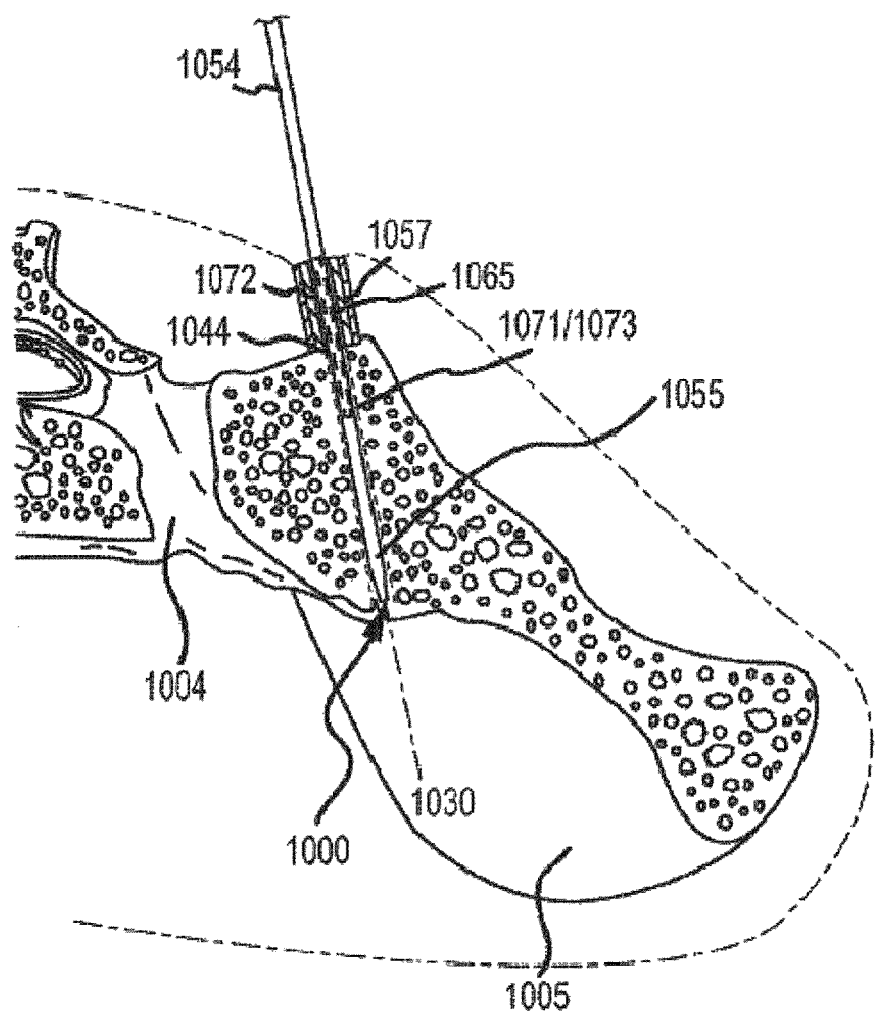
FIG. 40 is a transverse cross sectional view of a sacroiliac joint showing a second drill jig advanced over the probe body and received within the cannula.

Now referring to FIG. 40, as to certain embodiments of the disclosure, the first drill jig 1067 may be removed from within the cannula 1057 and a second drill jig 1072 may be advanced over the probe body 1054 and received within the cannula 1057; however, the disclosure is not limited to any particular number of drill jigs and as to certain embodiments of the method the first drill jig 1067 may include all the required drill guide hole(s) 1068 (or slots or other configurations of the drill guide) and as to other embodiments of the method a plurality of drill jigs can be utilized in serial order to provide all the drill guide holes 1068. As illustrated in FIG. 38, the first drill jig 1067 may provide one or more additional drill guide holes 1068 which guide in relation to the first bore 1071 a second or more cannulated drills 1062 of the same or different configuration to be inserted within and advanced into the sacroiliac joint 1000 to produce a second bore 1073 (generally shown in broken line as 1071/1073 in FIG. 40) or a plurality of bores within the sacroiliac joint 1000 spaced apart in predetermined pattern to allow removal of sufficient articular cartilage 1016 or other tissue from the intra-articular space of sacroiliac joint 1000 for placement of embodiments of the sacroiliac joint implant 25 within the intra-articular region 1044 defined by and between the paired articular surfaces 1016 of the sacroiliac joint 1000. In various aspects, the first drill jig 1067 or the second drill jig 1072 or a plurality of drill jigs may be utilized in serial order to remove a portion of the sacroiliac joint 1000 for generation of an implant receiving space 1029. As these embodiments of the method, articular cartilage or other tissues and sufficient subchondral bone can be removed from between the articular surfaces 1016 of the sacroiliac joint 1000 to allow placement of certain embodiments of the sacroiliac joint implant 25 and one or more transarticular channels 1074 (not shown) may be cut into at least one of the articular surfaces 1016 of said sacroiliac joint 1000 sufficient to the at least one keel 414 of the sacroiliac implant 25. The one or more transarticular channels 1074 may be cut a depth into the subchondral, cortical bone or cancellous bone of the sacrum 1004 or ilium 1005.

Figure 41:
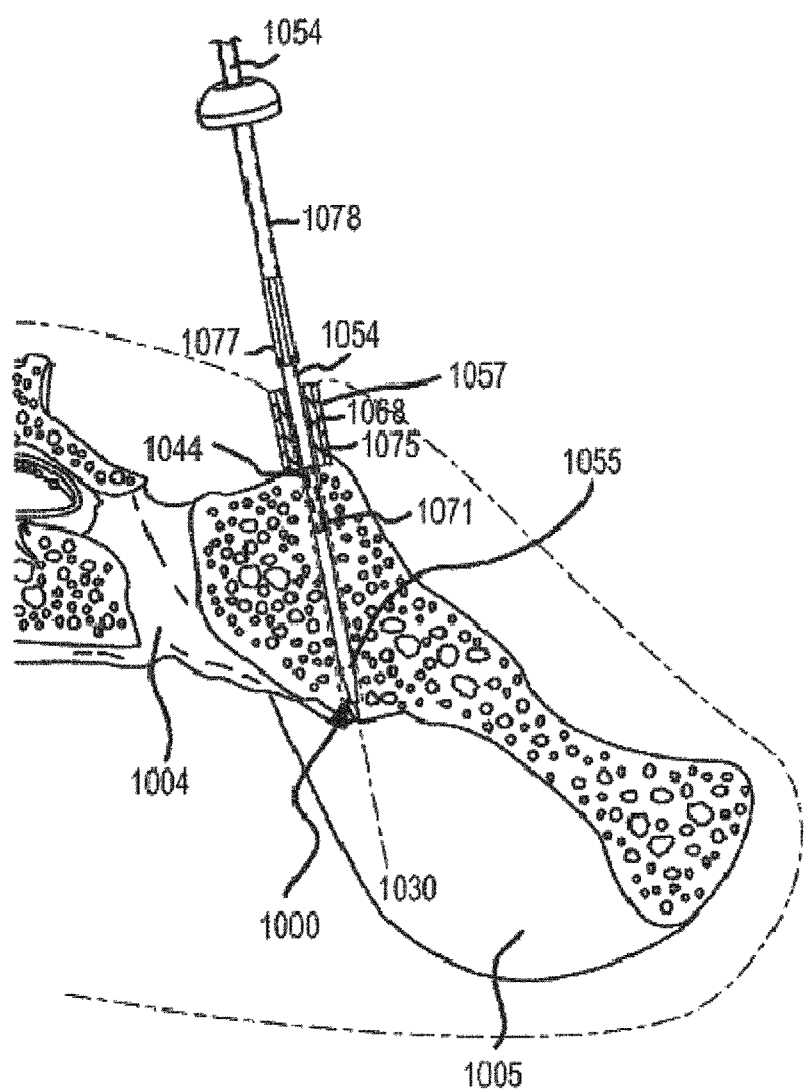
FIG. 41 is a transverse cross sectional view of a sacroiliac joint showing a broach jig advanced over the probe body and received within the cannula.
Figure 42:
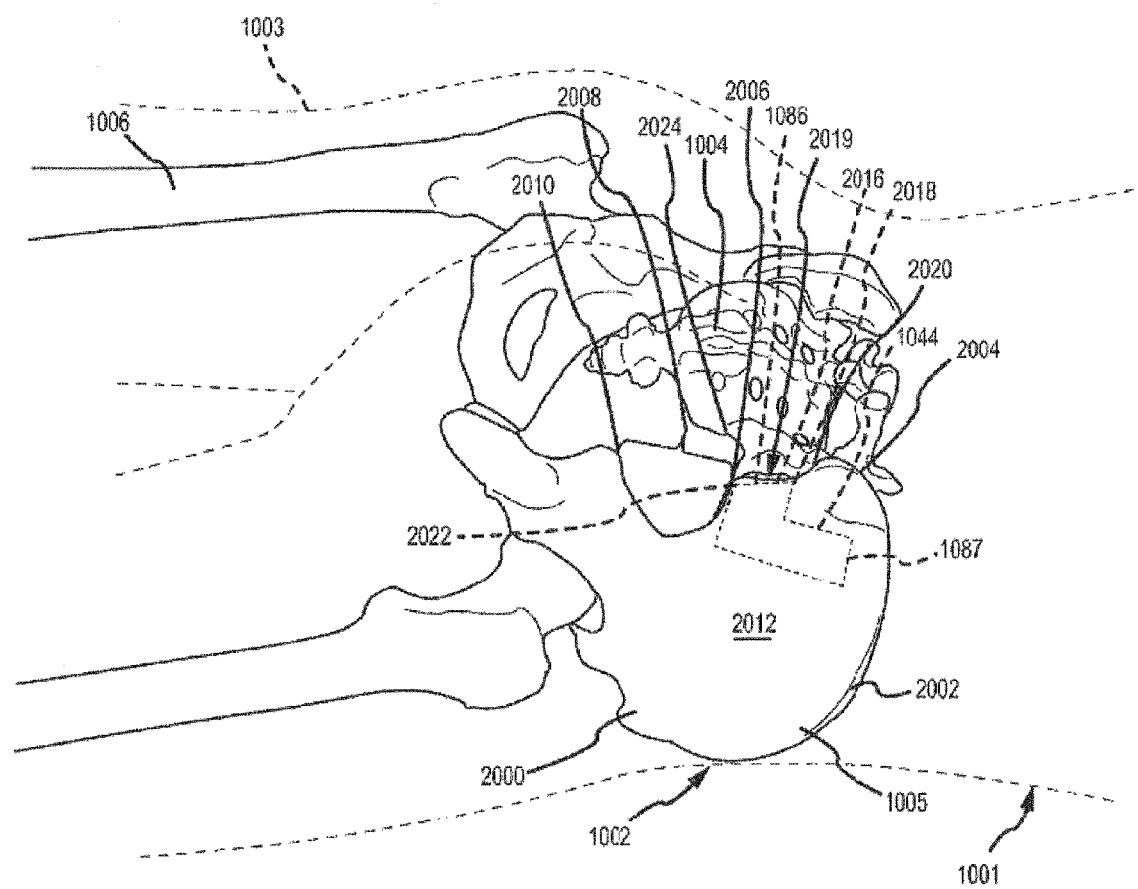
FIG. 42 is a lateral-posterior view of the hip region of a subject lying in a prone position.

Now referring primarily to FIG. 41, in a subsequent step, the last in the serial presentation of drill jigs 1067, 1072 (not shown) may be removed from within the cannula 1057 and a broach jig 1075 may be advanced over the probe body 1054 to locate within the cannula 1057. The broach jig 1075 may include a broach guide hole which receives a first broach end 1077 of a cannulated broach 1078 advanced over the probe body 1054. The first broach end 1077 may have a configuration which may be advanced into the sacroiliac joint 1000. As to certain embodiments of the method, the first broach end 1077 may be adapted to remove an amount of articular cartilage and other tissue from between the articular surfaces 1016 within the articular region 1044 of the sacroiliac joint 1000 for non-transverse placement of a sacroiliac joint implant 25 with at least one keel 414 adapted to extend into the bone of the sacrum 1004 and/or the ilium 1005. As to other embodiments of the method, the cannulated broach 1078 may remove a portion of the sacroiliac joint 1000 to generate an implant receiving space 1029 to receive embodiments of the sacroiliac joint implant 25 with at least one keel 414 adapted to extend into the bone of the sacrum 1004 and/or the ilium 1005.

As a non-limiting example, FIG. 41 shows a broach 1078 configured to remove a portion of the sacroiliac joint 1000 to produce an implant receiving space 1029 (not shown) to receive embodiments of the sacroiliac joint implant 25 with at least one keel 414 adapted to extend into the bone of the sacrum 1004 and/or the ilium 1005.

Figure 43:
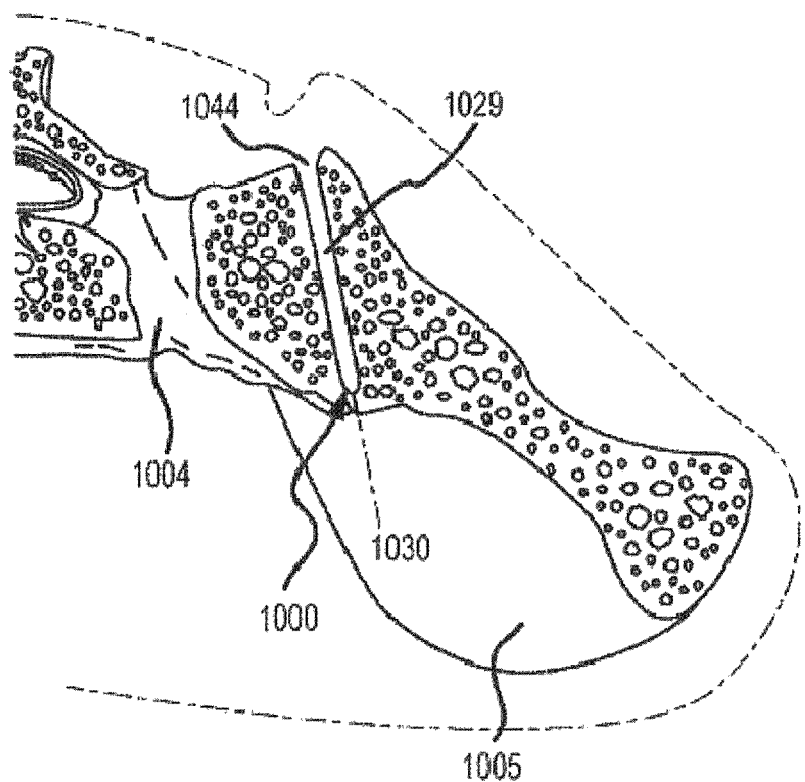
FIG. 43 is a transverse cross sectional view of a sacroiliac joint showing a receiving space for insertion of the implant.

Referring to FIG. 43, the implant receiving space 1029 and the sacroiliac joint implant 25 may include correspondingly related dimensions such that placement of the sacroiliac joint implant 25 within the implant receiving space 1029 disposes the sacrum 1004 and the ilium 1005 in a substantially immobilized relation and substantially avoids alteration of the positional relation of the sacrum 1004 and the ilium 1005 from the normal condition, and/or avoids driving together or driving apart the sacrum 1004 from the ilium 1005 outside of or substantially outside of the normal positional relation. An intention in selecting configurations of the sacroiliac joint implant 25 and the implant receiving space 1029 includes achieving immobilization of the sacrum 1004 in relation to the ilium 1005 while maintaining the sacroiliac joint 1000 in normal or substantially normal positional relation, or returning the sacroiliac joint 1000 to a normal or substantially normal positional relation to correct a degenerative condition of the sacroiliac joint 1000.

As a non-limiting example, configurations of an implant receiving space 1029 allow embodiments of the sacroiliac joint implant 25 to be placed non-transversely between the caudal portion of the articular surfaces 1016 of the sacroiliac joint 1000. While certain embodiments of the sacroiliac joint implant 25 may only provide an intra-articular element 408 and at least one keel 414 situated within a correspondingly configured implant receiving space 1029 to engage at least a portion of the bone of the ilium 1005 or sacrum 1004, the disclosure is not so limited. An anchor 30 may be inserted through the graft window 40 in the implant 25 and into the sacrum 1004 and ilium 1005 to fix the location of the implant 25 within the implant receiving space 1029.

While the preceding discussion is given in the context of the implant 25 being implanted non-transversely in the caudal portion 1086 of the sacroiliac joint 1000, in other embodiments, the implant 25 may be implanted in other locations within the sacroiliac joint. For example, as disclosed in U.S. patent application Ser. No. 12/998,712, which is incorporated herein by reference, in some embodiments, the implant 25 may be implanted non-transversely in the cranial portion of the sacroiliac joint 25 by similar procedures or steps as above described with the incision and generation of the passage to the superior articular portion of the sacroiliac joint 1000. The implant 25 may also be implanted in the sacroiliac joint in such a manner so as to extend between the cranial and caudal portions, as also disclosed in U.S. patent application Ser. No. 12/998,712.

Figure 45:
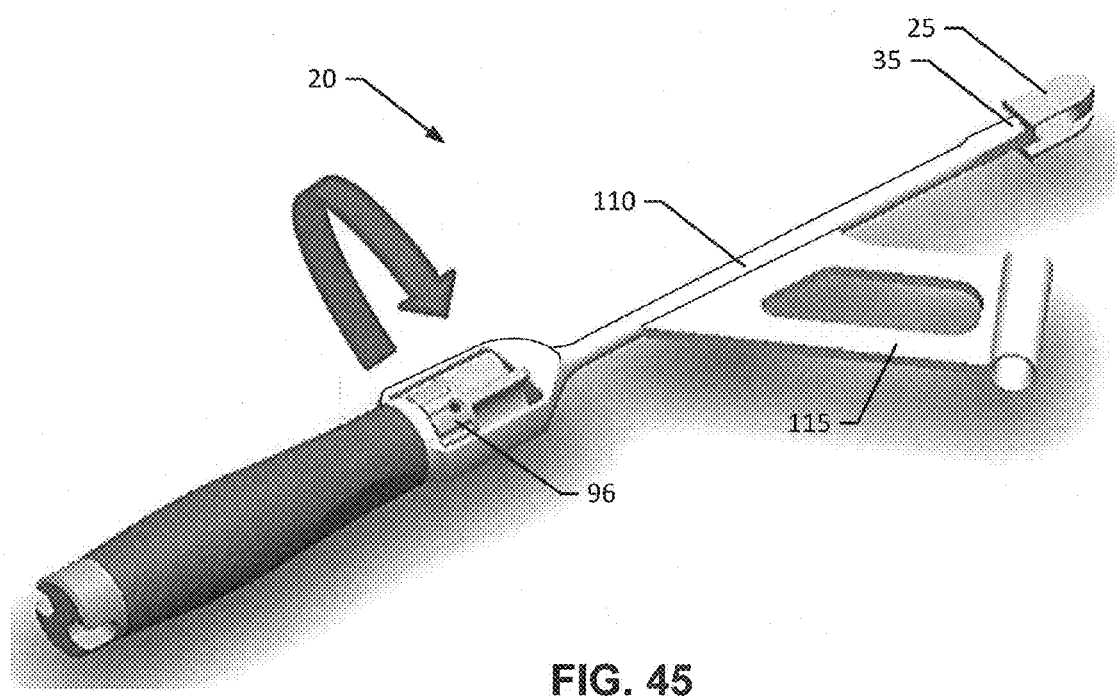
FIG. 45 is a perspective view illustrating the attachment of an implant to an implant arm of a delivery tool.

Once the implant receiving space 1029 has been created, the implant 25 may be mounted to the delivery tool 20 as described herein previously and as illustrated in FIGS. 11A-11B. Referring to FIG. 45, the implant 25 may be supported off of the distal end 35 of the implant arm 110 of the delivery tool 20. In one aspect, the implant 25 may be reversibly attached by aligning the alignment bores 452A/452B within the proximal face 454 of the implant 25 with the alignment protrusions 255A/255B protruding distally from the distal end 35 of implant arm 110, as illustrated in FIG. 11A. The retainer knob 96 may then be rotated by the practitioner to advance the threaded shaft 220 of the implant arm 110 into the threaded bore 446, thereby holding the proximal face 454 of the implant 25 pressed against the distal end 35 of the implant arm 110.

Figure 44:
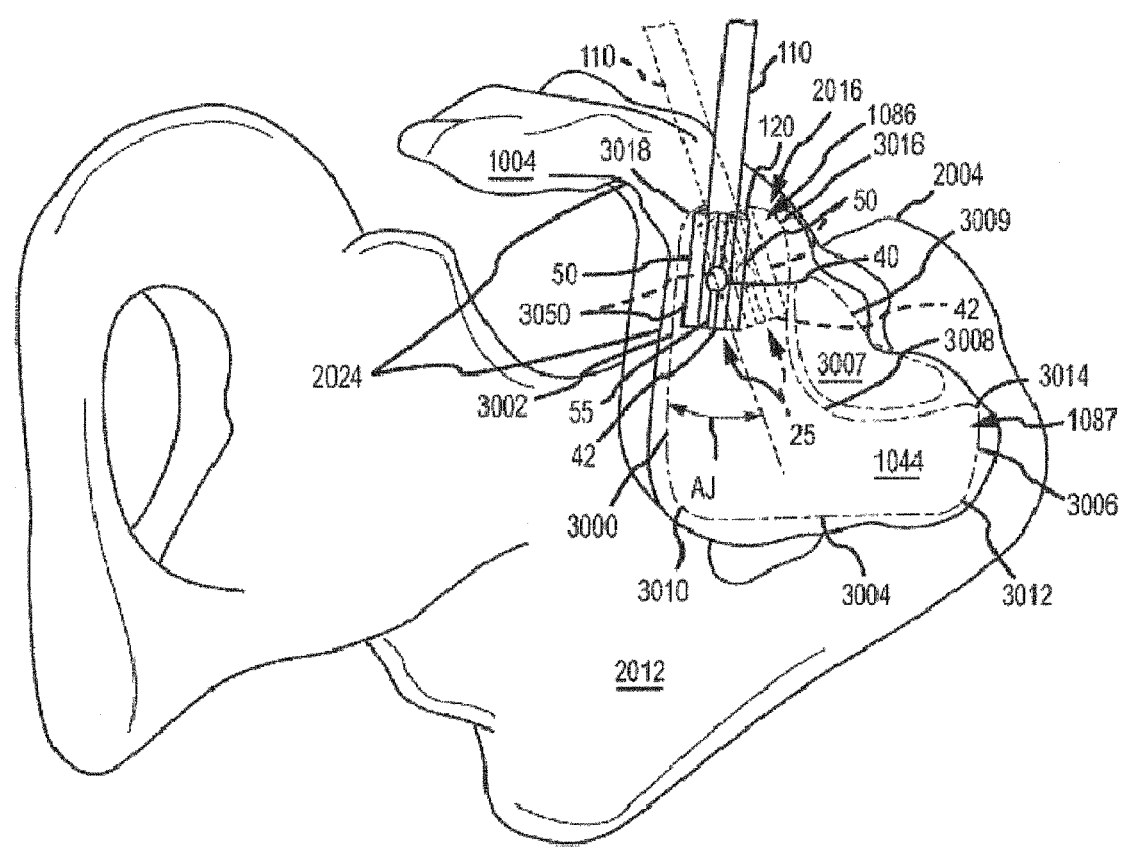
FIG. 44 is a right lateral side view of a hip region of a patient lying prone in with the implant positioned for implantation within the sacroiliac joint space by a delivery tool. The ilium is hidden in this view to show the sacroiliac joint space boundary defined along the sacrum.
Figure 46:
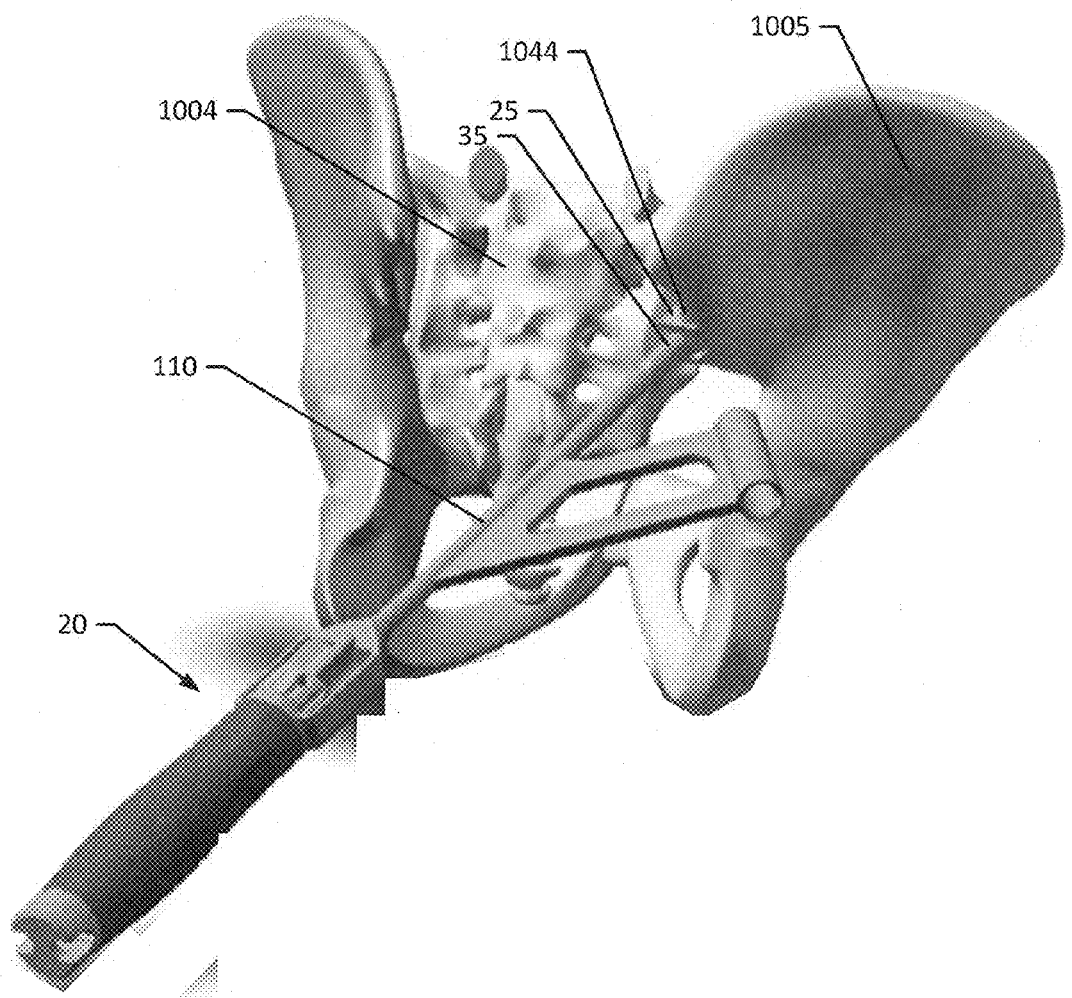
FIG. 46 is a posterior view illustrating the insertion of an implant into the joint space of a sacroiliac joint of a subject using a delivery tool.

Referring to FIG. 46, delivery tool 20 may then be positioned such that the distal end 406 of the implant 25 begins to enter the sacroiliac joint articular region 1044 via the posterior inferior access region 2016, which is described in detail above. In entering the sacroiliac joint space 1044, the implant 25 may be oriented such that its intra-articular element 108 is oriented generally parallel to, and aligned with, the sacroiliac joint space 1044 and the implant's keels 414/416 are generally transverse to the joint plane 1030. Referring to FIG. 44, the longitudinal axis $LCA_2$ of the implant arm 110 of the delivery tool 20 has a generally anterior trajectory that is located within the joint plane 1030. Alternatively, according to particular embodiments, as a non-limiting example, the longitudinal axis $LCA_2$ of the implant arm 110 of the delivery tool 20 can have a trajectory which can be defined as being generally lateral or, in particular embodiments, generally posterior. In some embodiments, when the implant 25 is delivered into the joint space, the implant arm 110 can be said to be at least one of generally superior or cephalad the sciatic notch 2008.

Referring again to FIG. 44, the implant 25 may be inserted via the implant arm 110 of the delivery tool 20 into the caudal region 1086 of the sacroiliac joint articular region 1044. The implant 25 may enter the posterior inferior access region 2016, and may be further advanced into the caudal region 1086 of the sacroiliac joint articular region 1044, in an orientation such that the implant arm 110 and intra-articular element 108 of the implant 25 are aligned within the joint plane 1030 and the top edge 428 next to the inferior boundary segment 3002 is generally parallel to, and immediately adjacent to, the inferior boundary segment 3002. The distal end 406 of the implant 25 is heading generally perpendicular to, and towards, the anterior boundary 3004.

In an aspect, a depth gage may be used to determine an appropriate implant length 402. An appropriate trial may be used to determine an appropriate implant height 426 and intra-articular thickness 440 for the prepared the implant receiving space 1029. A broach may be used to finish preparing the implant receiving space 1029 in some aspects. The cutting tools, trials and broaches should not be advanced beyond the anterior boundary 3004 of the sacroiliac joint 1000 or into the greater sciatic notch 2024. Fluoroscopy may be used to obtain a lateral view to assist with boundary identification.

By way of non-limiting example, the implant 25 may be inserted into the implant receiving space 1029 while monitoring the lateral view in order to not advance implant 25 into the greater sciatic notch 2024 or beyond the anterior boundary 3004 of the sacroiliac joint 1000.

The anchor arm 115 may be used to align and advance a soft tissue protector up to the skin (either over the ilium 1005 for a generally lateral to medial trajectory, or, over the sacrum 1004 for a generally medial to lateral trajectory. The soft tissue may be dissected bluntly to the ilium 1005 or to the sacrum. The soft tissue protector may be inserted up to the bone of the ilium or sacrum. A guide wire may be advanced using the drill sleeve held in place by the targeting arm aligned with the bore of the implant or alternatively aligned to place an anchor around the implant while avoiding hitting the implant 25.

Although various representative embodiments of this disclosure have been described above with a certain degree of particularity, those skilled in the art could make numerous alterations to the disclosed embodiments without departing from the spirit or scope of the inventive subject matter set forth in the specification. All directional references (e.g., top, bottom) are only used for identification purposes to aid the reader's understanding of the embodiments of the present disclosure, and do not create limitations, particularly as to the position, orientation, or use of the disclosure unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

In methodologies directly or indirectly set forth herein, various steps and operations are described in one possible order of operation, but those skilled in the art will recognize that steps and operations may be rearranged, replaced, or eliminated without necessarily departing from the spirit and scope of the present disclosure. It is intended that all matter contained in the above description or shown in the accompanying drawings shall be interpreted as illustrative only and not limiting. Changes in detail or structure may be made without departing from the spirit of the disclosure as defined in the appended claims.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A sacroiliac joint fusion system comprising:
    a) a joint implant comprising: a longitudinal axis extending between a proximal end and a distal end of the joint implant; and a first bore extending non-parallel to the longitudinal axis;
    b) an anchor element configured to be received in at least one of a sacrum or an ilium; and
    c) a delivery tool comprising:
        i) an implant arm comprising a shaft extending between a proximal end and a distal end of the implant arm and a handle at the proximal end, the distal end of the implant arm configured to releasably couple to the proximal end of the joint implant; and
        ii) an anchor arm comprising an anchor guide coupled to the implant arm via a distal articulating member and a proximal articulating member, the distal articulating member rotatably coupled with implant arm at a first end and rotatably coupled with the anchor guide at a second end, the proximal articulating member slidably coupled with the implant arm at a third end and configured to slidably translate distal-proximal along the shaft of the implant arm, the proximal articulating member rotatably coupled with anchor guide at a fourth end, the anchor guide configured to align the anchor element in a trajectory such that the anchor element will be received in the at least one of the sacrum or the ilium when the anchor element is guided by the anchor guide, wherein, when the third end of the proximal articulating member is positioned in a proximal-most position, the anchor guide is configured to align the anchor element in the trajectory, and when the third end of the proximal articulating member is positioned in a distal-most position, the anchor guide is configured to align the anchor element in the trajectory.

2. The system of claim 1, wherein the first end is positioned distally of the third end on the implant arm.

3. The system of claim 2, wherein the second end is positioned distally of the fourth end on the anchor guide.

4. The system of claim 1, wherein the implant arm further comprises an actuation assembly that is configured to releasably couple and decouple with the joint implant.

5. The system of claim 1, wherein the actuation assembly is rotationally actuated.

6. The system of claim 1, wherein an angle of the trajectory relative to the longitudinal axis of the joint implant is different when the third end is in the proximal-most position and the distal-most position.

7. The system of claim 1, wherein, when the third end is in the proximal-most position, an angle between the trajectory and a longitudinal axis of the shaft of the implant arm is about 34 degrees.

8. The system of claim 1, wherein, when the third end is in the distal-most position, an angle between the trajectory and a longitudinal axis of the shaft of the implant arm is about 45 degrees.

9. The system of claim 1, wherein the first end of the distal articulating member includes a stop feature that inhibits rotation of the first end beyond a certain point.

10. The system of claim 9, wherein the stop feature is configured to contact the shaft of the implant arm when the third end of the proximal articulating member is in the proximal-most position.

11. The system of claim 1, wherein the joint implant comprises:
an intraarticular element extending an implant length between the proximal and distal ends and further extending an implant height between an implant upper edge and an opposed implant lower edge, the intraarticular element comprising:
a first articular face and an opposed second articular face extending the implant height and at least a portion of the implant length;
the first bore formed within at least a portion of the intraarticular element and extending through the intraarticular element from the first articular face to the second articular face; and
at least one keel attached to the intraarticular element along at least a portion of the implant length.

12. The system of claim 11, wherein each keel of the at least one keels projects perpendicularly outward from the first articular face and from the second articular face, ending in a first edge and a opposite second edge separated by a keel width.

13. The system of claim 12, wherein the first edge and the second edge are in parallel alignment along the implant length.

14. The system of claim 12, wherein the first edge and the second edge distally converge toward one another.

15. The system of claim 14, wherein the at least one keel comprises a first keel extending from the proximal end to the distal end, wherein the first keel is attached along the implant upper edge or the implant lower edge.

16. The system of claim 15, wherein the at least one keel further comprises a second keel extending from the proximal end to the distal end, wherein the second keel is attached along the implant upper edge or the implant lower edge opposite to the first keel.

17. The system of claim 16, wherein the keel width of the first keel is equal to the keel width of the second keel.

18. The system of claim 16, wherein the keel width of the first keel is larger than the keel width of the second keel.

19. The system of claim 11, wherein the at least one keel comprises a first keel extending from the proximal end to the distal end, wherein the first keel is attached to the intraarticular element between the implant upper edge and the implant lower edge.

20. The system of claim 17, wherein the first keel further comprises a keel gap extending over an intersection of the first keel with the first bore.

21. The system of claim 11, wherein the first bore extends through the intraarticular element along a bore axis forming an angle ranging from about 45 degrees to about 90 degrees relative to a plane parallel to the first articular face or the second articular face.

22. The system of claim 11, wherein the first bore further comprises a bore length extending along a portion of the implant length, the portion ranging from about 40% to about 70% of the implant length.

23. The system of claim 22, wherein the bore length is situated between the proximal end and the distal end.

24. The system of claim 23, wherein one end of the bore length is coincident with the distal end.

25. The system of claim 11, wherein the anchor passes through the first bore.

26. The system of claim 11, wherein the anchor passes outside of the implant above the upper edge or below the lower edge.

27. The system of claim 11, wherein the intraarticular element further comprises:
a proximal face situated at the implant proximal end; and
a threaded bore extending from the proximal face along the implant length toward the distal end and opening distally into the first bore.

28. The system of claim 11, wherein the at least one keel and the intraarticular element taper distally into a distal edge situated at the distal end.

29. The system of claim 11, wherein the implant length ranges from about 20 mm to about 50 mm.

30. The system of claim 11, wherein the implant height ranges from about 10 mm to about 20 mm.

31. The system of claim 11, wherein an intraarticular thickness between the first articular face and the second articular face ranges from about 5 mm to about 7 mm.

32. The system of claim 12, wherein the keel width ranges from about 10 mm to about 20 mm.

33. The system of claim 1, wherein the anchor element is configured to avoid contact with the joint implant when aligned in the trajectory.

34. The system of claim 1, wherein the anchor element will be received within the first bore when the anchor element is guided by the anchor guide along the trajectory.

35. A sacroiliac joint fusion system comprising:
a) a joint implant comprising a body;
b) an anchor element configured to be received in at least one of a sacrum or an ilium; and
c) a delivery tool comprising:
  i) an implant arm comprising a shaft extending between a proximal end and a distal end of the implant arm, the distal end of the implant arm configured to releasably couple to the joint implant; and
  ii) an anchor arm comprising an anchor guide coupled to the implant arm, the anchor guide being articulable relative to the implant arm between pre-set orientations that are configured to align the anchor element in re-set trajectories relative to the joint implant, wherein the anchor element is configured to be received in the at least one of the sacrum or the ilium while avoiding contact with the joint implant when the anchor element is guided by the anchor guide in the pre-set trajectories,
wherein the anchor guide is coupled to the implant arm via a distal articulating member and a proximal articulating member, the distal articulating member rotatably coupled with implant arm at a first end and rotatably coupled with the anchor guide at a second end, the proximal articulating member slidably coupled with the implant arm at a third end and configured to slidably translate distal-proximal along the shaft of the implant arm, the proximal articulating member rotatably coupled with anchor guide at a fourth end.

36. The system of claim 35, wherein, when the third end of the proximal articulating member is positioned in a proximal-most position, the anchor guide is configured to align the anchor element in a first trajectory of the pre-set trajectories, and when the third end of the proximal articulating member is positioned in a distal-most position, the anchor guide is configured to align the anchor element in a second trajectory of the pre-set trajectories.

37. The system of claim 36, wherein an angle between the first trajectory and a longitudinal axis of the shaft of the implant arm is about 34 degrees.

38. The system of claim 36, wherein, when the third end is in the distal-most position, an angle between the second trajectory and a longitudinal axis of the shaft of the implant arm is about 45 degrees.

39. The system of claim 36, wherein the first end of the distal articulating member includes a stop feature that inhibits rotation of the first end beyond a certain point.

40. The system of claim 39, wherein the stop feature is configured to contact the shaft of the implant arm when the third end of the proximal articulating member is in the proximal-most position.

* * * * *